US008563777B2

(12) United States Patent
Smith et al.

(10) Patent No.: US 8,563,777 B2
(45) Date of Patent: *Oct. 22, 2013

(54) IONIZABLE ISOTOPIC LABELING REAGENTS FOR RELATIVE QUANTIFICATION BY MASS SPECTROMETRY

(75) Inventors: Lloyd M. Smith, Madison, WI (US); Michael R. Shortreed, Portage, WI (US); Brian L. Frey, Madison, WI (US); Margaret F. Phillips, Madison, WI (US); Joshua J. Coon, Middleton, WI (US); Shane M. Lamos, Winooski, VT (US); Casey J. Krusemark, Woodside, CA (US); Peter J. Belshaw, Madison, WI (US); Madhusudan Patel, Somerset, NJ (US); Neil L. Kelleher, Urbana, IL (US)

(73) Assignees: Wisconsin Alumni Research Foundation, Madison, WI (US); The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/155,682

(22) Filed: Jun. 8, 2011

(65) Prior Publication Data

US 2012/0022230 A1   Jan. 26, 2012

Related U.S. Application Data

(62) Division of application No. 11/726,307, filed on Mar. 21, 2007, now Pat. No. 7,982,070.

(60) Provisional application No. 60/784,400, filed on Mar. 21, 2006.

(51) Int. Cl.
C07C 211/10 (2006.01)
C07C 211/11 (2006.01)
G01N 33/58 (2006.01)

(52) U.S. Cl.
USPC .......................................... 564/291; 436/106

(58) Field of Classification Search
USPC .......................................... 564/291; 436/106
See application file for complete search history.

(56) References Cited

U.S. PATENT DOCUMENTS

| | | | |
|---|---|---|---|
| 4,354,045 | A | 10/1982 | Merger et al. |
| 5,961,991 | A | 10/1999 | Wenke et al. |
| 6,649,907 | B2 | 11/2003 | Ebeling et al. |
| 6,797,945 | B2 | 9/2004 | Berggen et al. |
| 6,906,322 | B2 | 6/2005 | Berggen et al. |
| 7,078,679 | B2 | 7/2006 | Westphall et al. |
| 7,982,070 | B2 * | 7/2011 | Smith et al. .................... 564/291 |
| 2005/0199804 | A1 | 9/2005 | Hunt et al. |

FOREIGN PATENT DOCUMENTS

| | | |
|---|---|---|
| CS | 268 639 | 8/1989 |
| CS | 272 135 | 4/1990 |
| EP | 1 512 679 | 3/2005 |
| GB | 1 383 127 A | 2/1975 |
| JP | 2005047840 | 2/2005 |
| WO | WO 2004008480 | 1/2004 |
| WO | WO 2004070352 | 8/2004 |
| WO | WO 2004086050 | 10/2004 |

OTHER PUBLICATIONS

Abderhalden et al. CAS Accession No. 1929:9684, 1929.*
Abderhalden et al., CAS Accession No. 1929:9684, 1929.
Aebersold, R. et al. *Nature* (2003) 422:198-207.
Aharoni, A. et al. *Omics* (2002) 6:217-234.
Barry et al. *Rapid Commun. Mass Spectrom.* (2003) 17:484-497.
Barry et al. *Rapid Commun. Mass Spectrom.* (2003) 17:603-620.
Birkemeyer, C. et al. *Trends Biotechnol.* (2005) 23:28-33.
Cech, NB. et al.*Anal. Chem.* (2000) 72:2717-2723.
Choi, BK. *Chromatogr. A*. (2001) 907:337-342.
Constantopoulos, TL. et al. *Am. Soc. Mass Spectrom.* (1999) 10:625-634.
Dalluge, LL. et al. *Chromatogr. A* 2004) 1043;3-7.
Enke, CG. *Anal. Chem.* (1997) 69:4885-4893.
Fiehn, O. et al. *Nature Biotechnol.* (2000) 18:1157-1161.
Gygi, SP. et al. *Nature Biotechnol.* (1999) 17:994-999.
Hegeman, AD. et al. *J. Am. Soc. Mass. Spectrom.* (2004) 15:647-653.
Hunter, MJ. et al. *J. Am. Chem. Soc.* (1962) 84:3491-3508.
Hunter, MJ. et al. *In Methods in Enzymology—Enzyme Structure Part B*; Hirs CHW et al, Eds; Academic Press: New York and London, 1972; vol. XXV, pp. 585-596.
Ji et al. *J. Proteome Research* (2005) 4:734-742.

(Continued)

Primary Examiner — Joseph Kosack
(74) *Attorney, Agent, or Firm* — Lathrop & Gage LLP

(57) ABSTRACT

Relative quantification of metabolites by Electrospray Ionization Mass Spectrometry (ESI-MS) requiring a mechanism for simultaneous analysis of multiple analytes in two or more samples. Labeling reagents that are reactive to particular compound classes and differ only in their isotopic compositions facilitate relative quantification. Heavy and light isotopic forms of methylacetimidate were synthesized and used as labeling reagents for quantification of amine-containing molecules. Heavy and light isotopic forms of formaldehyde and cholamine were also synthesized and used independently as labeling reagents for quantification of amine-containing and carboxylic acid-containing molecules, such as found in biological samples. The labeled end-products are positively charged under normal acidic conditions involving conventional Liquid Chromatography Mass Spectrometry (LC/MS) applications. Labeled primary and secondary amine and carboxylic acid end-products generated higher signals concerning mass-spectra than pre-cursor molecules and improved sensitivity. Improved accuracy concerning relative quantification was demonstrated by mixing heavy and light labeled *Arabidopsis* extracts in different ratios.

36 Claims, 27 Drawing Sheets

(56) References Cited

OTHER PUBLICATIONS

Ji et al. *J. Proteome Research* (2005) 4:2099-2108.
Kita, Y. et al. *Anal Biochem.* (2005) 342; 134-143.
Koek, MM. et al. *Anal. Chem.* (2006) 78:1272-1281.
Lafaye, A. et al. *Anal Chem.* (2005) 77:2026-2033.
Lockhart, DJ et al. *Nature Biotechnol* (1996) 14:1675-1680.
Mashego, MR. *Biotechnol. Bioeng.* (2004) 85:620-628.
Peters, K. et al. *Ann. Rev. Biochem.* (1977) 46:523-551.
Rabaglia, ME. et al. *Am. J. Physi. Endocrinol.* Metab. (2005) 289:E218-E224.
Rochfort, SJ. *Nat.Prod.* (2005) 658:1813-1820.
Rottmann, A. et al. *J. Synthesis* (1997) 313-327.
Schena, M. et al. *Science* (1995) 270:467-470.
Shadforth et al. *BMC Genomics* (2005) 6:145.
Shorteed et al. *Anal. Chem.* (2006) 78:6398-6403.
Sterner, JL. et al. *Mass Spectrom.* (2000) 35:385-391.
Sumner, LW et al. *Phytochemistry* (2003) 62:817-836.
Tang L. et al. *Anal Chem.* (1993) 65:3654-3668.
Tolstikov, VV et al. *Anal Biochem* (2002) 301:298-307.
Vaidyanathan, S. et al. *Anal. Chem.* (2001) 73:4134-4144.
Von Roepenack-Lahaye E. et al. *Plant Physiol.* (2004) 134:548-559.
Wang, WX et al. *Anal. Chem.* (2003) 75:4818-4826.
Want, EJ et al. *Anal Chem.* (2006) 743:752.
Weckwerth, W. et al. *Curr. Opin. Biotechnol.* (2002) 13:156-160.
Wu L. et al. *Anal. Biochem.* (2005) 336;164-171.
Yi et al. *Proteomics* (2005) 5:380-387.
Zhang et al. *Rapid Commun. Mass Spectrom.* (2002) 16:2325-2332.
Zhang et al. *Tetrahedron Letters* (2005) 46:2087-2091.

\* cited by examiner

IONIZABLE ISOTOPIC LABELING REAGENTS FOR RELATIVE QUANTIFICATION BY MASS SPECTROMETRY

CROSS-REFERENCE TO RELATED APPLICATIONS

This application is a divisional of U.S. application Ser. No. 11/726,307, filed on Mar. 21, 2007, which claims the benefit of U.S. Provisional Application No. 60/784,400 filed Mar. 21, 2006, all of which are incorporated herein by reference in their entireties to the extent not inconsistent herewith.

STATEMENT REGARDING FEDERALLY SPONSORED RESEARCH OR DEVELOPMENT

This invention was made with government support under HG002298, DK070297, and HV28182 awarded by the National Institutes of Health and 0203892 awarded by National Science Foundation. The government has certain rights in the invention.

FIELD OF THE INVENTION

The present invention is related to the field of ionizable isotopic labeling, or derivatizing, reagents for the relative quantification of amine- and carboxylic acid-containing molecules (such as biological metabolite molecules).

BACKGROUND OF THE INVENTION

Comprehensive analysis of small molecule metabolites in complex biological systems can provide important insight that may otherwise be difficult or impossible using targeted analysis of specific compounds. Conventional analysis of metabolites using Gas Chromatography and Mass Spectrometry (GC/MS) involves differentiating small molecules having labels, or tags, whereby the label lowers the vapor pressure of small target molecules to enhance transmission through the analytical system. Increasingly, Liquid Chromatography/Mass Spectrometry (LC/MS) is being used for metabolic analysis due in part to widespread availability and compatibility with biological samples. Currently, however, a need exists for comprehensive relative quantification of metabolites using LC/MS analysis techniques.

Comprehensive analyses of small molecule metabolites in complex systems may also provide important insight into biological systems. The desired outcomes of such metabolomics studies are the detection, identification, and precise quantification of a large number of metabolites with diverse chemical structures and broad concentration ranges. Much work has focused on identifying as many metabolites as possible and many NMR and mass spectrometric techniques have been employed. (Birkemeyer C et al., *Trends Biotechnol.* 2005, 23, 28-33; Rochfort S J, *Nat. Prod.* 2005, 68, 1813-1820; Sumner L W et al., *Phytochemistry* 2003, 62, 817-836; and Weckwerth W et al., *Curr. Opin. Biotechnol.* 2002, 13, 156-160).

Mass spectrometry provides excellent sensitivity and good identification capabilities, but special considerations are necessary to deal with the complexity of metabolomic samples and with quantification. The coupling of a separation technique to mass spectrometry is an important common method of dealing with the sample complexity issue. Direct analysis of metabolic extracts by mass spectrometry has been reported. (Aharoni A et al., *Omics* 2002, 6, 217-234; and Vaidyanathan S et al., *Anal. Chem.* 2001, 73, 4134-4144). GC-MS has been used extensively for profiling non-polar compounds as well as some polar ones (i.e., after derivatization) in order to increase volatility. (Fiehn O et al., *Nature Biotechnol.* 2000, 18, 1157-1161; and Koek M M et al., *Anal. Chem.* 2006, 78, 1272-1281).

Increasingly, LC-MS is being used for metabolomic analyses owing to its compatibility with a wide-range of analytes in biological samples. (Dalluge L L et al., *Chromatogr. A* 2004, 1043, 3-7; Lafaye A et al., *Anal. Chem.* 2005, 77, 2026-2033; Tolstikov V V et al., *Anal. Biochem.* 2002, 301, 298-307; von Roepenack-Lahaye E et al., *Plant Physiol.* 2004, 134, 548-559; Wang W X et al., *Anal. Chem.* 2003, 75, 4818-4826; Want E J et al., *Anal. Chem.* 2006, 78, 743-752; and, Wu L et al., *Anal. Biochem.* 2005, 336, 164-171).

Another important consideration in mass spectrometric analysis is quantification. Various strategies have been employed for quantitative LC-MS of metabolomic samples. Absolute quantification of an analyte relies upon addition of an internal standard differing only in its isotopic form. That method has been employed in many studies that target a particular compound or a small set of metabolites. (Kita Y et al., *Anal. Biochem.* 2005, 342, 134-143; and, Rabaglia M E et al., *Am. J. Physi. Endocrinol. Metab.* 2005, 289, E218-E224).

However, it is impractical to add an isotopic standard for every compound when performing more comprehensive metabolic profiling. Relative quantification between samples is more amenable to analyzing broad classes of compounds, and it often provides very useful biological information. Some researchers have turned to in vivo labeling of metabolites with 2H, 13C, or 15N, and comparing the labeled sample with a control sample that has natural isotopic abundances. (Birkemeyer C et al., *Trends Biotechnol.* 2005, 23, 28-33; Lafaye A et al., *Anal. Chem.* 2005, 77, 2026-2033; Wu L et al., *Anal. Biochem.* 2005, 336, 164-171; and, Mashego M R et al., *Biotechnol. Bioeng.* 2004, 85, 620-628). That strategy works fairly well for certain organisms such as yeast, bacteria, and some plants, but uniform incorporation of these isotopes into all metabolites for animals is quite difficult/expensive or impossible (e.g., metabolites from humans).

Consequently, some quantitative metabolic profiling has been performed without an isotopic standard. (von Roepenack-Lahaye E et al., *Plant Physiol.* 2004, 134, 548-559; Wang W X et al., *Anal. Chem.* 2003, 75, 4818-4826; and, Want E J et al., *Anal. Chem.* 2006, 78, 743-752). Quantification in this manner is less precise, but adequate reproducibility has been obtained in many cases despite the well-known problem of ion-suppression during electrospray ionization. (Choi B K et al., *Chromatogr. A* 2001, 907, 337-342; Constantopoulos T L et al., *Am. Soc. Mass Spectrom.* 1999, 10, 625-634; Sterner J L et al., *Mass Spectrom.* 2000, 35, 385-391; and, Tang L et al., *Anal. Chem.* 1993, 65, 3654-3668).

Another strategy for relative quantification is chemical labeling, which has proven to be useful for quantification in genomics (e.g., two color fluorescent dye labeling)(Lockhart D J et al., *Nature Biotechnol.* 1996, 14, 1675-1680; and, Schena M et al., *Science* 1995, 270, 467-470) and proteomics (e.g., isotope-coded affinity tags)(Aebersold R et al., *Nature* 2003, 422, 198-207; Gygi S P et al., *Nature Biotechnol.* 1999, 17, 994-999). Relative quantification by labeling has seen limited use for metabolomics due in part to the lack of a single functional group present in all metabolites to act as the target for the labeling chemistry.

Isotopic labeling reagents have been employed for relative quantification of peptides and proteins. Cys residues of a protein have been reduced and then alkylated with an isotope (heavy or light) containing affinity tag. Tagged whole proteins were then digested with trypsin, which produces cleavage products c-terminal to Lys and Arg resulting in peptide products of 10-15 amino acids in length. Product peptides originally containing one or more Cys residues would have been tagged whereas those without a Cys residue would not. Light and heavy tagged samples were mixed, and an affinity capture procedure extracted labeled product peptides, which were subsequently analyzed by LC-MS. The ratio between heavy- and light-peptide products yields the relative amounts of each constituent. The peptide sequence is determined in the same MS experiment by fragmentation.

One drawback of this approach is that only peptides containing a Cys residue are labeled. Another drawback of this approach is that the labeling reagent can introduce a chromatographic shift between the light- and heavy-labeled products, which hinders quantification. Another drawback of this approach is that the tag does not increase the charge state of the labeled product in ESI-MS. Another drawback of this approach is that it does not block carboxylic acid functional groups.

One drawback of known labeling reagents is that many do not produce ionizable end-products. For example, known target molecules having ionizable functional groups thereon are converted to non-ionizable functional groups upon reaction with the labeling reagent. Another drawback of known labeling reagents is the need for reaction clean-up. Other known labeling reagents are disadvantaged due to the large size/mass of the tag residue relative to the size/mass of the biological target material, which adversely impacts chromatographic separation. Insufficient chromatographic separation is problematic because labeled target materials would be difficult or impossible to be adequately quantified by mass spectrometry. Another drawback of known labeling reagents is an inability to react with carboxylic acids. Still other labeling reagents locate deuterium atoms on a hydrophobic residue, which can interfere or prevent heavy- and light-labeled end-products from co-eluting. A need also exists for reagents that are compatible with labeling of multiple different functional groups.

The instant invention overcomes these and other disadvantages by providing ionizable, isotopic labeling reagents and labeling reaction products for relative quantification using mass spectrometry.

SUMMARY OF THE INVENTION

Figure 1:
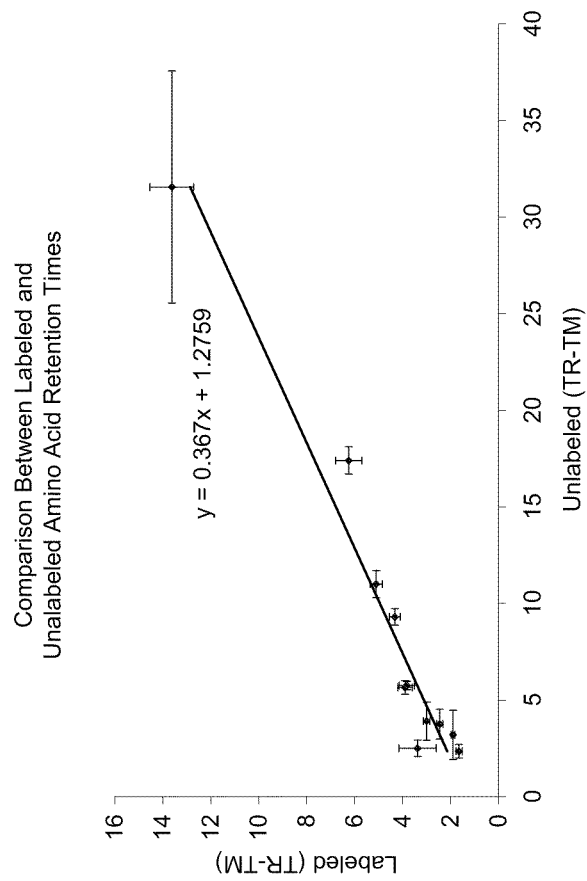
FIG. 1 is a graphical illustration of a comparison between retention, or elution, times for qty. 11 representative labeled and unlabeled amino acids using the instant methylacetimidate reagents whereby the order of elution for the unlabeled amino acids (shortest to longest) was tryptophan, phenylalanine, leucine, tyrosine, valine, proline, alanine, glutamine, asparagine, glutamic acid, and aspartic acid, and whereby the order of elution for the labeled amino acids was tryptophan, leucine, tyrosine, valine, phenylalanine, alanine, proline, glutamine, asparagine, glutamic acid, and aspartic acid, whereby the data shows that labeling increases hydrophobicity and reduces retention time, and whereby TR is retention time (min.) and TM is the dead time for unretained compounds to elute (min.).

One aspect of the invention includes labeling reagents having tag residues that are approximately equal to or preferably smaller in size and/or mass than the residue of the target molecules. In the art, the labeling agents of the present invention are also referred to as derivatizing and tag reagents. As used herein, target molecules or target analytes for labeling include biological metabolites, peptides, proteins and the like.

Another aspect of the invention includes labeling reagents that have a fixed-charge quaternary amine that is capable of reacting with target molecules to increase the charge state.

Another aspect of the invention includes labeling reagents that have a fixed-charge quaternary amine that is capable of reacting with carboxylic acid functional groups whereby the labeling reagent blocks the carboxylic acid functional groups.

Another aspect of the invention includes labeling reagents that have a fixed-charge quaternary amine that is capable of reacting with target molecules to increase the charge state to improve ETD analysis of peptides and proteins.

Another aspect of the invention includes labeling reagents that when reacted with target molecules convert negatively-charged, neutral or positively-charged target molecules into positively-charged end-products, which is desirable for mass spectrometry analysis.

Another aspect of the invention includes neutral uncharged labeling reagents that when reacted with target molecules produce ionizable end-products.

Another aspect of the invention includes labeling reagents having a fixed-charge quaternary amine that is suitable for reacting with target molecules to produce ionizable end-products.

Another aspect of the invention includes labeling reagents that improve mass spectrometry quantitative analysis by enhancing sensitivity through/by increasing $pK_a$ and/or hydrophobicity.

Another aspect of the invention includes labeling reagents that are compatible with multi-functional group labeling. Preferably, one or more first labeling reagents may be used in conjunction with one or more second labeling reagents to label target molecules having both amine and carboxylic acid groups. Preferably, an analysis is performed from a single LC/MS experimental run in positive or negative mode, whereby the labeling reagents produce end-products (containing the target molecule) that can be run in a single positive or negative ion mode LC/MS experimental run.

Another aspect of the invention includes labeling reagents that produce characteristic mass shifts useable for target molecule identification. For example, a 2 Dalton shift can indicate the presence of an amine, a 3, 6 or 9 Dalton shift would indicate the presence of a carboxylic acid, and a 5, 8 or 11 Dalton shift would indicate the presence of an amine and a carboxylic acid group. Other characteristic mass shifts are contemplated which are determined by the number of amine or carboxylic acid groups present in a given target molecule.

Another aspect of the invention is a group of aldehydes (containing stable heavy isotopes) suitable for reacting with a diamine to make a secondary or tertiary amine and further reacting with various alkyl halides to form a quaternary amine labeling reagent suitable for reacting with carboxylic acid groups of a target molecule for use in mass spectrometry comprising:

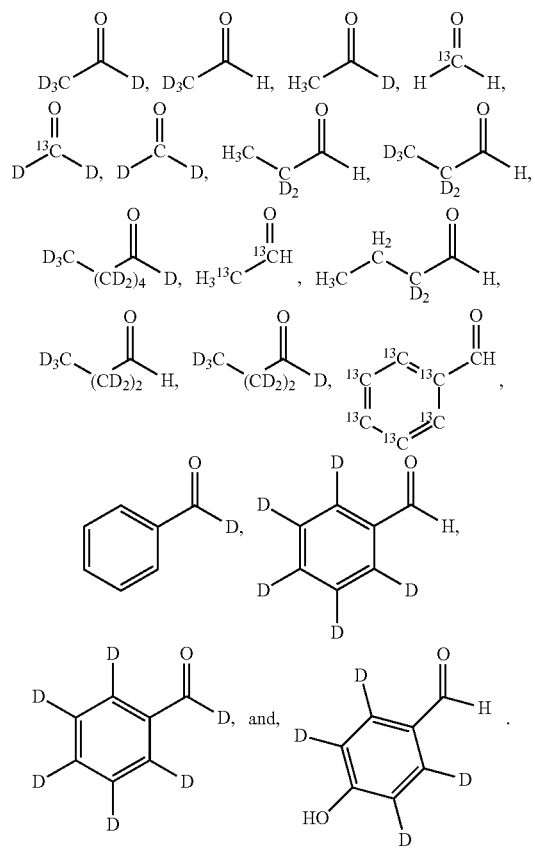

Another aspect of the invention is a group of aldehydes (containing stable heavy isotopes) suitable for reacting with primary and secondary amine groups of a target molecule for use in mass spectrometry comprising:

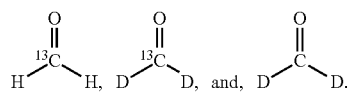

Another aspect of the invention is a group of ketones (containing stable heavy isotopes) suitable for reacting with diamines to make secondary amines that further react with various alkyl halides to form quaternary amine labeling reagents suitable for reacting with carboxylic acid groups of a target molecule for use in mass spectrometry comprising:

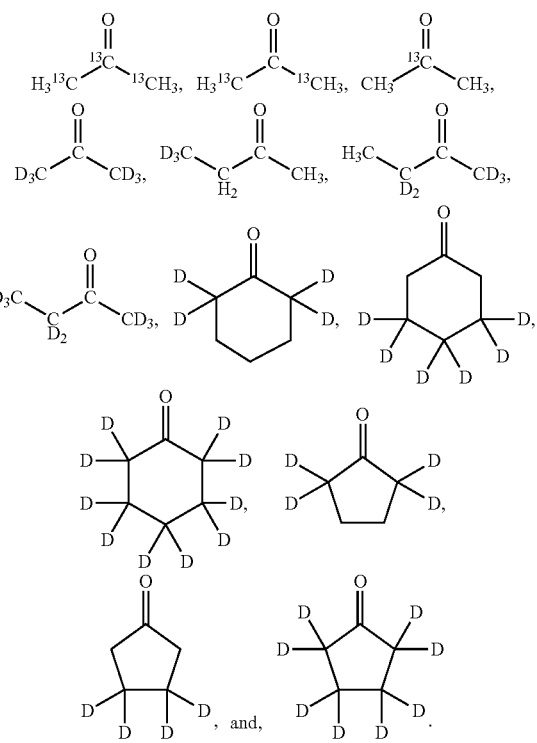

Another aspect of the invention is a group of alkyl halides (containing stable heavy isotopes) suitable for reacting with a diamine to make a quaternary amine labeling reagent suitable for reacting with carboxylic acid groups of a target molecule for use in mass spectrometry comprising:

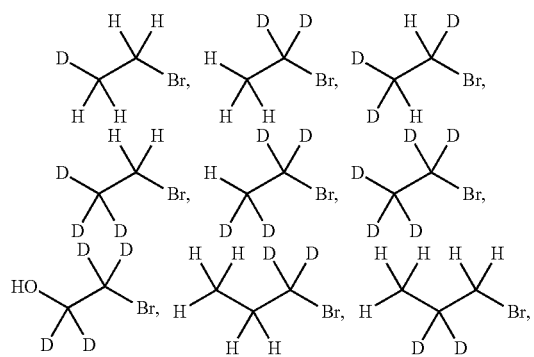

-continued

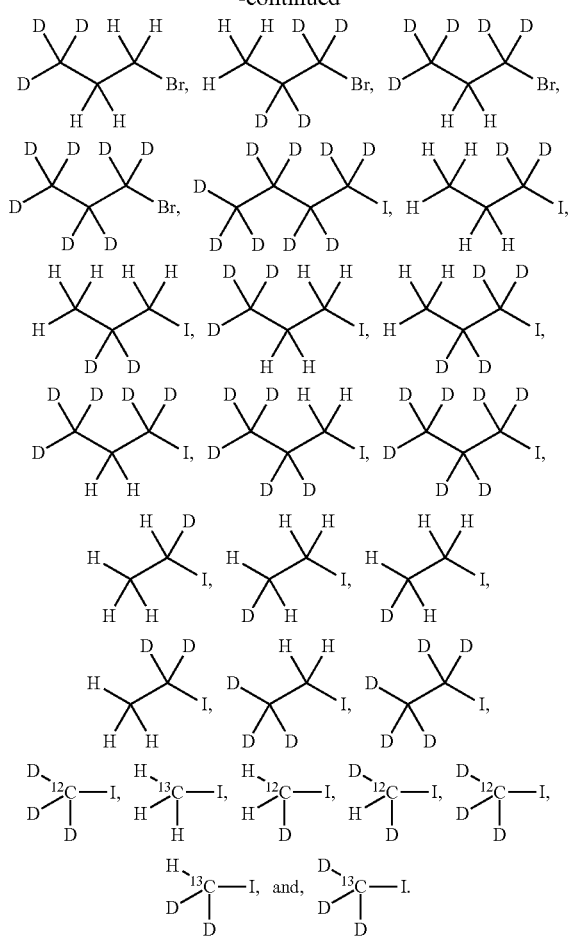

Another aspect of the invention is a group of nitriles (containing stable heavy isotopes) suitable for reacting with a suitable alcohol and a suitable acid to make an imidoester labeling reagent which is suitable for reacting with primary and secondary amines in a target molecule for use in mass spectrometry comprising:

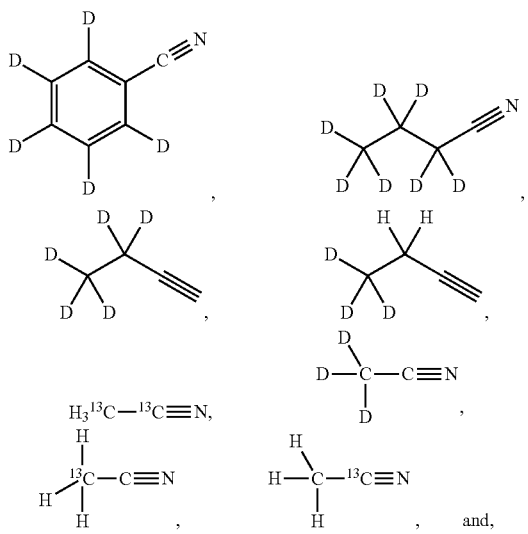

-continued

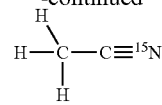

Another aspect of the invention is a heavy imidoester compound for use as a labeling reagent in mass spectrometry according to the formula:

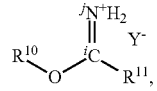

wherein any number of hydrogens in the compound are $^1H$ or D, wherein D is deuterium, wherein $R^{10}$—O is a suitable leaving group, wherein $R^{11}$ is a member selected from the group consisting of $C_1$-$C_4$ branched or linear, saturated or

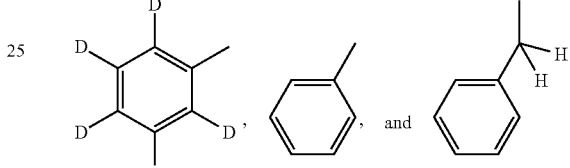

unsaturated alkyl containing any number of $^1H$ and/or D, wherein any number of carbons in $R^{11}$ are $^{13}C$, wherein j=14 or 15, wherein i=12 or 13, and, wherein r is a suitable anion.

In an exemplary embodiment of the heavy imidoester compound, $R^{11}$ is a $C_1$-$C_4$ branched or linear, saturated or unsaturated alkyl, each carbon in $R^{11}$ is $^{13}C$, and $R^{11}$ contains only hydrogens.

In another exemplary embodiment of the heavy imidoester compound, $R^{11}$ is a $C_1$-$C_4$ branched or linear, saturated or unsaturated alkyl, and each carbon in $R^{11}$ is $^{12}C$.

In another exemplary embodiment of the heavy imidoester compound, $R^{11}$ is a $C_2$-$C_4$ branched or linear, saturated or unsaturated alkyl, each carbon in $R^{11}$ is $^{13}C$, and $R^{11}$ contains only hydrogens.

In another exemplary embodiment of the heavy imidoester compound, $R^{11}$ is a member selected from the group consisting of $^{13}CH_3$ and $^{12}CH_3$.

In another exemplary embodiment of the heavy imidoester compound, $R^{11}$ is $^{13}CH_3$.

In another exemplary embodiment of the heavy imidoester compound, $R^{10}$ is a member selected from the group consisting of $C_1$-$C_8$ linear or branched, saturated or unsaturated alkyl; aryl and a suitable solid support.

Another aspect of the invention is an imidoester kit suitable for reacting with primary or secondary amine groups in target molecules for use in mass spectrometry comprising any one of the heavy imidoester compounds set forth above, and, a light imidoester compound structurally identical to the heavy imidoester compound with the proviso that the light imidoester compound is at least around 1 Dalton less in weight than the heavy imidoester compound.

In another exemplary embodiment of the heavy imidoester kit, the light imidoester compound is at least around 2 Daltons less in weight than the heavy imidoester compound.

Another aspect of the invention is a method of labeling target molecules containing primary or secondary amine groups for use in mass spectrometry comprising providing one or more target molecules, and, reacting the target molecules with any one of the imidoester kits set forth above.

In an exemplary embodiment, the method further includes introducing the target molecules into an RF ion trap, introducing gas-phase anions into the RF ion trap, mixing gas-phase anions and multiply-charged target molecule cations so as to facilitate electron transfer from the anions to the multiply-charged target molecule cations inducing the production of electron transfer dissociation product ions, terminating the reactions by physically separating the remaining gas-phase anions from the electron transfer product cations, and, conducting m/z analysis of cations remaining in the trap, wherein the target molecules are peptides or proteins.

Another aspect of the invention is a heavy quaternary amine compound for use as a labeling reagent in mass spectrometry according to the formula:

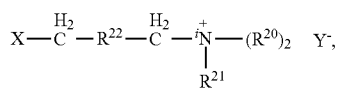

wherein i=14 or 15, wherein any number of hydrogens in the compound are $^1H$ or D, wherein D is deuterium, wherein any number of carbons in the compound are $^{12}C$ or $^{13}C$, wherein any number of oxygens in the compound are $^{16}O$ or $^{18}O$, wherein any number of nitrogens in the compound are $^{14}N$ or $^{15}N$, wherein X is a suitable primary or secondary amine group having $^{14}N$ or $^{15}N$, wherein $Y^-$ is a suitable anion, wherein $R^{22}$ is a member selected from the group consisting of a bond; $C_1$-$C_{30}$ linear or branched, saturated or unsaturated alkylene; aryl, aliphatic ring, oxygen-containing aliphatic ring, halogenated aryl, O, $C_1$-$C_{12}$ linear or branched ether, $C_1$ to $C_{12}$ linear or branched polyether, $C_1$-$C_{28}$ branched or linear ester, and, $C_1$-$C_{28}$ branched or linear amide, wherein $R^{20}$ and $R^{21}$ are each independently a member selected from the group consisting of $C_1$-$C_4$ branched or linear, saturated or unsaturated alkyl containing any number of $^1H$ and/or D;

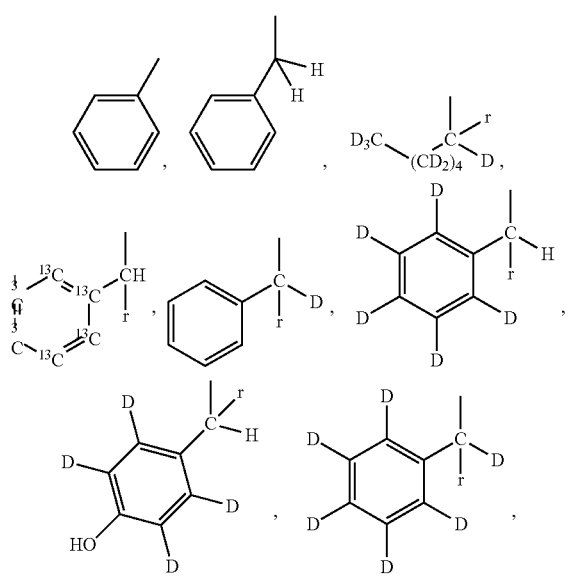

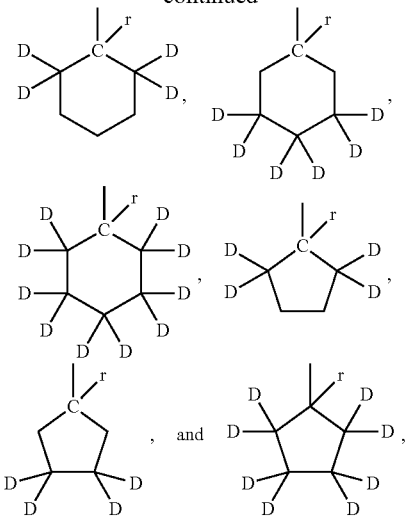

wherein r=$^1H$ or D.

In an exemplary embodiment of the heavy quaternary amine compound, $R^{20}$ and $R^{21}$ are each independently $C_1$-$C_4$ branched or linear, saturated or unsaturated alkyl, and each carbon in $R^{20}$ and $R^{21}$ is $^{13}C$.

In an exemplary embodiment of the heavy quaternary amine compound, $R^{20}$ and $R^{21}$ are each independently $C_1$-$C_2$ branched or linear, saturated or unsaturated alkyl, each carbon in $R^{20}$ is $^{12}C$, and each carbon in $R^{21}$ is $^{13}C$.

In an exemplary embodiment of the heavy quaternary amine compound, $R^{20}$ and $R^{21}$ are each independently $C_1$-$C_2$ branched or linear, saturated or unsaturated alkyl, each carbon in $R^{20}$ is $^{13}C$, and each carbon in $R^{21}$ is $^{12}C$.

In an exemplary embodiment of the heavy quaternary amine compound, $R^{20}$ and $R^{21}$ are each independently $C_1$-$C_4$ branched or linear, saturated or unsaturated alkyl, each carbon in $R^{20}$ is $^{12}C$, and each carbon in $R^{21}$ is $^{13}C$.

In an exemplary embodiment of the heavy quaternary amine compound, $R^{20}$ and $R^{21}$ are each independently $C_1$-$C_4$ branched or linear, saturated or unsaturated alkyl, each carbon in $R^{20}$ is $^{13}C$, and each carbon in $R^{21}$ is $^{12}C$.

In an exemplary embodiment of the heavy quaternary amine compound, $R^{20}$ and $R^{21}$ are each independently $C_1$-$C_2$ branched or linear, saturated or unsaturated alkyl, and each carbon in $R^{20}$ and $R^{21}$ is $^{13}C$.

In an exemplary embodiment of the heavy quaternary amine compound, $R^{20}$ and $R^{21}$ are each a member selected from the group consisting of $^{13}CH_3$ and $^{13}CD_3$.

In an exemplary embodiment of any one of the heavy quaternary amine compounds, $R^{20}$ and $R^{21}$ contain only hydrogens.

In an exemplary embodiment of the heavy quaternary amine compound, $R^{22}$ is a member selected from the group consisting of a bond, $^{12}C_1$-$^{12}C_2$ alkylene, and $^{13}C_1$-$^{13}C_2$ alkylene, and $R^{22}$ contains only hydrogens.

In an exemplary embodiment of the heavy quaternary amine compound, $R^{22}$ is a member selected from the group consisting of a bond, $^{12}CH_2$ and ($^{12}CH_2$)$_2$, X is $^{14}NH_2$, i=14, and $R^{20}$ and $R^{21}$ are $^{12}CD_3$.

Another aspect of the invention is a quaternary amine kit suitable for reacting with carboxylic acid groups in target molecules for use in mass spectrometry comprising any one of the heavy quaternary amine compounds set forth above, and, a light quaternary amine compound structurally identical to the heavy quaternary amine compound with the proviso that the light quaternary amine compound is at least around 1 Dalton less in weight than the heavy quaternary amine compound.

In an exemplary embodiment of the quaternary amine kit, the light quaternary amine compound is at least around 2 Daltons less in weight than the heavy quaternary amine compound.

Another aspect of the invention is a method of labeling target molecules containing carboxylic acid groups for use in mass spectrometry comprising providing one or more target molecules, and, reacting the target molecules with any one of the quaternary amine kits set forth above. In any exemplary embodiment, the method further includes introducing the target molecules into an RF ion trap, introducing gas-phase anions into the RF ion trap, mixing gas-phase anions and multiply-charged target molecule cations so as to facilitate electron transfer from the anions to the multiply-charged target molecule cations inducing the production of electron transfer dissociation product ions, terminating the reactions by physically separating the remaining gas-phase anions from the electron transfer product cations, and, conducting m/z analysis of cations remaining in the trap, wherein the charge state of the labeled target molecules is increased due to the labeling, and, wherein the target molecules are peptides or proteins. In another exemplary embodiment, the method further includes purifying the labeled target molecules with immobilized metal affinity chromatography (IMAC), wherein the target molecules are phosphopeptides or phosphoproteins. In an exemplary embodiment of the ETD method, the heavy quaternary amine compound is $\{H_2N(CH_2)_4N^+(CD_3)_3\}Y^-$, and the light quaternary amine compound is $\{H_2N(CH_2)_4N^+(CH_3)_3\}Y^+$.

Another aspect of the invention is an aldehyde kit suitable for reacting with primary and/or secondary amine groups in target molecules for use in mass spectrometry comprising a heavy aldehyde compound suitable for reacting with primary or secondary amine groups in a target molecule for use in mass spectrometry according to the formula:

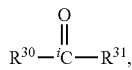

wherein i=12 or 13, wherein $R^{30}$ is a member selected from the group consisting of $^1H$ and D, wherein D is deuterium, wherein $R^{31}$ is a member selected from the group consisting of H, D; $C_1$-$C_{30}$ linear or branched, saturated or unsaturated alkyl; aryl, halogen-substituted aryl, aliphatic ring, oxygen-containing aliphatic ring, $C_1$-$C_{12}$ linear or branched ether, $C_1$-$C_{12}$ linear or branched polyether, $C_1$-$C_{28}$ linear or branched amide, and, $C_1$-$C_{28}$ linear or branched ester, wherein any number of hydrogens in $R^{31}$ are $^1H$ or D, wherein any number of carbons in $R^{31}$ are $^{12}C$ or $^{13}C$, wherein any number of nitrogens in $R^{31}$ are $^{14}N$ or $^{15}N$, and, wherein any number of oxygens in $R^{31}$ are $^{16}O$ or $^{18}O$, and, a light aldehyde compound structurally identical to the heavy aldehyde compound with the proviso that the light aldehyde compound is at least around 1 Dalton less in weight than the heavy aldehyde compound.

In an exemplary embodiment of the aldehyde kit, $R^{31}$ is a member selected from the group consisting of $^1H$, D, methyl, ethyl and aryl.

In an exemplary embodiment of the aldehyde kit, $R^{31}$ is a member selected from the group consisting of $^1H$ and D, and the heavy aldehyde compound is suitable for reacting with primary and secondary amine groups in target molecules for use in mass spectrometry.

In an exemplary embodiment of the aldehyde kit, the light aldehyde compound is at least around 2 Daltons less in weight than the heavy aldehyde compound.

Another aspect of the invention is a method of labeling target molecules containing primary and/or secondary amine groups for use in mass spectrometry comprising providing one or more target molecules, and, reacting the target molecules with any one of the aldehyde kits wet forth above. In an exemplary embodiment, the method further includes introducing the target molecules into an RF ion trap, introducing gas-phase anions into the RF ion trap, mixing gas-phase anions and multiply-charged target molecule cations so as to facilitate electron transfer from the anions to the multiply-charged target molecule cations inducing the production of electron transfer dissociation product ions, terminating the reactions by physically separating the remaining gas-phase anions from the electron transfer product cations, and, conducting m/z analysis of cations remaining in the trap, wherein the labeled target molecules is increased due to the labeling, and, wherein the target molecules are peptides or proteins.

Another aspect of the invention is a ketone kit suitable for reacting with primary amine groups in target molecules for use in mass spectrometry comprising a heavy ketone compound comprising:

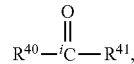

wherein i=12 or 13, wherein $R^{40}$ and $R^{41}$ are each independently a member selected from the group consisting of $C_1$-$C_{30}$ linear or branched, saturated or unsaturated alkyl; aryl, halogen-substituted aryl, aliphatic ring, oxygen-containing aliphatic ring, $C_1$-$C_{12}$ linear or branched ether, $C_1$-$C_{12}$ linear or branched polyether, $C_1$-$C_{28}$ linear or branched amide, and, $C_1$-$C_{28}$ linear or branched ester, wherein any number of carbons in $R^{40}$ and $R^{41}$ are $^{12}C$ or $^{13}C$, wherein any number of hydrogens in $R^{40}$ and $R^{41}$ are $^1H$ or D, wherein D is deuterium, wherein any number of nitrogens in $R^{40}$ and $R^{41}$ are $^{14}N$ or $^{15}N$, and, wherein any number of oxygens in $R^{40}$ and $R^{41}$ are $^{16}O$ or $^{18}O$, and, a light ketone compound structurally identical to the heavy ketone compound with the proviso that the light ketone compound is at least around 1 Dalton less in weight than the heavy ketone compound.

In an exemplary embodiment of the ketone kit, the light ketone compound is at least around 2 Dalton less in weight than the heavy ketone compound.

Another aspect of the invention is a method of labeling target molecules containing primary amine groups for use in mass spectrometry comprising providing one or more target molecules, and, reacting the target molecules with any one of the ketone kits set forth above. In an exemplary embodiment, the method further includes introducing the target molecules into an RF ion trap, introducing gas-phase anions into the RF ion trap, mixing gas-phase anions and multiply-charged target molecule cations so as to facilitate electron transfer from the anions to the multiply-charged target molecule cations inducing the production of electron transfer dissociation product ions, terminating the reactions by physically separating the remaining gas-phase anions from the electron transfer product cations, and, conducting m/z analysis of cations remaining in the trap, wherein the target molecules are peptides or proteins.

These and other individual features and advantages of the invention are described in or are apparent from the following detailed description. The features and advantages may be separately incorporated in various exemplary embodiments of systems and methods set forth herein.

DETAILED DESCRIPTION OF THE INVENTION

Metabolomics involves identifying and quantifying the small molecules present in biological samples. The two most common analysis techniques are NMR and chromatography coupled to mass spectrometry (e.g. GC-MS and LC-MS). Mass spectrometry offers much greater sensitivity thereby providing analysis of numerous low-abundance metabolites, but its quantitative precision is inherently poorer than NMR. Relative quantification of metabolites between two or more samples helps researchers understand biological systems by unveiling interesting differences and by testing hypotheses. Many such metabolomic studies use multiple retention-time standards and sophisticated data analysis software to achieve reasonable precision for comparing samples run separately. An alternative strategy for quantification of metabolites employs isotopic labeling reagents that react with compounds containing a particular functional group.

Figure 25:
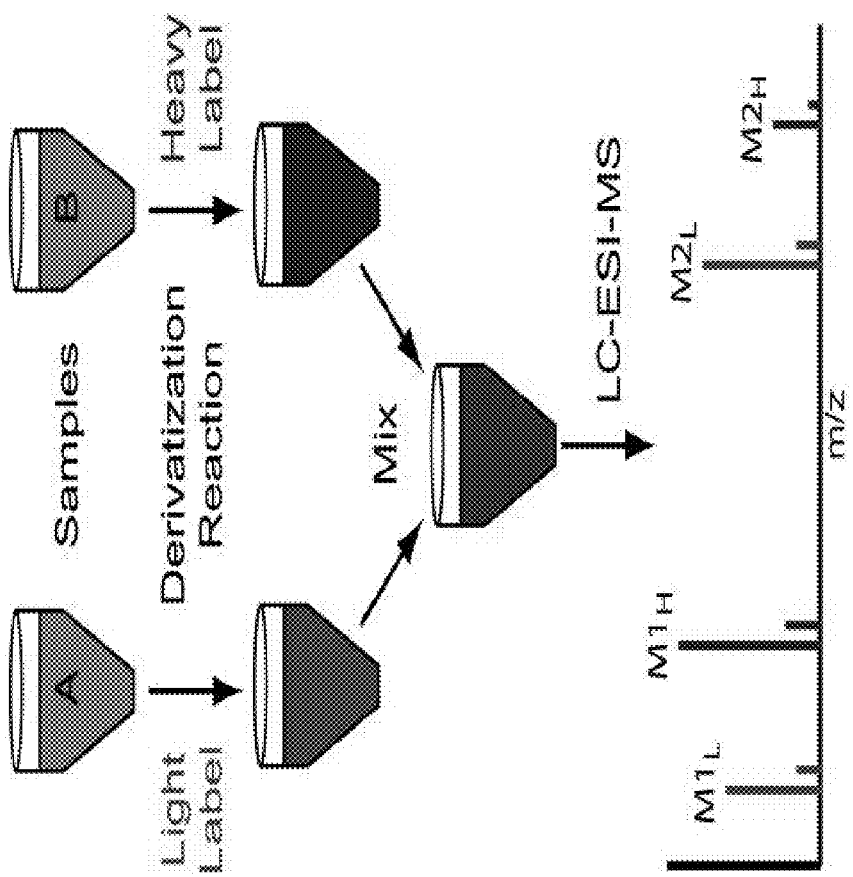
FIG. 25 is a schematic illustration showing relative quantification by isotopic labeling, whereby biomolecules containing certain functional groups are derivatized with light- and heavy-isotopic tags prior to mixing the two samples and conducting LC-MS analysis, whereby the ratio of mass spectral peak intensities for each biomolecule (e.g., $M1_L/M1_H$) provides relative quantification between samples A and B.

As shown in FIG. 25, each sample is reacted with a reagent that differs only in its isotopic kit, thereby creating heavy and light versions of derivatized metabolites, which are easily distinguished by MS. Labeled metabolites co-elute from the LC-column and appear in the mass spectrum as pairs of peaks with a mass-shift equal to the difference in mass of the two isotopic labels. The ratio of peak intensities for each pair yields the relative concentration of each metabolite between the two samples.

Isotopic labeling has a number of advantages. It improves the precision of relative quantification by minimizing or negating errors associated with run-to-run irreproducibility. Such errors can arise from variations in mass spectrometric detection sensitivity, such as those caused by ionization suppression in electrospray, or from retention time differences between runs. The isotopic pair of labeled compounds co-elute within a single run. Therefore, they have identical retention times and are electrosprayed from identical solution conditions. A second benefit of utilizing a derivatization reagent is that it can help identify a metabolite by indicating the presence of a certain functional group, i.e., the one targeted by the reagent. Furthermore, well-designed labeling reagents can improve chromatographic separation and enhance detection sensitivity.

As regards the instant invention, various types of mass spectrometric analysis and "mass spectrometry" equipment thereof may be used with the instant labeling reagents. As used herein, "mass spectrometry" includes, but is not limited to, the equipment, analysis and processes thereof set forth below plus known variants thereof. For example, mass spectrometric analysis employing the instant reagents may occur through direct analysis of the mixture, such as infusion into a mass spectrometer's ionization source. The analysis may also be performed subsequent to a separation method and equipment thereof including, but not limited to, capillary electrophoresis, liquid chromatography in the form of reverse-phase liquid chromatography (RP-LC), hydrophilic interaction chromatography (HILIC), ion-exchange chromatography (IC), affinity chromatography, and the like. The ionization source for the mass spectrometric analysis includes, but is not limited to, electron impact (EI), chemical ionization (CI), atmospheric pressure chemical ionization (APCI), electrospray ionization (ESI), sonic spray ionization, matrix-assisted laser-desorption ionization (MALDI), or the like. Mass spectrometers suitable for separating and detecting the heavy- and light-labeled forms of the analyte end-products are suitable for use with the instant labeling reagents, such as, but not limited to, magnetic sector, double focusing, time-of-flight (TOF), linear ion trap, quadrupole (Q), triple quadrupole (QQQ), quadrupole time-of-flight (QTOF), ion-trap time-of-flight, Fourier transform spectrometers such as the ion cyclotron resonance (FT-ICR) and Orbitrap, and the like. Electrospray Ionization Mass Spectrometry (ESI-MS) may be used without prior LC separation. While the instant invention is exemplified using a ESI-TOF mass spectrometer and HILIC or reverse-phase C18 chromatography-based LC/MS runs, it is not limited to ESI-TOF. Other known mass spectrometry may be used as well. While chromatography cleanup may be exemplified, it is not a requirement of the instant invention. Additional exemplary chromatography methods that may be used in combination with the instant invention include C4, ion exchange and other known suitable methods.

The instant invention also includes using electron transfer dissociation (ETD) methods and systems in connection with the instant labeling reagents and various suitable mass spectrometry systems and method set forth above. U.S. Patent Application Publication No. US200510199804 (Pub. Date Sep. 15, 2005) to Hunt, Donald F. et al. entitled "Electron Transfer Dissociation for Biopolymer Sequence Analysis," (which is hereby incorporated herein by reference) discloses a new method for fragmenting ions in a mass spectrometer through use of electron transfer dissociation, and for performing sequence analysis of peptides and proteins by mass spectrometry, whereby in the case of peptides, the invention promotes fragmentation along the peptide backbone and makes it possible to deduce the amino acid sequence of the sample, including modified amino acid residues, through the use of a gas-phase reagent and an RF field device.

As used herein, "isotopically enriched", "isotopic", "isotopes", "isotope", "isotopically-light", "isotopically-heavy", "isotopically-different" and the like refer to compound(s) (e.g., labeling reagents, labeled target analytes and end-products, etc.) that have been enriched with one or more high mass, or heavy, isotopes (e.g., stable isotopes such as deuterium, $^{13}C$ and $^{15}N$), whereby a process has introduced one or more high mass isotopes into the relevant molecule/compound in excess of the natural isotopic abundance, and whereby compounds/molecules or fragments/moieties thereof having at least one high mass isotope therein may be referred to as being "heavy."

As used herein, "natural isotopic abundance" refers to the level (or distribution) of one or more isotopes found in a compound/molecule based upon the natural prevalence of an isotope or isotopes in nature. For example, a natural compound obtained from living plant matter typically contains about 1.08% $^{13}C$ relative to $^{12}C$.

As used herein, "label" refers to a moiety suitable for marking a target analyte molecule/compound for determination, whereby "label" is synonymous with the terms "tag", "mark", "marker" and other terms and phrases known in the art. For example, a labeled target analyte end-product may also be referred to as a tagged or marked analyte. The instant labeling reagents may also be used in solution or in combination with a solid support. Accordingly, the instant labeling reagents and labeled analytes/targets may exist in solution or deposited on (or linked to) a solid support.

Formaldehyde is also referred to as formalin when in solution.

The instant invention provides a powerful approach to relative quantification by mass spectrometry employing labeling reagents that target specific functional groups in molecules of interest. A quantitative comparison of two or more samples may be readily accomplished by using a chemically identical but isotopically distinct labeling reagent for each sample. The samples may then be combined, subjected to purification steps, and mass analyzed. Comparison of the signal intensities obtained from the isotopically labeled variants of the target analyte(s) provide quantitative information on their relative concentrations in the sample. Set forth herein is a description of the synthesis and use of heavy and light isotopic forms of methylacetimidate, formaldehyde and cholamine for the relative quantification of amine-containing and carboxylic acid-containing species. An important advantage of methylacetimidate as a labeling reagent is that the reaction product is positively charged and hydrophobicity is increased—both of which enhance electrospray ionization efficiency and increase detection sensitivity. Quantitative nature of the analysis is demonstrated in model metabolomics experiments in which heavy- and light-labeled *Arabidopsis* extracts were combined in different ratios. The labeling strategy also determined differences in the amounts of amine-containing metabolites for *Arabidopsis* seeds germinated under two different conditions.

Imidoesters have been used as specific reagents for modification of primary amino groups in proteins for several years. (Ludwig M L et al., *Am. Chem. Soc.* 1962, 84, 3491-3504; and, Peters K et al., *Ann. Rev. Biochem.* 1977, 46, 523-551). The reaction between a small molecule primary amine and the protonated form of methylacetimidate (an imidoester) forms an acetimidinium ion as shown in the reaction scheme below.

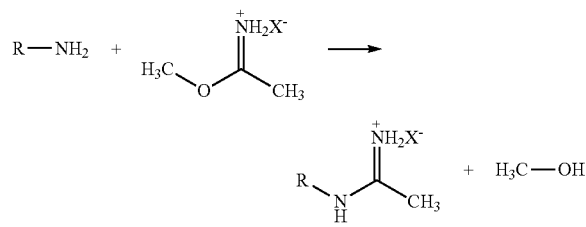

Methylacetimidate is an attractive labeling reagent for many reasons. The product of the labeling reaction has a very high pKa (~12.5), and so it is easily ionized under typical positive ion-mode LC-MS conditions. Ionizability of the analyte is preserved by labeling with an ionizable reagent in contrast to other labels that neutralize ionizable sites. (Hegeman A D et al., *J. Am. Soc. Mass. Spectrom.* 2004, 15, 647-653).

The mass-spectral signal produced by the labeled product is greater than for the unlabeled precursor molecule due in part to higher relative pKa and increased hydrophobicity. The relatively small size of the label, along with its chemical nature being similar to the amine it modifies, also minimizes its impact on the chromatographic separation. Proof that a given analyte is an amine is provided by the appearance of dual peaks in a mass spectrum separated by a characteristic mass-shift. Such mass-shifts are produced when two samples are labeled with heavy and light isotopic forms of the labeling reagent, followed by mixing and subsequent LC-MS analysis. The reaction conditions are such that no clean-up is required prior to introduction to the LC-MS system. Metabolites extracted from *Arabidopsis thaliana* plant tissue and seeds were labeled and analyzed to demonstrate the efficacy of methylacetimidate as a labeling reagent for the relative quantification of amines.

The methylacetimidate labeling reagent provides many advantages when used for relative quantification of primary and secondary amines. Products from the labeling reaction were generally more hydrophobic and had a higher pKa than unlabeled precursor molecules, which led to significantly enhanced mass-spectrometric sensitivity. Ionizability was preserved following labeling because the reaction product is an acetimidimium ion, which has a high pKa. The relatively small size of the label is also advantageous since the chromatographic separation remains related to the chemical nature of the parent amine, rather than being dominated by the labeling reagent. Characteristic mass shifts between the light- and heavy-labeled forms reveal the existence of an amine functionality in the parent molecules, which facilitates identification of unknown analytes. LC-MS analyses may be performed directly on the crude product mixture without need for a pre-run sample clean-up. Relative quantification of primary and secondary amines has been demonstrated in *Arabidopsis* seed extracts with an average relative standard deviation of 8%.

Imidoesters have been used as specific reagents for modification of primary amino groups in proteins. (Hunter M J et al., *J. Am. Chem. Soc.* 84:3491-3508, *Ann Rev Biochem.* 1977, 46:523-551). The reaction between a small molecule primary amine and the protonated form of methylacetimidate (the imidoester) forms an acetimidinium ion. In one embodiment of the invention, methylacetimidate labeled end-products have a very high $pK_a$ (~12.5), and the tag residue is easily ionized under typical positive ion-mode LC/MS conditions. The mass-spectral signal produced by the labeled end-product is greater than the unlabeled precursor molecule. Ionizability of the analyte is also preserved by labeling with an ionizable reagent.

The labeled residue is relatively small in size and mass, and its chemical nature is similar to the modified primary amine, which minimizes alteration of chromatographic separation. Labeling with the instant reagents generates a resultant peak shifted between heavy- and light-labeled target molecule end-products by 2.0067 Daltons in mass spectrum, which demonstrates that the labeled analyte is a primary or secondary amine. Characteristic isotopic shifts improve molecular identification by providing information concerning functional groups. Such information is very useful in identifying unknown compounds. Reaction conditions using the instant reagents also do not require clean-up prior to introduction to the LC/MS system. Metabolites extracted from the *Arabidopsis Thaliana* plant tissue and seeds were labeled and analyzed to demonstrate the usefulness of methylacetimidate as a labeling reagent for relative quantification of amines.

Synthesis of imidoesters. Imidoesters suitable for use as labeling reagents may be made from alcohols and nitriles. Liquid alcohol is first acidified by a suitable gas such as HCl. That is then treated with drop wise addition of a suitable nitrile in either natural- or heavy-isotopic form. Imidoester product is then extracted/removed from the reaction mixture.

In another embodiment, in the initial labeling step, amines are reductively aminated using formaldehyde.

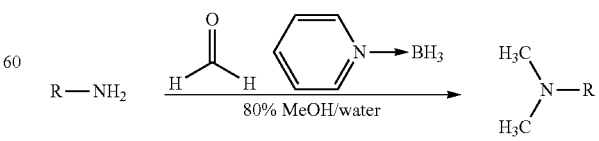

The isotopically-light version of formaldehyde consists of carbon and hydrogen atoms having normal isotopic abundance whereas the isotopically-heavy formaldehyde employs $^{13}$C. The end-product from the labeling reaction has a high pK$_a$ (~10), so it readily ionizes under typical positive ion-mode LC/MS conditions.

In another embodiment, in the initial labeling step, primary and secondary amines may be reductively aminated using heavy and light formaldehyde in the presence of 30× formaldehyde and 50× pyridine-borane in 4:1 MeOH:water. In that scheme, the ionizability of the analyte is preserved, and the MS sensitivity is enhanced due to higher pKa and increased hydrophobicity. That scheme also provides limited chromatographic impact due to small label size. Characteristic mass shift between heavy and light forms also signify the presence of amine functional group(s): 2 Da for each primary amine and 1 Da for each secondary amine.

General Strategy for Labeling Carboxylic Acid Compounds With Permanently Ionized Amines. Acid labeling is achieved by the addition of a molecule containing a permanently ionized amine (e.g. quaternary amine) and a labeling amine (e.g. primary amine) in the presence of a base (e.g. TEA) and a coupling reagent (e.g. HOBt and HBTU) in some solvent (e.g. DMSO).

Cholamine Syntheses via Alkylation. Cholamine is also known as a 2-amino-ethyl-N,N,N-trimethylammonium compound. Exhaustive alkylation compounds containing a permanently ionized amine (e.g. quaternary amine) coupled with an amine suitable for acid labeling (e.g. primary amine) can be constructed from the parent diamino compounds wherein one of the amines is protected with a protecting group (e.g. BOC or Alloc). Exhaustive alkylation is first performed under basic conditions (e.g. KHCO$_3$) with excess of the alkyl halide (e.g. Iodomethane). The resulting quaternary amine-protected amine products are then deprotected (with e.g., HCl or TFA, trifluoroacetic acid, or Ni(CO)$_4$ in DMF/water or Pd(Ph$_3$P)$_4$, Bu$_3$SnH and AcOH) yielding an amine suitable for labeling (e.g. primary amines) and also containing a permanently ionized amine (e.g. quaternary amine) for MS. A discussion of quaternizing amines may be found in Chen F C et al., A New Method of Quaternizing Amines and Its Use in Amino Acid and Peptide Chemistry. *Can. J. Chem.* 1976, 54, 3310-3311.

Cholamine Synthesis via Reductive Amination with Alkylation. Compounds containing a permanently ionized amine (e.g. quaternary amine) coupled with an amine suitable for acid labeling (e.g. primary amine) can be constructed from the parent diamino compounds wherein one of the amines is protected with a protecting group (e.g. Boc). Reductive amination is performed with excess of the aldehyde (e.g. formaldehyde) or a ketone (e.g. acetone) in the presence of a reducing agent, e.g. NaCNB(r)$_3$, wherein r=hydrogen or deuterium) to generate higher derivative amine (e.g., secondary or tertiary amine) products. A discussion of reductive amination may be found in Lane C F et al., Sodium Cyanoborohydride—A Highly Selective Reducing Agent for Organic Functional Groups. *Synthesis* 1975, 3:135-146. The higher derivative amines (e.g., secondary or tertiary amines) are next reacted with an alkyl halide (with or without a base present) to produce a further derivitized amine (e.g. quaternary amine). The protecting group is removed from the protected nitrogen yielding the labeling amine (e.g. primary amine) coupled to a permanently ionized amine (e.g. quaternary amine).

Preparation of Isotopic Variants of Cholamine. In one embodiment, cholamine (or other quaternary amines) are used as isotopic labels for carboxylic acids by reacting the carboxylic acid with 100× heavy or light cholamine in the presence of 10×HOBt, 10×HBTU, and 200×TEA in DMSO. That method advantageously provides a fixed positive charge that is easily ionized under typical positive ion-mode MS. The method also provides enhanced MS sensitivity due to the fixed charge. Ionizability of the analyte is also preserved by labeling with the stable charged reagent. The method further provides limited chromatographic impact due to the small size of the label. The method still further provides characteristic mass shift between heavy and light forms signifying carboxylic acid functional group presence.

Relative quantification of carboxylic acid-containing metabolites using isotopic labeling for the analysis of fatty acids is demonstrated herein. Fatty acids and other metabolite classes containing carboxylic acids have been analyzed by a number of GC and LC methods. Capillary column GC, often with MS detection, has been used extensively for fatty acid analysis. The process usually entails hydrolysis of lipids to release free fatty acids, which are then derivatized to methyl, trimethylsilyl, or pentafluorobenzyl esters to increase volatility. Prior to GC-MS analysis, isotopically-labeled internal standards may be added to the samples. LC-MS methods are becoming more common and have been developed for many metabolite classes that contain carboxylic acids. LC-MS of fatty acids in acidic conditions are preferable for the chromatographic separation. However, basic conditions impart a negative charge to the carboxylic acid functional group and provide superior detection sensitivity for electrospray ionization mass spectrometry (ESI-MS). Derivatization may be employed to improve detection sensitivity for positive-ion mode ESI-MS under acidic conditions.

The instant invention is a fast and robust derivatization strategy that incorporates both a positively-charged functional group and an isotopic label for improved relative quantification of fatty acids. The carboxylic acid group is converted into an amide by coupling it to cholamine, whereby reaction of a carboxylic acid metabolite with cholamine to form a product with a quarternary ammonium group enhances MS analysis in positive-ion mode.

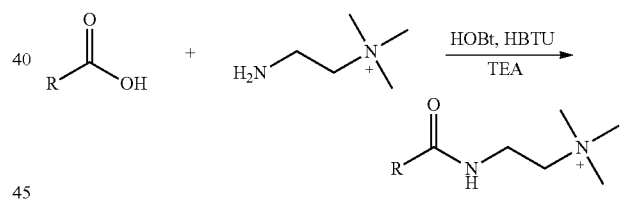

The quaternary ammonium group provides the labeled compound with a net positive charge, which greatly enhances ionization in positive-ion mode ESI-MS. Incorporation of deuterium into the methyl groups also provides isotopic variants of the labeling reagent. Separation of the various labeled fatty acids may be accomplished using reverse-phase HPLC under acidic conditions. Co-elution of the isotopic pairs for deuterium labeling on the methyl groups of a quaternary ammonium functional group is provided. Co-elution simplifies data analysis and provides precise relative quantification of fatty acids, as demonstrated with egg lipid samples obtained from chickens that were fed diets differing in lipid kit.

The isotopically heavy form of cholamine may have 9 deuterium atoms on the methyl groups of the quaternary amine instead of the conventional 9 hydrogen atoms. The relatively small size/mass of the instant cholamine residue minimizes undesirable impact on chromatographic separation. Peak shifts of 9.05649 Daltons in the mass spectrum (obtained after labeling) show that the analyte end-product contained carboxylic acid groups.

Labeled target analytes having both functional groups (i.e., amines and carboxylic acids groups) such as amino acid molecules have other characteristic mass shifts which are useful information for identifying unknown compounds. The reaction conditions using the instant labeling reagents avoids clean-up prior to introducing the reagent/target end-product to the LC/MS system.

Relative quantification of heavy- and light-labeled molecules is accomplished by ratioing two peaks from a mass spectrum. The heavy and light forms are resolvable by the mass spectrometer. The resolution, R, of a typical mass spectrometer is defined by the equation: $R=m_1/(m_1-m_2)$, wherein $m_1$ is the mass of heavy compound and $m_2$ is the mass of the light compound. Relative quantification of the target molecule, T, using the isotopically-different labels, L and L*, follows the equation: $TL^*/(TL^*-TL)<R$, wherein TL is the mass of the light-labeled target molecule and TL* is the mass of the heavy-labeled target molecule. As can be appreciated, the minimum resolvable mass difference between a pair of isotopic labeled target molecules is generally a function of the mass of the target molecule and the resolution limit of the particular mass spectrometer used.

Hence, the mass difference between the heavy and light labels may be as small as 0.001 Dalton where the mass of TL is around 100 Dalton. The instant invention advantageously imparts small mass differences between heavy and light target molecules, such as where the heavy-labeled end-product has $^{13}C$, $^{15}N$ and/or $^2H$ and the light-labeled end-product has $^{14}N$, $^{12}C$ and/or $^1H$. The mass difference between such pairs of molecules is at least around 1 Dalton. Preferably, the instant labeling reagents create mass differences between heavy and light labeled target molecules of around 2 Daltons or more which advantageously eliminates or minimizes peaks arising from naturally-occurring isotopic variations in the target molecule.

Relative Quantification of Carboxylic Acid Metabolites by LC-MS Using Isotopic Variants of Cholamine. Labeling reagents that differ only in their isotopic kit offer a powerful approach to achieve relative quantification between samples by ESI-MS. Heavy and light isotopic forms of cholamine, which contain a positively charged quaternary ammonium group, were synthesized and tested as new labeling reagents for the relative quantification of carboxylic acid-containing metabolites, specifically fatty acids.

The positive charge on cholamine ensures that the labeled product is also positively charged under all LC/MS conditions, regardless of mobile phase pH. This leads to high ionization efficiency and correspondingly high detection sensitivity for the analysis of fatty acids in positive ion mode ESI-MS after reverse-phase separation under acidic conditions. Good accuracy and precision were obtained by mixing heavy- and light-labeled hydrolyzed egg lipid extracts in different known ratios.

The relative quantification results for ten observed fatty acids had an average absolute error of 4.6% and an average coefficient of variation (CV) of 2.6%. The labeling strategy yielded a median CV of 6% when employed for fatty acid analysis of eggs from chickens fed various dietary supplements.

Solid Support

As shown in the reaction scheme below, in a preferred embodiment, imidoester is immobilized directly on the solid support. The target analyte reacts directly with immobilized imidoester. The solid phase immobilized imidoester is prepared by having the solid support initially terminated with an alcohol. In accordance with a Pinner reaction, the alcohol reacts with the nitrile group to produce immobilized imidoester. The solid support material is compatible with the conditions of the Pinner reaction, which means that the solid support is insoluble in the solvent system and that the primary reaction (most abundant end-product) is immobilization of the imidoester:

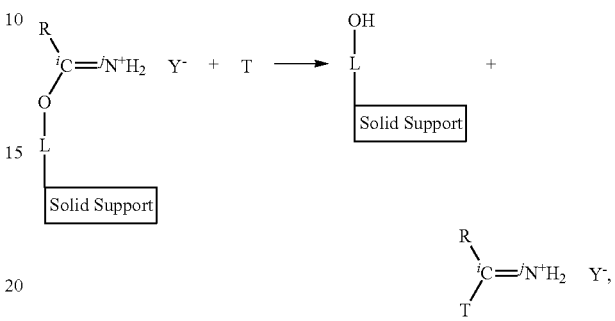

wherein R is a member selected from the group consisting of $C_{1-4}$ branched or linear, saturated or unsaturated alkyl containing any number of hydrogens or deuteriums and any number of $^{12}C$ or $^{13}C$, or

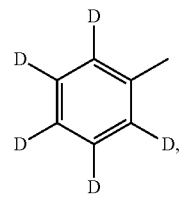

wherein R is preferably

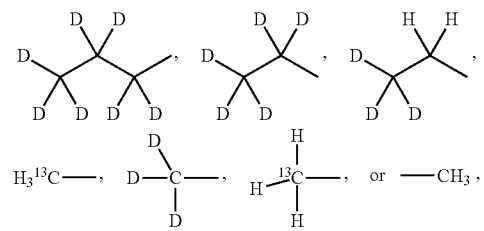

wherein D is deuterium, wherein i=12 or 13, wherein j=14 or 15, wherein Y⁻ is a suitable anion (such as a single charge organic or inorganic counter-anion, preferably Cl⁻, Br⁻, or I⁻), wherein L is a bond or a linker, and wherein T is the target analyte molecule containing primary amines, secondary amines, or primary and secondary amines (such as an amino acids, proteins, peptides or metabolites). The linker may be a suitable molecule known in the art, such as those disclosed by Hermanson, G, Bioconjugate Techniques, Academic Press (Jan. 8, 1996). The linker may also be a suitable silane or a Self Assembled Monolayer (SAM) known in the art. T is a target analyte molecule containing primary and secondary amines (such as an amino acid, protein, peptide or metabolite). The -O-L-[Solid Support] moiety is also known in the art as a leaving group.

As used herein, the linker "L" refers to a covalent chemical connection between a solid support and a label. Exemplary linkers include, but not limited to, silanes, functionalized alkanethiols, functionalized poly(ethylene) glycols, functionalized alkenes, homo- and hetero-bifunctional cross-linkers, derivatives thereof and the like.

As used herein, "support", "solid support" and "solid carrier" are used interchangeably and refer to a suitable solid phase material, whereby the instant labeling reagents are immobilized directly to the support via a linker, and whereby the reagent may be used to label one or more analytes. Solid supports are herein considered an attachment that renders the labeling reagents soluble under conditions suitable for labeling the target analyte, whereby the support can be readily separated from the other soluble components by simple known physical processes, such as filtration and centrifugation.

The solid support may be an insoluble, functionalized material. The solid support may be bonded to a linker that allows the adhering molecule to be readily separated from excess reagent, soluble reaction by-products, solvents and the like by filtration, centrifugation and the like. The solid support may be planar, spherical or irregular (e.g., blocky) in shape. The solid support may also be constructed from porous polymer, copolymer, or macromolecules, or a solid sample vial wall (single or multiplex). Preferably, the solid support is constructed from a metal (e.g., gold, silver or iron); a functionalized metal (e.g., self-assembled alkanethiol monolayers); glass, silicon, and silanized/photo-functionalized forms thereof; carbonaceous materials (e.g., diamond, amorphous carbon, glassy carbon, graphite, etc.), and, silanized/photo-functionalized derivatives thereof; plastic and functionalized plastic; polymers and functionalized polymers; nano and micro particles of metal and metal colloids and functionalized derivatives thereof; nano- and micro-diamond and other carbonaceous particles, and functionalized particles thereof; silica particles such as silica gel and functionalized particles thereof; zirconia and functionalized zirconia; beads and functionalized beads (such as agarose, cordierite, polystyrene, glass, polymethylmethacrylate and ceramic); resin and functionalized resin (see, products available from Polymer Laboratories, Inc.); and, the like.

The target analyte reacts directly with immobilized imidoester. In the instant invention, the solid support and the linker are compatible with Pinner reaction conditions. Linker functionalized imidoesters are attached to the solid support using conventional coupling chemistry. (See Hermanson). The linker molecule and the attachment point between the linker and solid support are non-reactive toward primary and secondary amines under labeling conditions (target plus imidoester).

Alternatively, a bifunctional linker having one end terminated with an alcohol may be reacted with a nitrile to produce an imidoester. The distal end of the linker may then be subsequently reacted with a solid support or functionalized solid support in order to immobilize the imidoester using conventional coupling chemistry. (See Hermanson).

Increasingly, electron transfer dissociation (ETD) is being employed for peptide and protein MS analysis. As compared to a conventional technique, collision-activated dissociation (CAD) (also known as collision-induced dissociation (CID)), ETD provides a more robust method to characterize post-translational modifications (PTMs) and to interrogate large peptides or even whole proteins. Because of these attributes and the fact that it generates c- and z-type products (instead of b- and y-type) ETD is highly complementary to CAD. Many PTMs, unfortunately, are especially labile under CAD conditions. ETD was developed to enable the large-scale characterization of protein phosphorylation. In a study comparing ETD to CAD, ETD outperformed CAD for all charge states greater than two. However, a decrease in percent fragmentation as a function of increasing precursor m/z was observed with ETD fragmentation regardless of precursor charge. This decrease can be mitigated by incorporation of fixed-charge tags, which effectively lower m/z values by creating ions in higher charge states.

Modifying proteins or peptides with fixed-charge tags leads to higher charge state ions from electrospray ionization mass spectrometry (ESI-MS). The fixed charge is due, in the instant invention, to a quaternary ammonium group in the labeling reagent, which is attached to all carboxylic acid functional groups of the peptide/protein via an amidation reaction. The permanent positive charge thereby replaces a potential negative charge (deprotonated carboxylic acid), which leads to significantly more charges from positive-ion mode ESI, an exemplary mode for peptide and protein ESI-MS. Carboxylic acid functional groups are present in all proteins and fragments. Thus, in comparison to the Cys specific isotope tags, peptide and protein coverage is increased.

The higher charge states offer advantages for peptide and protein analysis by mass spectrometry. An important benefit is an increased fragmentation of these more highly charged ions during ETD. Other fragmentation methods such as electron capture dissociation (ECD) and CAD may also benefit from the fixed charges. However, CAD is disadvantaged by neutral trimethylamine loss which sometimes occurs with quaternary ammonium groups in the mass spectrometer.

Another benefit of the instant invention is that the carboxylic acid groups are blocked by the reaction. This feature is especially advantageous for analyzing proteins having phosphate groups as PTMs. These phosphoproteins are important biologically, and are the focus of many proteomics studies. Selective enrichment of phosphopeptides (from tryptic digests of phosphoproteins) often is performed with IMAC (immobilized-metal affinity chromatography). Free (unlabelled) carboxylic acid groups interfere with this procedure, and therefore are usually blocked by conversion to the methyl esters. The instant invention advantageously accomplishes this blocking function. Furthermore, ETD is the preferred mode of analysis for phosphopeptides because the phosphate group does not fall off, as often occurs during CAD. Thus, a single labeling reaction performs two beneficial functions: It blocks the carboxylic acid groups to aid IMAC purification, and it improves the ETD analysis due to the production of higher charge state ions.

The relative quantification methodology also applies to peptides/proteins labeled for ETD analysis. In other words, a single mass spectrometric analysis of labeled peptides/proteins provides both precise relative quantification (via the use of isotopic variants) as well as improved protein identification (via ETD fragmentation of the more highly charged ions).

The instant invention provides ionizable, isotopic labeling reagents that increase charge state through incorporation of fixed charges, block carboxylic acid functional groups for improved affinity selection of phosphopeptides, and yield labeling reaction products for relative quantification using mass spectrometry.

Example 1

Synthesis of $^{12}C_2$- and $^{13}C_2$-Methylacetimidate. The synthesis of methylacetimidate was based in part on a published synthesis. (Hunter M J et al., *In Methods in Enzymology—Enzyme Structure Part B*; Hirs C H W et al., Eds.; Academic Press: New York and London, 1972; Vol. XXV, pp 585-596). A Pyrex test tube was fitted with a triangular stirvane and a rubber septum and purged with $N_2$. Dry electronic grade methanol (Fisher), 0.625 mL (15.5 mmol), was added to the vial. Then, 868 mg (23.8 mmol) of gaseous HCl was added over a period of approximately three hours at room temperature. The HCl gas was generated in a $N_2$-purged round-bottom flask by slow drop-wise addition of concentrated $H_2SO_4$ onto solid NaCl with stirring. The gas outlet of this flask was connected to a drying line filled with $CaSO_4$ and then introduced to the reaction vial through a Teflon coated syringe needle. Under positive $N_2$ pressure, the reaction test tube was moved to a dry ice/acetone bath and 0.625 mL (11.9 mmol) of dry acetonitrile, $^{12}C_2H_3N$, (Sigma-Aldrich) was added drop-wise and allowed to freeze. For preparation of the $^{13}C_2$-product, 0.625 mL (11.7 mmol) of dry $^{13}C_2$-acetonitrile (Cambridge Isotope Labs) was used. The reaction was then brought to 0° C. and allowed to stir overnight. After 8-12 hours a white precipitate formed. The total reaction time was approximately 24 hours, at which time ~2 mL of dry ether (CCl) was added.

The resulting slurry was allowed to stir for 15-30 minutes after which time the ether was decanted. The white product was dried under a stream of $N_2$ for one hour. No further purification was necessary. The products isolated as the hydrochloride salts. The yields of the $^{12}C_2$- and $^{13}C_2$-products were 1.05-1.17 g (9.58-10.68 mmol, 80-89%) and 1.09-1.11 g (9.74-9.98 mmol, 83-85%), respectively. Characterization of the $^{12}C_2$-product included a melting point of 95° C. and $^1$H NMR (300 MHz, $CDCl_3$) δ(ppm) 2.527 (s, 3H, $CH_3$), 4.303 (s, 3H, $OCH_3$), 11.517, 12.459 (broad d, 2H, $NH_2$). The melting point of the $^{13}C_2$-product was 98° C., and the $^1$H NMR results were δ(ppm) 2.295, 2.737 (d), 3H, $CH_3$), 4.307 (s, 3H, $OCH_3$), 11.520, 12.486 (broad d, 2H, $NH_2$). Methylacetimidate is also commercially available. All moisture-sensitive reactions were performed in oven-dried glassware under a stream of nitrogen. Bath temperatures were used to record reaction temperatures. All reactions were stirred magnetically.

Example 2

Optimization of Methylacetimidate Reaction Conditions. The labeling reaction between primary and secondary amines and methylacetimidate hydrochloride utilizes a solvent system in which both the amine-containing metabolites and methylacetimidate hydrochloride are soluble. Fairly polar metabolites, such as amines, are typically extracted from biological samples using binary mixtures of either methanol:water or acetonitrile:water. (Want E J et al., Anal. Chem. 2006, 78, 743-752). Therefore, similarly polar solvent systems may be targeted for the optimization of methylacetimidate labeling of amine containing metabolites. Valine (Val) and proline (Pro) provide challenging reaction conditions because the bulky side chain of Val and the secondary amine of Pro often make coupling to their amines difficult. Each amino acid (5.0 mM) was reacted with varying amounts of methylacetimidate in MeOH, water or binary mixtures thereof. The concentration of triethylamine (TEA), a basic tertiary amine, was held equivalent to the concentration of methylacetimidate in each experimental test.

Quantitative reaction yields were found within 1 hour using 95:5 methanol:water with 15 and 20 equivalents of methylacetimidate and TEA for Val and Pro, respectively. Solvent mixtures with greater than 5% water led to incomplete reactions, possibly because the methylacetimidate slowly hydrolyzes in water. Anhydrous methanol also reduced the reaction efficiency compared to 95:5 methanol:water. Another consideration is that the methylacetimidate reagent must be in its protonated form to undergo the reaction, while the metabolite amine is deprotonated. Triethylamine (TEA) was used as a suitable base to control the pH of the reaction. The pKa of 10.8 for TEA caused it to deprotonate the primary amine metabolites (pKa ~9-10) but leave the acetimidate reagent (pKa 12.5) in its protonated form. The reaction proceeds with the amine nucleophile reacting with the electrophilic labeling reagent. Since TEA is a tertiary amine, it does not react with methylacetimidate. The relatively high vapor pressure of TEA permits facile removal under vacuum. A solid-phase immobilized base (diethylaminomethyl polystyrene, Polymer Laboratories, Amherst, Miss.) was also used successfully, but the procedure with TEA is more convenient.

The extent to which side-chain nucleophiles of some metabolites (e.g. Cys, Ser, Thr, and Lys) would alter the desired amidine product formation was also tested. Secondary reactions of this type have been reported in the literature. (Rottmann A et al., J. Synthesis 1997, 313-327). In the case of acetimidate-labeled cysteine, the side-chain thiol reacts intramolecularly to cause complete mono-deamination (loss of ammonia) resulting in a single product (dihydro-thiazole) peak at 146.028 Da. The side-chain alcohol groups of Ser and Thr also caused mono-deamination, albeit to much lesser extents than cysteine, which resulted in the observation of dihydro-oxazole products at masses 130.050 and 144.066 Da, respectively. These dihydro-oxazoles partially reacted with water yielding mass spectral peaks at 148.061 and 162.077 Da. The mass spectrum of acetimidate-labeled lysine produced the expected product peak at 188.140 Da, but it did not contain any peaks resulting from secondary reactions. Thus, secondary reactions do occur for acetimidate-labeling of Cys, Ser, and Thr, and the products of these reactions maintain the desired $^{12}C_2$- or $^{13}C_2$-isotope tags that permit relative quantification.

Example 3

Figure 7:
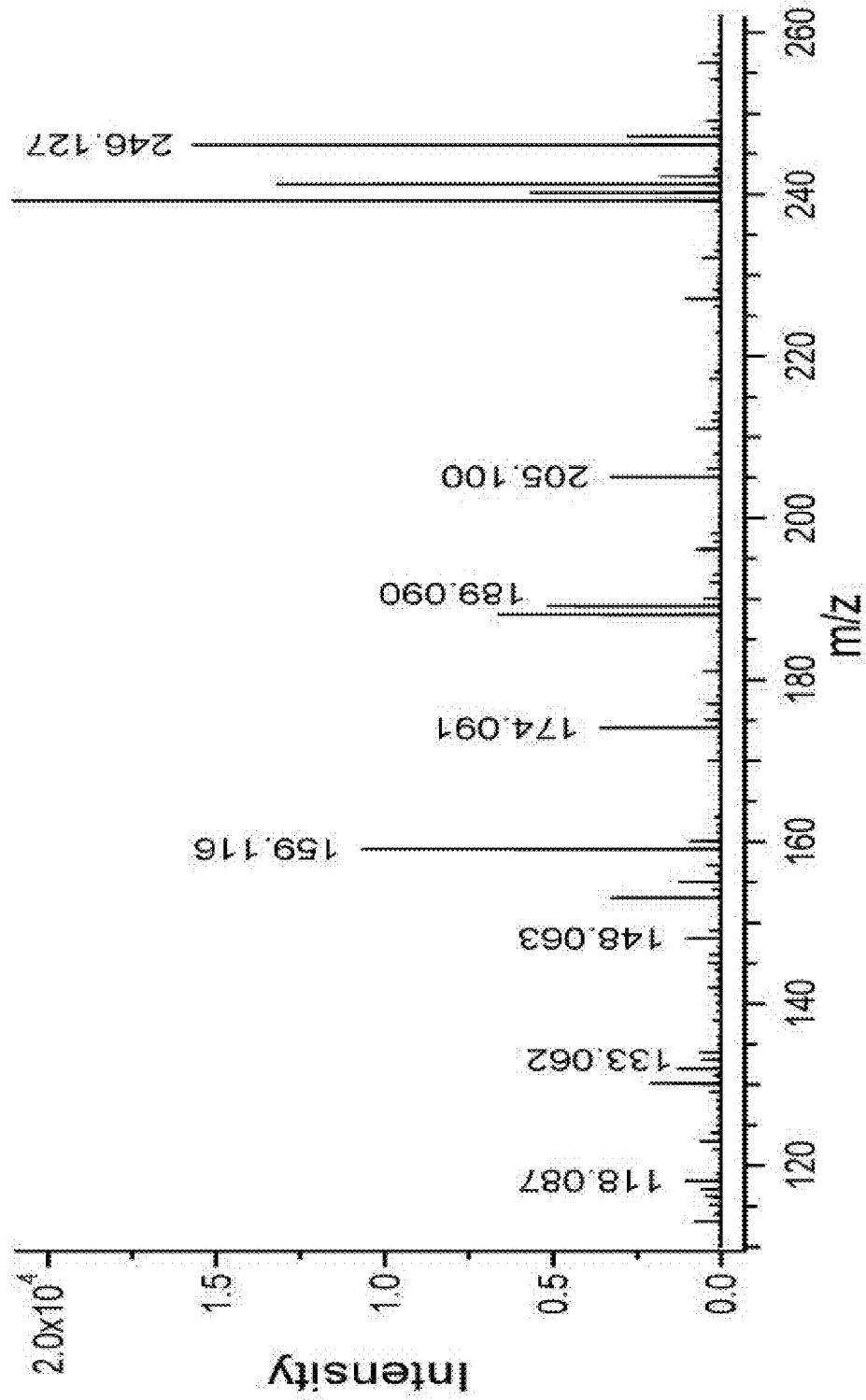
FIG. 7 is a graphical illustration showing methylacetimidate labeled and unlabeled qty. 4 amino acids (valine, asparagine, glutamic acid and tryptophan) using an equimolar mixture of the labeled and unlabeled compounds by ESI-MS, which demonstrates enhancement, whereby unlabeled valine (118.09 Dalton), asparagine (133.06 Dalton), glutamic acid (148.06 Dalton) and tryptophan (205.09 Dalton) versus labeled valine (159.10 Dalton), asparagine (174.09 Dalton), glutamic acid (189.09 Dalton) and tryptophan (246.12 Dalton) demonstrate an average increase in intensity for labeled amino acids over unlabeled amino acids as follows: 11.08× for valine, 6.61× for asparagine, 5.10× for glutamic acid, and 5.17× for tryptophan.

Enhancement of Amino Acid Ionization by Derivatization with Methylacetimidate. Qty. 4 amino acids (tryptophan, asparagine, glutamic acid and valine) were dissolved in 95:5 methanol:water (including 20 equivalents triethylamine) to a final concentration of 2.5 mM. A 95:5 methanol:water (with 100 mM triethylamine) produced quantitative labeling. A slight molar excess of methylacetimidate hydrochloride compared with the amine reactant is preferred. Two equivalent equimolar mixtures of the four amino acid solutions were prepared. One 1 mL aliquot of that solution was combined with 22.3 mg of methylacetimidate-HCl and reacted overnight. A second 1 mL aliquot of the equimolar mixture was the control. Both aliquots were diluted 1:100 in 80:20 acetonitrile:water having 0.1% formic acid. Each aliquot was separately analyzed by electrospray MS. A 1:1 mixture of the labeled and unlabeled respective amino acids was prepared and analyzed in a similar manner. A peak is observed for each of the eight compounds in the resulting mass spectrum. An enhancement in signal for the labeled form was 11.1× for valine, 6.6× for asparagine, 5.1× for glutamic acid, and 5.2× for tryptophan (See FIG. 7). The results demonstrate that methylacetimidate enhanced the ionization efficiency of each amino acid between 5 and 11-fold. The peaks arising from the four labeled compounds are generally the most intense peaks in the spectrum. It is worth noting that the tall peaks from 239-242 Da are due to the (2TEA+2H+Cl)+ ion; this sample contained a high concentration of TEA because it was not purified by vacuum centrifugation.

The signal from the labeled amino acids was between 5 to 11-fold higher than the signal for the corresponding unlabeled amino acids. That enhancement of mass spectral intensity may be due to the chemical structure of the labeled product along with the mechanism of electrospray ionization. The increased pKa of the labeled analytes (~12.5 for the acetimidinium group versus ~9.5 for the unlabeled α-amino group of amino acids) leads to preferential protonation in solution, which is advantageous for the ultimate generation of gas-phase ions by electrospray ionization. The labeled compounds exhibited an increase in hydrophobicity as evidenced by the decrease in retention time for HILIC chromatography discussed herein. Hydrophobic compounds are more likely to exist in the surface layer of the electrosprayed droplets. Ion evaporation creates gas-phase ions from that surface layer. These basic chemical principles may explain the substantial increase in ESI-MS sensitivity observed for compounds labeled with methylacetimidate. (Cech N B et al., *Anal. Chem.* 2000, 72, 2717-2723; and Enke C G, *Anal. Chem.* 1997, 69, 4885-4893).

Example 4

LC/MS methods employing hydrophilic interaction chromotagraphy (HILIC) may be used for analyzing amino acids. In HILIC, the elution order is the inverse of reverse phase chromatography; hydrophobic compounds elute first and hydrophilic compounds elute last. (Rabaglia M E et al., *Am. J. Physi. Endocrinol. Metab.* 2005, 289, E218-E224). A similar separation method was used.

HILIC LC-MS Analysis. The HPLC system included an LC Packings Famos auto-sampler, an UltiMate solvent pump and a UV/Vis detector operated at 190 nm (Dionex Corporation, Sunnyvale, Calif.). A 150×0.320 mm, poly(hydroxyethyl) aspartamide capillary column (The Nest Group, Inc. Southborough, Mass.) using 5 μm particle size and 100 Å pore-size was used for separation of the analytes. A 55 minute binary gradient elution profile was as follows: t=0, 80% B; t=5, 80% B; t=30, 25% B; t=35, 25% B; t=36, 80% B; and t=55, 80% B. Mobile phase A was 0.1% formic acid (EM, Gibbstown, N.J.) in HPLC grade water (Burdick & Jackson, Morristown, N.J.) and mobile phase B was 0.1% formic acid in HPLC grade acetonitrile (Burdick & Jackson, Morristown, N.J.). The flow rate was 4 μL/min and sample injection volumes were 2 μL. The LC effluent was directed to the capillary electrospray ionization source of a MicrOTOF time-of-flight mass spectrometer (Bruker Daltonics, Billerica, Mass.). Positive ion mode electrospray was performed at a potential of 4500 V using 0.4 bar of $N_2$ as a nebulizer gas and 4.0 L/min of $N_2$ drying gas at 150° C.

Effect of Labeling on Retention Time. Chromatographic separation of analytes from complex mixtures prior to MS improves sensitivity, at least in part, by limiting ion suppression effects. (Choi B K et al., *J. Chromatogr. A* 2001, 907, 337-342; Constantopoulos T L et al., *J. Am. Soc. Mass Spectrom.* 1999, 10, 625-634; Sterner J L et al., *J. Mass Spectrom.* 2000, 35, 385-391; Tang L et al., *Anal. Chem.* 1993, 65, 3654-3668; and, Annesley T M, *Clin. Chem.* 2003, 49, 1041-1044). Preferably, labeled compounds are chromatographically resolvable.

Figure 8:
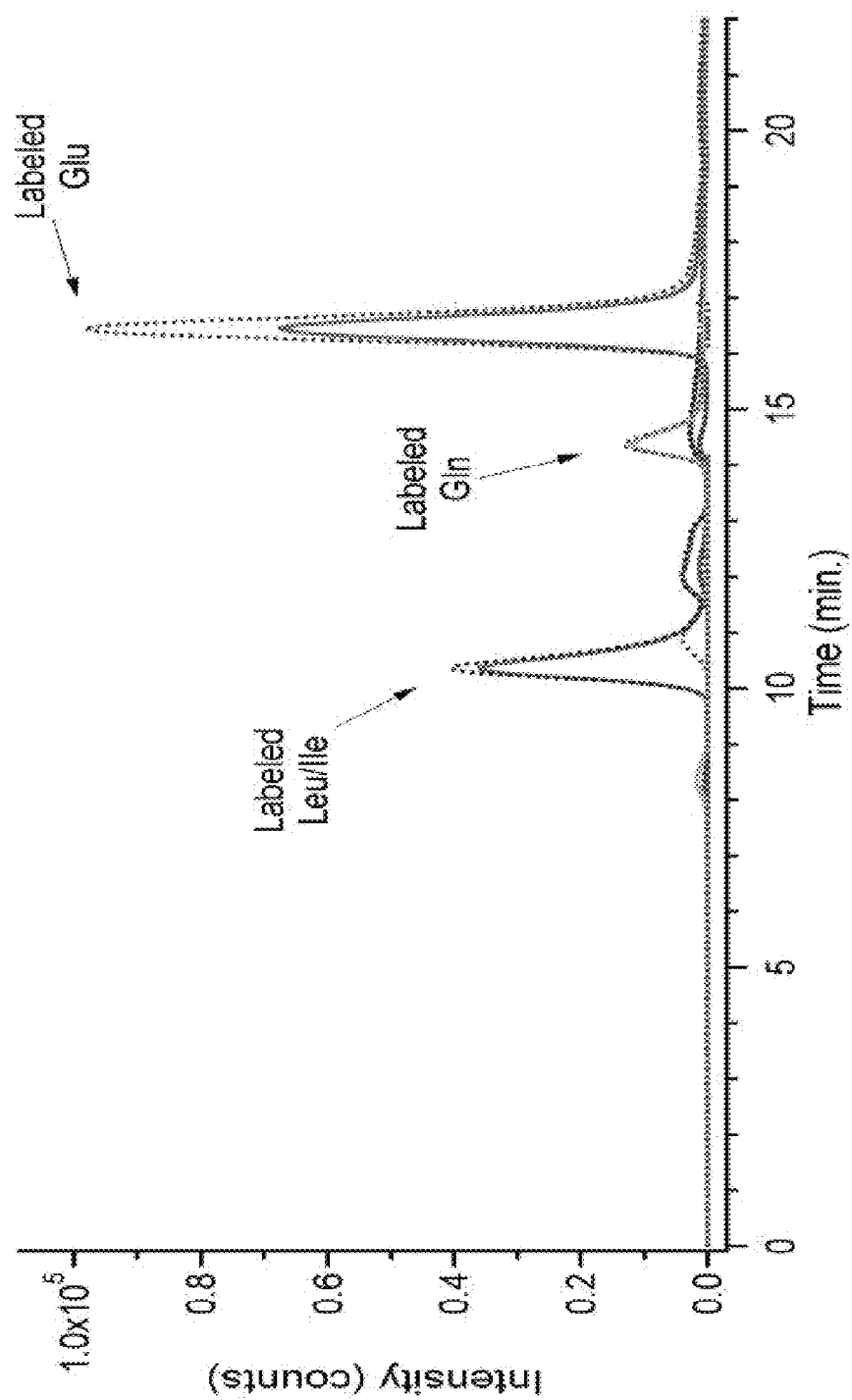
FIG. 8 is a graphical illustration of extracted ion chromatograms for the heavy and light methylacetimidate labeled versions of leucine/isoleucine, glutamine and glutamic acid, whereby the solid lines correspond to light-labeled versions, and whereby the dotted lines correspond to heavy-labeled versions.

The extracted ion chromatograms for a few methylacetimidate-labeled amino acids obtained from an LC-MS analysis of the *Arabidopisis* seed samples is shown in FIG. 8. The heavy- and light-labeled versions of each amino acid co-elute since incorporation of $^{13}C$ does not impact the analyte's interaction with the stationary phase. The elution order (labeled-leucine/isoleucine, labeled-glutamine and then labeled-glutamic acid) proceeded from hydrophobic to hydrophilic, which is expected for HILIC. That elution order is analogous to that of unlabeled versions of the three amino acids, but the labeled compounds each eluted earlier than the corresponding unlabeled amino acid. A comprehensive view of the effect of labeling on retention time is demonstrated in FIG. 1, whereby the adjusted retention times of labeled and unlabeled amino acids are plotted against one another.

In FIG. 1, the adjusted retention times ($T_R$-$T_M$) of labeled and unlabeled amino acids are plotted. The data show that elution times decreased by about 60% for the labeled versus unlabeled amino acids suggesting that labeling increases hydrophobicity. FIG. 1 shows a comparison of adjusted retention times for 11 representative labeled and unlabeled amino acids from *Arabidopisis* plant tissue extract, whereby a linear relationship between the two sets of compounds is observed, whereby the elution time of the labeled form is reduced by approximately 60% compared to the elution time of the unlabeled form, and whereby the order of elution for the unlabeled amino acids (shortest to longest) was Trp, Phe, Leu, Tyr, Val, Pro, Ala, Gln, Asn, Glu, and Asp, and whereby the order of elution for the labeled amino acids was Trp, Leu, Tyr, Val, Phe, Ala, Pro, Gln, Asn, Glu, and Asp.

Example 5

Metabolite Extraction from *Arabidopsis* Plant Tissue. *Arabidopsis* whole plant tissue (9.60 g wet weight) was placed in a 50 mL Falcon tube. Liquid nitrogen was added and the tissue was crushed to a fine powder using a glass rod. The crushed tissue was mixed with 23 mL of HPLC grade methanol (Burdick Jackson) and 0.80 mL of HPLC grade water (Sigma Aldrich). The mixture was heated at 50° C. for 30 minutes and then sonicated for 15 minutes. The sample was centrifuged at 10,000 rpm for 20 minutes and decanted. The liquid was reduced to dryness in a rotary evaporator and redissolved in 20 mL of methanol. The solution was filtered through 0.2 μm filters (Millex-GV) and finally aliquoted into 800 μL portions in 1.5 mL centrifuge tubes. The samples were reduced to dryness in a vacuum centrifuge and stored at −40° C.

Figure 5:
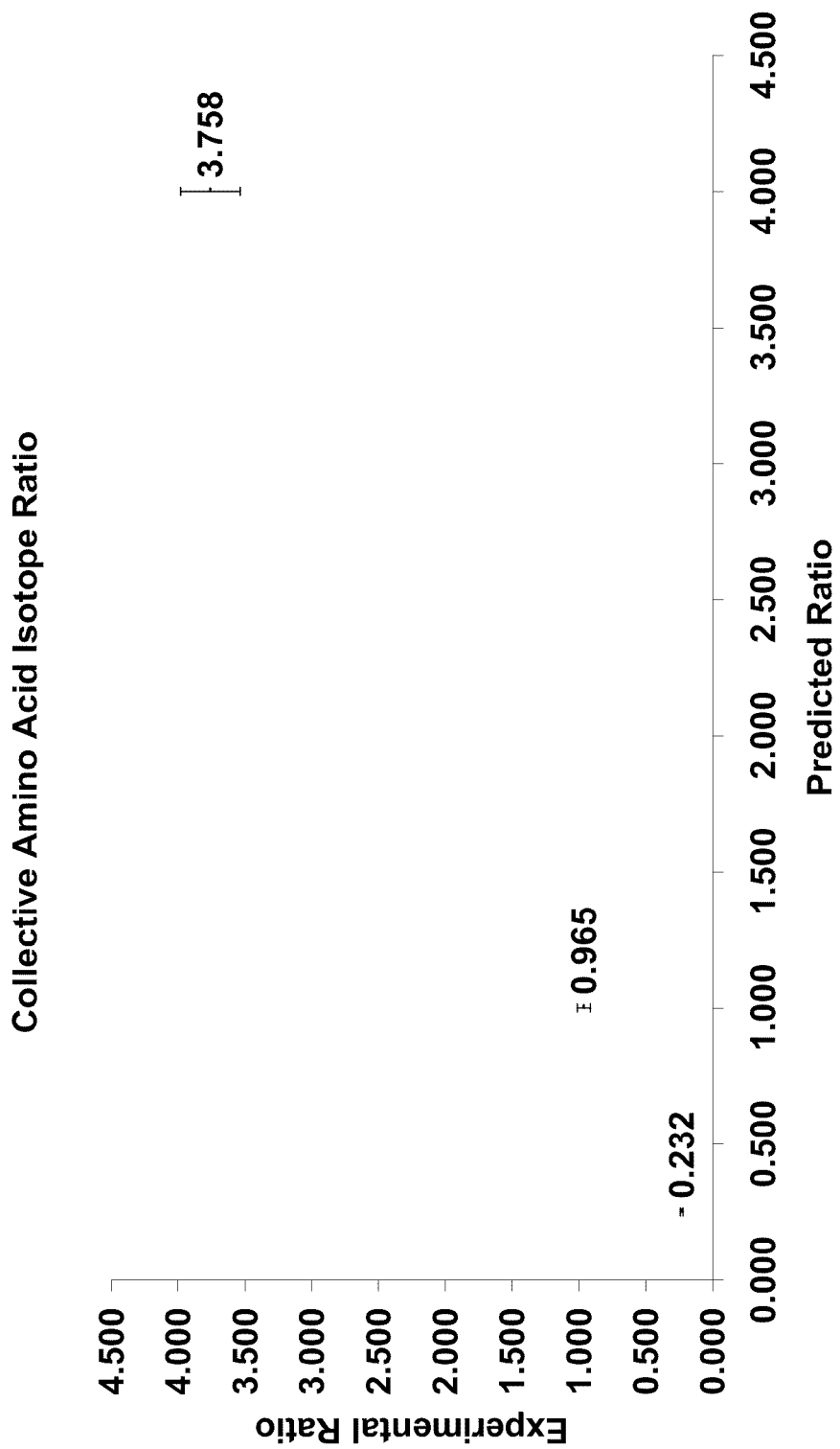
FIG. 5 is a graphical illustration showing collective heavy- and light-labeled amino acid extracted ion chromatogram peak ratios of eight amino acids, whereby two identical samples of metabolites extracted from Arabidopsis were labeled with heavy and light isotopic forms of methylacetimidate and mixed in ratios of 0.25:1, 1:1 and 4:1, and whereby the peak intensity ratios of the qty. 8 heavy and light labeled amino acids (arginine, lysine, asparagine, leucine, valine, alanine, glutamic acid and glutamine) were calculated and averaged from two separate LC/MS runs and then found to be 0.232, 0.965 and 3.758 respectively, whereby the data reflects the relative kit of 2 test samples over a broad range of ratios, and whereby the graph displays average ratios (with standard deviations), and whereby the expected values for the 3 mixtures were 0.25, 1.00 and 4.00.

Labeling of *Arabidopsis* Whole Plant Metabolites with Methylacetimidate. One sample of *Arabidopsis* tissue extract was re-dissolved in 80:20 methanol:water and divided into two equivalent portions. These portions were reduced to dryness in a vacuum centrifuge. The two samples were re-dissolved in 300 μL of labeling reaction solvent (95:5 methanol:water with 100 mM triethylamine, 99.5%, Aldrich). Approximately 6 mg total of solid methylacetimidate hydrochloride was added over the course of four separate additions to the dissolved extract. The additions were spaced approximately 10 minutes apart, and the sample was agitated in a vortex mixer between additions. One of the two samples was treated with the light $^{12}C$ methylacetimidate and one was treated with the heavy $^{13}C$ methylacetimidate. The samples were then left to react overnight before being reduced to dryness in a vacuum centrifuge. The samples were dissolved in 80:20 acetonitrile:water having 0.1% formic acid. Three mixtures of the two samples were prepared in the following ratios 1:4, 1:1 and 4:1 ($^{12}C$:$^{13}C_2$, respectively). All three samples were diluted 1000-fold in 80:20 acetonitrile:water having 0.1% formic acid prior to HILIC HPLC followed by ESI-MS. Extracted ion chromatograms were obtained for the masses corresponding to the heavy- and light-labeled versions of eight amino acids. The ratios of peak intensities were calculated for each pair of heavy- and light-labeled amino acids. For each of the three sample mixtures, these eight peak ratios were averaged and the results were 0.23+/−0.01, 0.97+/−0.05, and 3.76+/−0.22 (see FIG. 5). These experimental values are in excellent agreement with the predicted ratios of 0.25, 1.00 and 4.00.

Example 6

Germination of *Arabidopsis* Seeds. Wild-type *Arabidopsis* seeds were divided into two samples of 100 mg each. One seed sample (−NaCl) was placed on 1×MS+2% sucrose plates (Phytotechnology Laboratories, Lenexa Kans.) that was previously covered with filter paper. The other seed sample (+NaCl) was placed on 1×MS+2% sucrose+150 mM NaCl plates that was also previously covered with filter paper. The seeds were allowed to germinate for 20 hours in a dark environment. Seeds were recovered from the filter paper and allowed to air dry for 30 minutes. Seed were placed in a plastic vial and dried in a vacuum centrifuge.

Metabolite Extraction from *Arabidopsis* Seed Tissue. A 2 mL screw-top centrifuge tube was filled half way with 3 mm diameter glass beads (Glen Mills, Cliftor, N.J.). The beads were washed 3 times with 8:1 methanol:water, and then dried under vacuum. *Arabidopsis* seed tissue (85 mg) from each of the two samples was added to separate tubes along with 1 mL of the 8:1 methanol:water solution. The seeds were pulverized using a mini-beadbeater (Glen Mills, N.J.) at 4800 rpm for 180 seconds. The resulting mixture was placed on ice for 10 minutes and centrifuged at 14,500 rpm and 0° C. for 10 minutes. Four equivalent 100 µL aliquots of supernatant were removed by pipette from each sample. The eight samples were reduced to dryness using a vacuum centrifuge.

Figure 6:
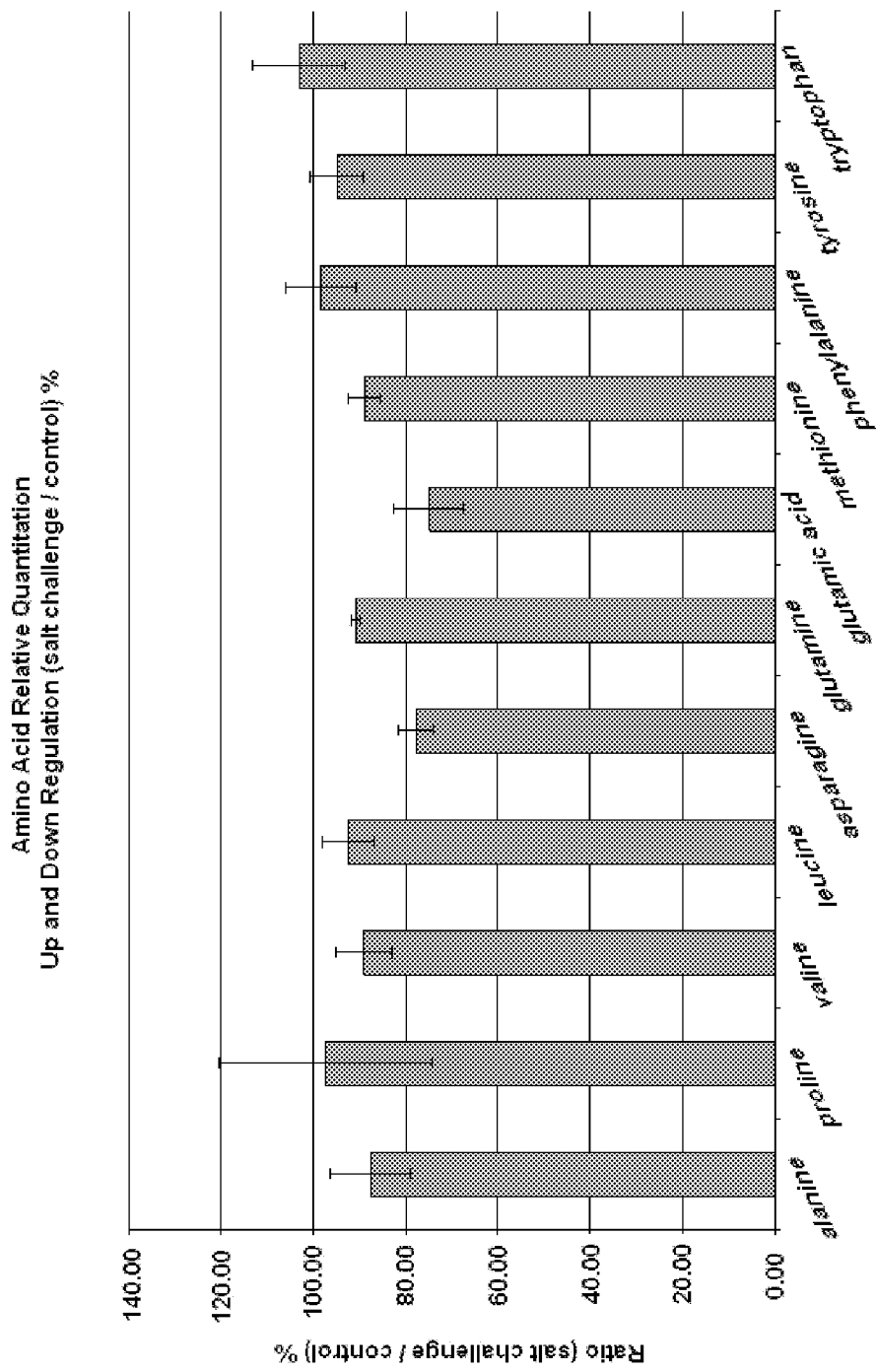
FIG. 6 is a bar graph illustration showing relative quantitation of qty. 11 amino acids in a 1:1 heavy:light labeled mixture of salt-challenged versus control Arabidopsis seeds (i.e., under +NaCl and −NaCl conditions during germination), whereby the data demonstrates that many amino acids in +NaCl condition are down regulated, whereby data in the graph are peak ratios of peak height for heavy- and light-labeled compounds, and whereby the target molecules were labeled with light and heavy methylacetimidate.

Labeling of *Arabidopsis* Seed Metabolites with Methylacetimidate. Dried extracts were re-dissolved in 100 µL of labeling solvent (95:5 methanol:water with 100 mM triethylamine). Two of the +NaCl samples and two of the −NaCl samples were treated with two separate additions of 2 mg light methylacetimidate. Likewise, two of the +NaCl samples and two of the −NaCl samples with treated with two separate additions of 2 mg heavy methylacetimidate. Additions of methylacetimidate were spaced 20 minutes apart. The samples were left to react for 1 hour following the second addition but before being reduced to dryness in a vacuum centrifuge. Dried samples were dissolved in 100 µL of water having 0.1% formic acid. The following mixtures were then prepared in duplicate: 20 µL (+NaCl extract) light labeled with 20 µL (−NaCl extract) heavy labeled; and, 20 µL (+NaCl extract) heavy labeled with 20 µL (−NaCl extract) light labeled. Thus, eight separate labeling reactions yielded four separate mixtures of heavy and light-labeled metabolites. Each of the four tubes was further diluted with 160 µL of acetonitrile having 0.1% formic acid. Injections of 2 µL from each mixture were analyzed by HILIC LC-MS (FIG. 6).

Relative Quantification of Amines in *Arabidopsis* Seeds using Methylacetimidate. Metabolites were extracted from wild type and mutant type *Arabidopsis* seeds. One of the samples was germinated under conventional conditions and the other was challenged with NaCl during the germination time. Such experiments are useful for studying the salt tolerance of seeds during germination, which is important in the breeding and genetic engineering of crops that could be irrigated with brackish water. Relative quantification was performed for 11 amino acids whose abundance was above the detection limit.

Figure 2:
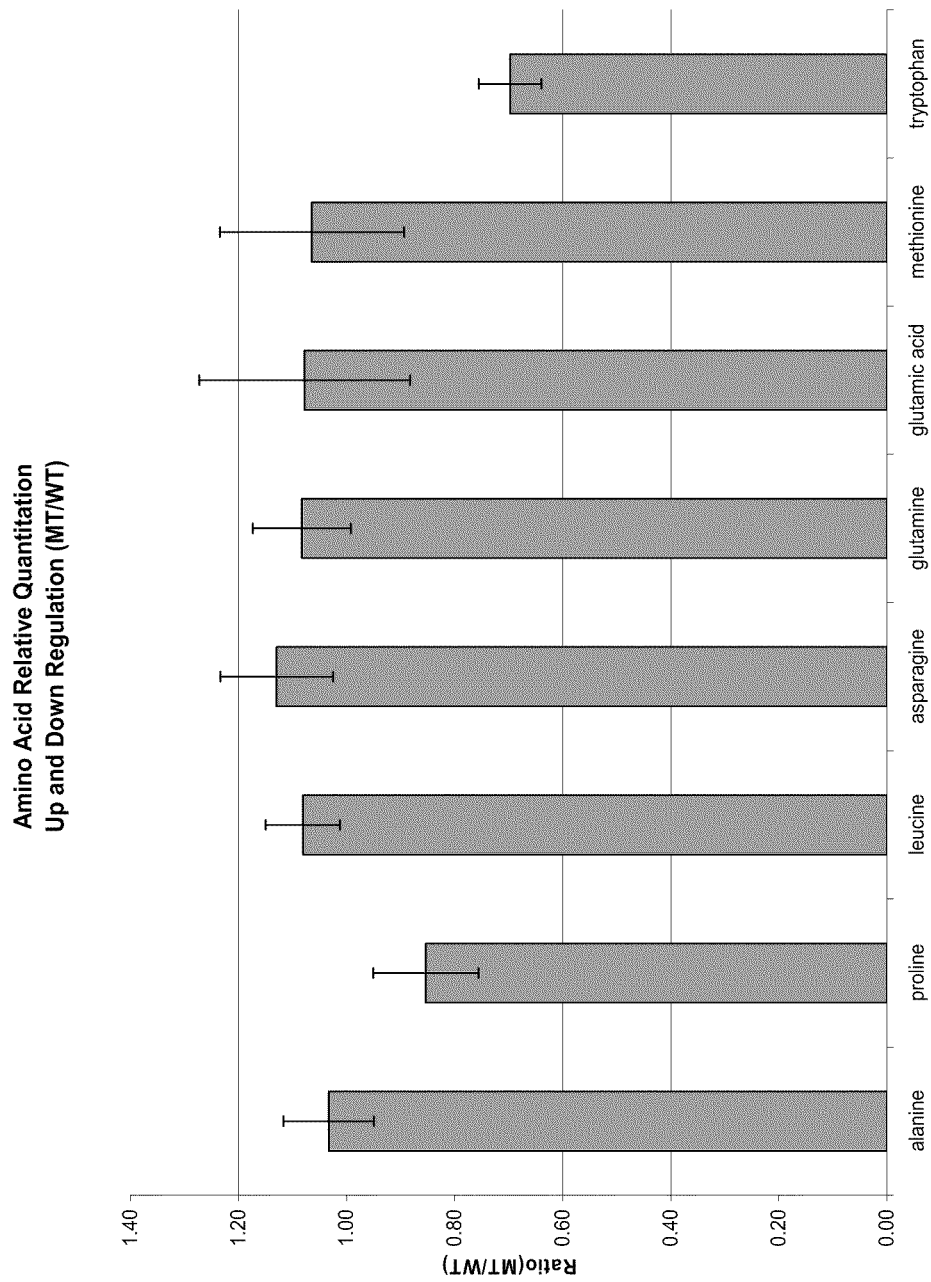
FIG. 2 is a bar graph illustration showing relative quantitation of qty. 8 amino acids in a 1:1 mixture of heavy methylacetimidate-labeled mutant-type and light methylacetimidate-labeled wild-type Arabidopsis in terms of up and down regulation, whereby data in the graph are ratios of peak height for heavy and light labeled compounds in the extracted ion chromatograms, whereby the data shows an ability to comprehensively and relatively quantify changes (e.g., down regulation of tryptophan and proline) in amine-containing molecules, and whereby MT is mutant type and WT is wild type Arabidopsis.
Figure 3:
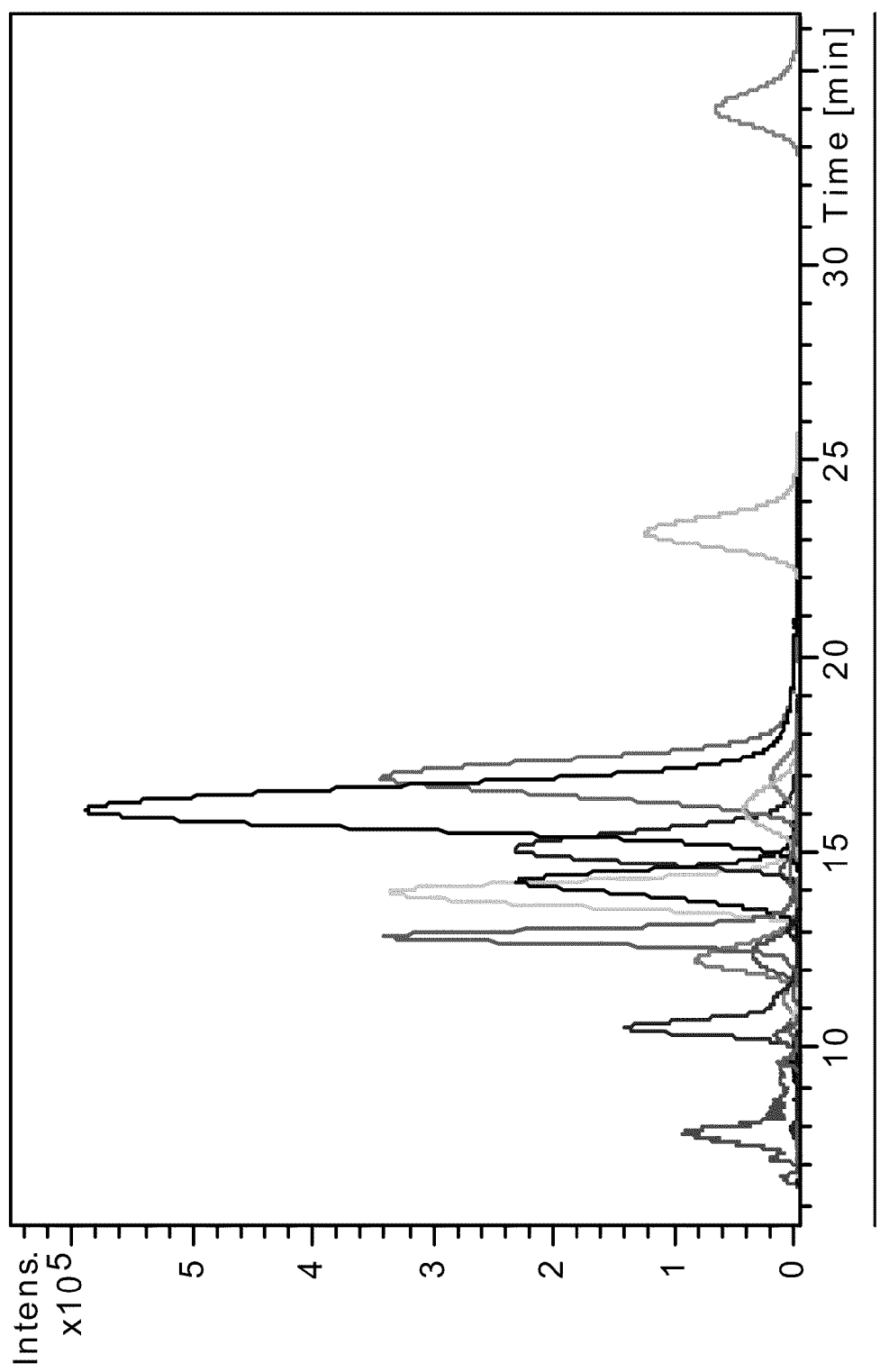
FIG. 3 is a graphical illustration showing extracted ion chromatograms of qty. 15 $^{12}$C formaldehyde labeled amino acids of Arabidopsis extract, whereby the labeled amino acids, from strongest to weakest signal, are glutamine, glutamic acid, asparagine, lysine, alanine, threonine, serine, valine, leucine, phenylalanine, proline, tryptophan, aspartic acid, tyrosine and glycine.

In several cases, the relative concentrations of amino acids in the salt-challenged seed samples decreased. The average of the relative standard deviations for all eleven amino acids was 8%, which is well within the useful range for metabolomic studies. Relative amino acid kits were determined using the method of labeling described herein. The mutant is a strain resistant to osmotic challenges present during irrigation using salt water. In wild-type strains, proline is accumulated in response to osmotic challenges. Since the mutant is defective in sensing osmotic changes, it was found to be deficient in proline. It is noted that tryptophan is significantly depleted in the mutant type seeds. (See FIG. 2).

Example 7

Relative Quantification of Amines in Wild- and Mutant-type *Arabidopsis* with Formaldehyde labeling. The athk1 is a T-DNA insertion that creates a functional knockout in the ATHK1 gene. The T-DNA insertion for the particular mutant that was used is located in the 6th intron. RT-PCR analysis was used to confirm that no ATHK1 transcript can be detected in this mutant.

T-DNA Mutant Screen and Identification. Using a PCR-based strategy, T-DNA mutagenized populations were screened for the presence of insertions in ATHK1. The sequences of primers specific for ATHK1 were: 5' AGGAAG-GTGTTCGATAAAA TGACTGAATG (SEQ ID NO: 1) and 5'-CACATCCAGTATCATCAACCTCAAACCA (SEQ ID NO: 2). The sequences of primers specific for the T-DNA border were: 5'-CATTTTATAATAACGCTGC GGACATC-TAC (SEQ ID NO: 3) and 5'-TTTCTCCATATTGACCAT-CATACTCATTG (SEQ ID NO: 4). DNA sequencing of PCR products confirmed the locations of the junctions of genomic and T-DNA sequences. The 35S construct was created as follows.

Overexpression. A 3.3-kb cDNA fragment containing the entire open reading frame of ATHK1 was overexpressed under the control of the enhanced CaMV 35S promoter. The tobacco mosaic virus Omega sequence was inserted upstream of the ATHK1 sequence to increase the translational level. Wassilewskija (WS) and athk1 plants were transformed (as described herein) for molecular complementation. Transformants were selected with hygromycin (30 mg/mL)(Sigma). Multiple overexpressing lines were identified.

Growth Conditions. Approximately 25 mg of sterilized seeds were sewn in shaker flasks containing 75 mL of liquid MS media (half-strength Murashige and Skoog salts (MS) (Sigma), 2.5 mM MES, 1% sucrose). The seeds were grown with shaking under continuous light. After 7 days growth, 150 mM NaCl or water (control) was added to the flasks and they were grown for another 16 hours. Flasks were harvested individually, dried by blotting on paper-towels, and pooled into samples containing approximately 5 g tissue each. Four replicates for each condition were collected. Samples were flash frozen in liquid nitrogen and stored at −80° until sample extraction.

ATHK1 and Regulation of the Osmotic Stress Response. Understanding osmotic regulation in plants is useful to the production of drought resistant crops. The mechanism that plants use to sense their osmotic environment is unclear. A putative membrane histidine kinase, ATHK1, rescues double knockouts of the known osmolyte sensors in yeast (sln1 and sho1). ATHK1 also activates the high osmolyte glycerol 1 (HOG1) pathway and increase the viability of sln1Δ/sho1Δ knockouts in saline media. These data suggest that ATHK1 may play a central role in osmotic sensing. That role has yet to be established in plants. Several complemented ATHK1 knockout and ATHK1 over-expresser strains in *Arabidopsis thaliana* may be used to elucidate the role of ATHK1 in plant osmotic regulation. ATHK1 knockouts (At) grow more slowly and have a lower germination rate than wild type (wt)

when exposed to high salt media. ATHK1 overexpressors (35s) out-perform wild type in both respects.

One of the functions of the HOG1 pathway is to up-regulate the production of specific organic compounds to offset osmotic imbalance and minimize sodium influx. NMR analysis has demonstrated that several classes of compounds (including betaines, carbohydrates, polyols and amino acids) are involved in osmotic balancing. The concentrations of some osmolytes, such as proline, are upregulated by as much as 10-fold in response to a 250 mM salt stress. ATHK1's putative role as the osmolyte sensor for the plant HOG1 pathway may mean that ATHK1 mutants have altered steady state concentrations of the established osmolytes when the plants are exposed to saline media. Metabolite extracts of At, 35s and wt using a NMR-based metabolomics approach was used to study that mechanism.

Sample Preparation. Wild type (wt), ATHK1 knockout (At) and ATHK1 over-expressing (35s) plants were germinated in sterile liquid cultures of Murashige and Skoog medium and grown for one week under continuous illumination on a shaker platform. After one week, either a sterile sham of Murashig and Skoog medium or NaCl (100 mM final concentration) was added to each culture and allowed to incubate for 32 hours. The experiment was designed with four biological replicates for each of the 6 conditions. After incubation, the plants were removed from their media, washed, and flash frozen in liquid nitrogen. The frozen plant material was lyophilized for 48 hours and ground to a fine powder. 300 mg of each powdered homogenate was added to a 22 ml screw top vial with 16 ml boiling water. Samples were sealed and incubated at 100° C. for 15 minutes. Extracts were then centrifuged at 4,000 g for 30 minutes to pellet the cellular debris and the supernatant was filtered with glass wool to remove suspended particulate matter. A 5,000 molecular weight cut-off vivaspin concentrator was also used.

The filtrate was frozen and lyophilized to a dry powder. The resulting metabolite powder was resuspended on a weight to volume basis with buffered solvent at a ratio of 17.5 µL of buffer per mg of dry extract. The buffer was composed of $D_2O$ with 50 mM NaPO4, 500 µM sodium azide (to minimize microbial growth), and 500 µM DSS. Samples were titrated to an observed pH of 7.400 (+/−0.004) and stored at −80° C. until used.

Figure 9:
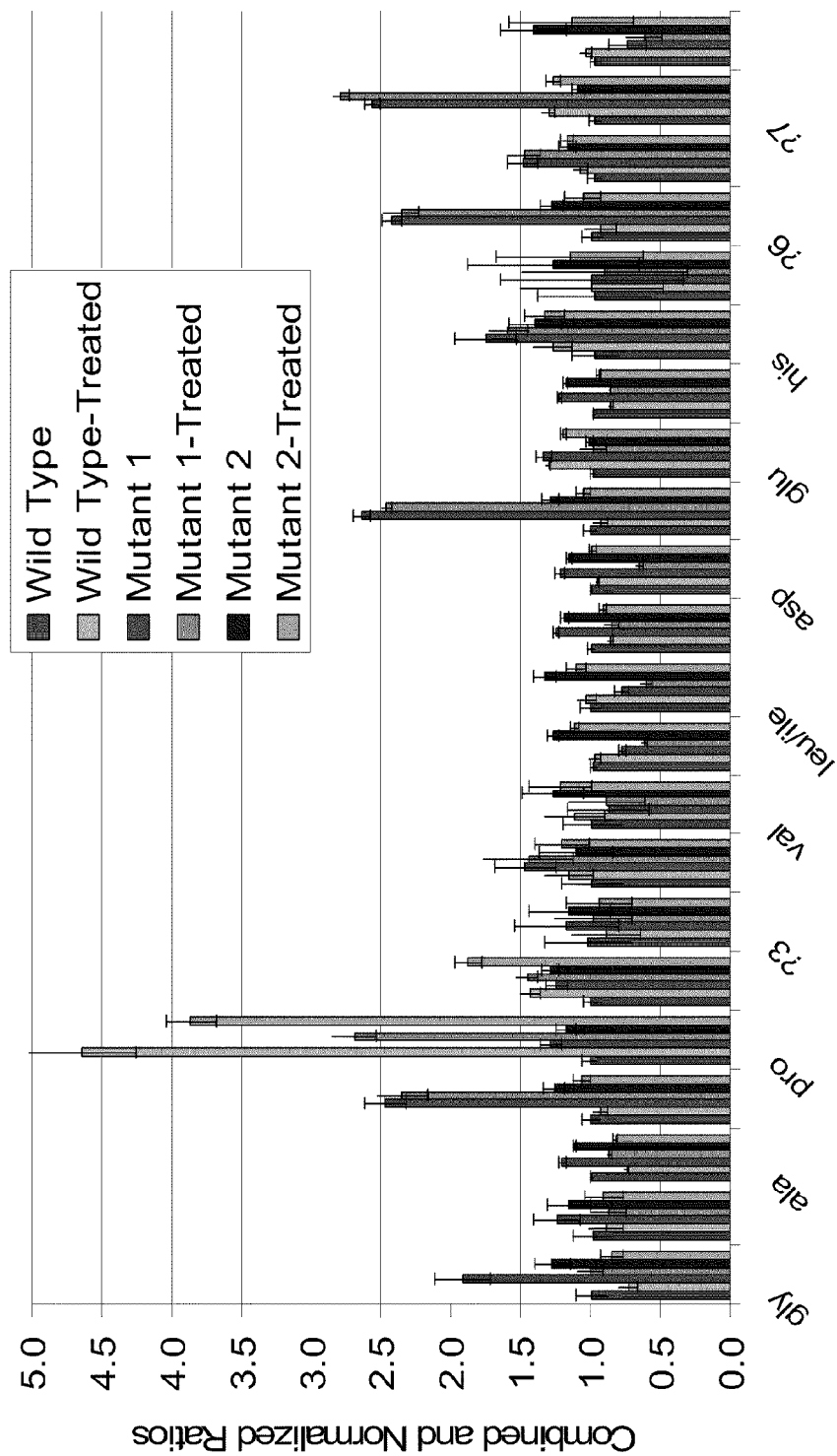
FIG. 9 is a bar graph illustration showing relative quantification of amines in Arabidopsis using formaldehyde, whereby the unknown compounds were identified as labeled products because they have the proper mass-shift, and whereby detection of the unknowns is important because it can reveal unpredicted differences in samples.
Figure 10:
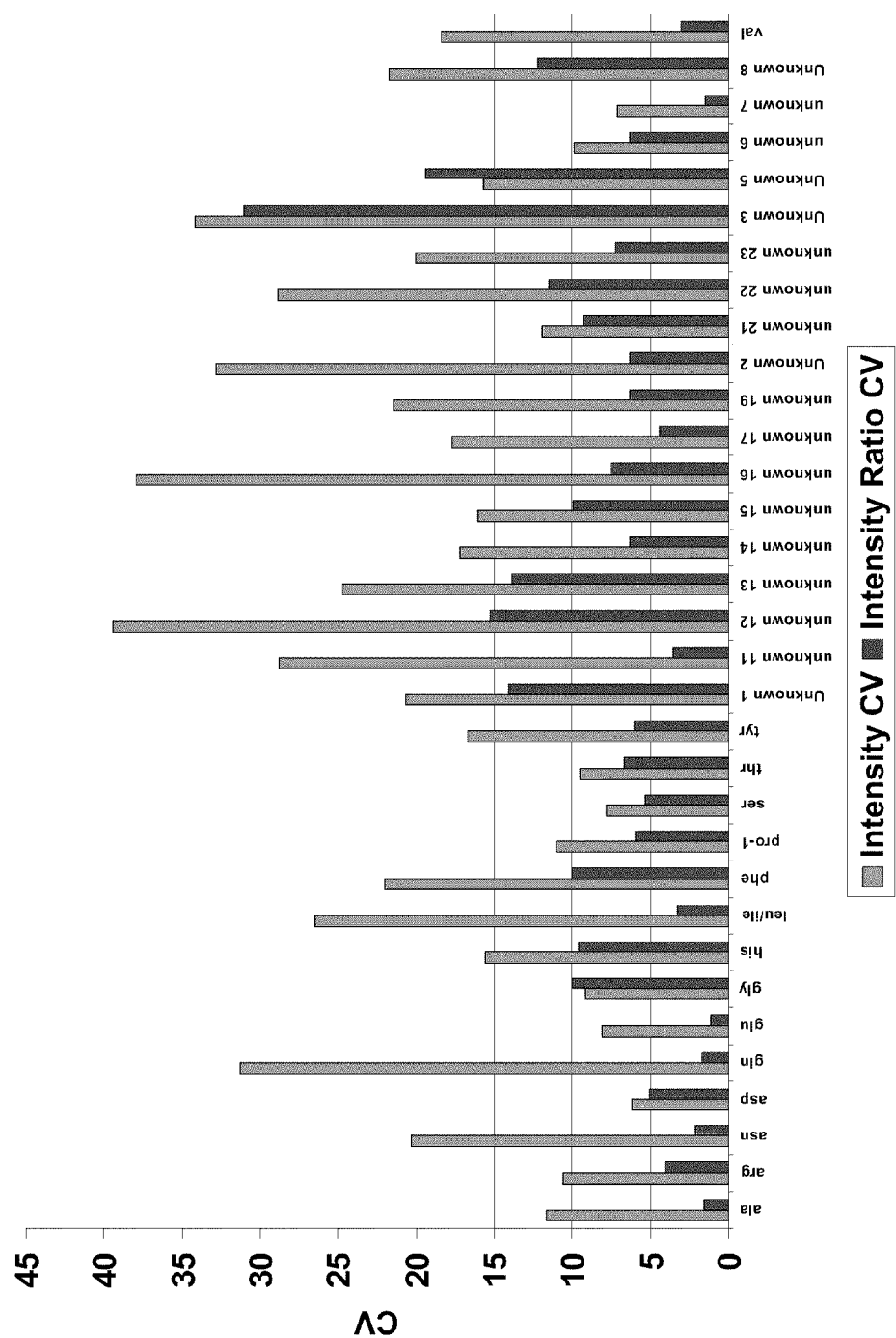
FIG. 10 is a bar graph illustration demonstrating a relative quantification precision comparison of 33 amines in *Arabidopsis* using formaldehyde, whereby the *Arabidopsis* LC-MS data was analyzed to determine the effectiveness of using intensity-only rather than intensity ratio to determine relative abundance, whereby the statistical error (represented as the coefficient of variation, or CV) associated with the intensity-only data and the statistical error associated with the intensity ratio are indicated accordingly, whereby the error is generally lower for the intensity ratio method, whereby the median CV for the intensity-only data is 18% (range 6-39%, average 19%), whereby the median CV for the intensity ratio data is 6% (range 1-31%, average 8%), whereby the unknown compounds were identified as labeled products because they have the proper mass-shift, and whereby detection of the unknowns is important because it can reveal unpredicted differences in samples.

A 25 µL aliquot of extract was taken from each of the six samples, and 1 mL of labeling solvent was added to each sample. Labeling solvent included either 25 µL of 37% aqueous formaldehyde (natural isotopic abundance), 50 µL of pyridine borane, 740 uL of methanol and 185 µL of water, or 46.25 uL of 20% aqueous 13C-formaldehyde, 50 µL of pyridine borane, 723 µL of methanol and 181 µL of water. After reacting overnight, heavy- and light-labeled samples (25 µL each) were mixed and reduced to dryness in a speed-vac. The samples were dissolved in 1 mL of 85:15 acetonitrile:water with 0.1% formic acid and analyzed by HILIC-MS. Compounds with the characteristic mass shift between heavy- and light-labeled forms were identified and their intensity ratios calculated. (See FIG. 9). Treatment included 32 hours with NaCl. Mutant 1 was 35S and mutant 2 was ATHK1.

Example 8

Metabolite Extraction from *Arabidopsis* Plant Tissue. *Arabidopsis* whole plant tissue (9.60 g wet weight) was placed in a 50 mL Falcon tube. Liquid nitrogen was added, and the tissue was crushed to a fine powder using a glass rod. The crushed tissue was mixed with 23 mL of HPLC grade methanol (Burdick Jackson) and 0.80 mL of HPLC grade water (Sigma Aldrich). The mixture was heated at 50° C. for 30 minutes and then sonicated for 15 minutes. The sample was centrifuged at 10,000 rpm for 20 minutes and decanted. The liquid was reduced to dryness in a rotary evaporator and redissolved in 20 mL of methanol. The solution was filtered through 0.2 µm filters (Millex-GV) and aliquoted into 800 µL portions in 1.5 mL centrifuge tubes. The samples were reduced to dryness in a vacuum centrifuge and stored at −40° C.

Figure 4:
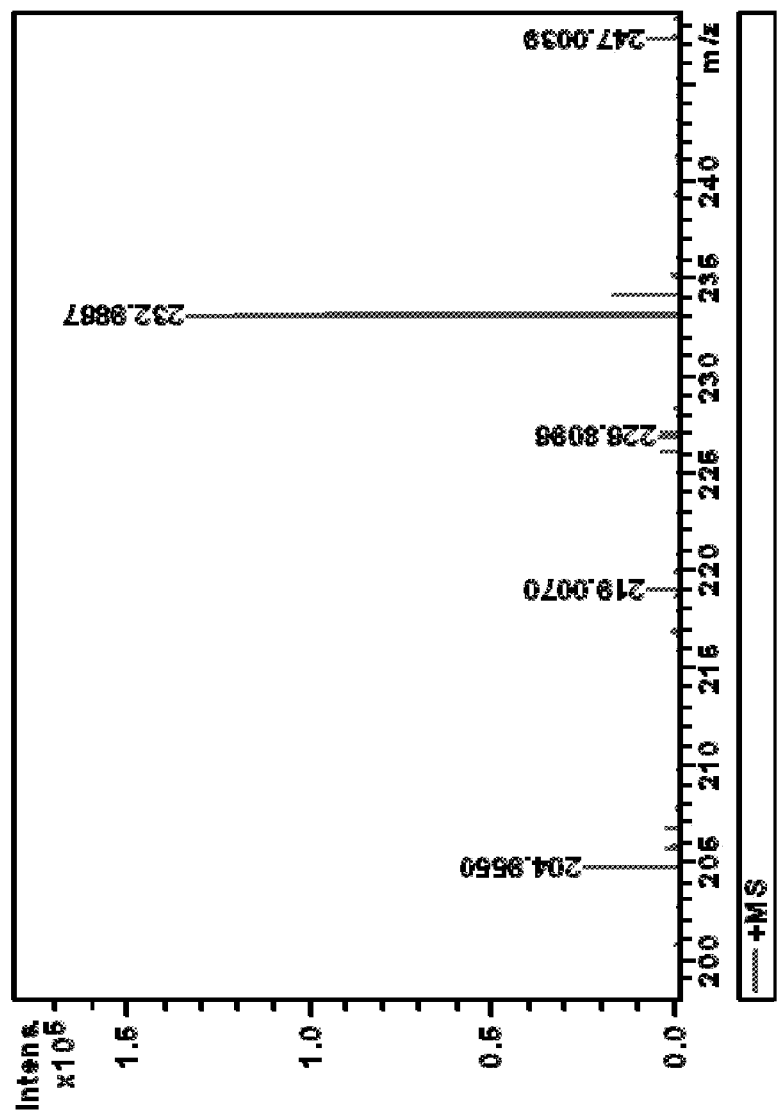
FIG. 4 is a graphical illustration showing an equimolar mixture of labeled and unlabeled tryptophan (dimethyl tryptophan and tryptophan, in equimolar mixture), whereby the intensity of the formaldehyde labeled tryptophan (233 Dalton) is more than 5× that of the unlabeled tryptophan (205 Dalton) by ESI-MS, which demonstrates that formaldehyde labeling enhances signal.

Formaldehyde Labeling of *Arabidopsis* Sample. A previously dried down sample of *Arabidopsis* plant tissue extract (300 µL) was dissolved in 240 µL of MeOH and 60 µL of $H_2O$. Formaldehyde 13.4 M in water (0.67 µL) was added to the stirred suspension giving a final concentration of 30 mM. Borane-pyridine complex 8.0 M (1.9 µL) was added to a final concentration of 50 mM. After 3 h, LC-MS was performed confirming the complete labeling of the amino acids present. In addition, formaldehyde labeling of amino acids also provided sensitivity enhancement. (See FIG. 4). In an experiment performed in the same manner respecting that of methylacetimidate herein (i.e., electrospraying a 1:1 mix of all 8 compounds, 4 labeled and 4 unlabeled), the ionization efficiency increased 7.6, 3.72, 5.15, and 3.95 for Val, Asn, Glu and Trp, respectively. The retention times were slightly shifted in the hydrophobic direction.

Example 9

Figure 11:
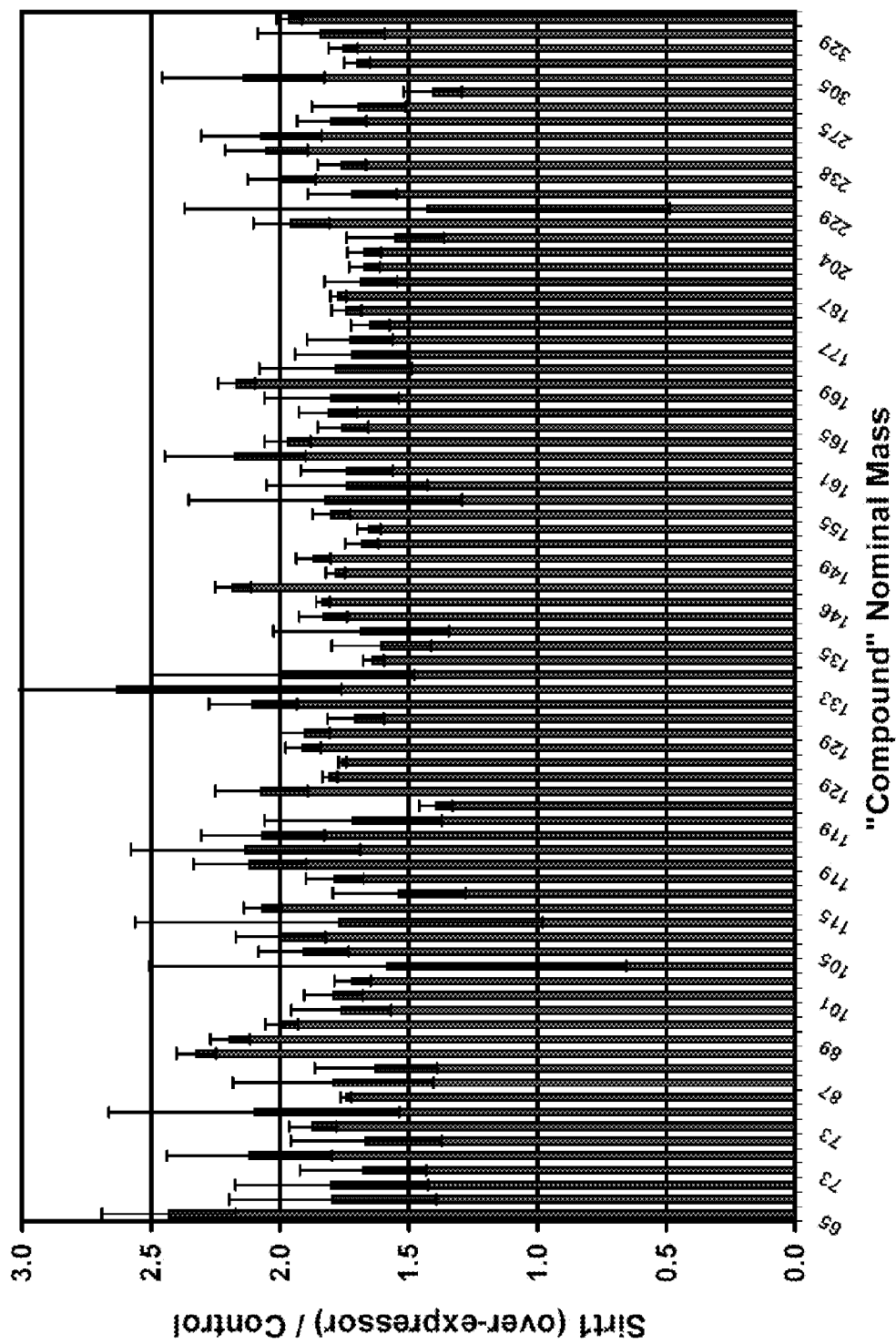
FIG. 11 is a bar graph illustration showing the relative quantification of 83 amines in cell extract having 6 million cells, whereby extracts from one plate of cells (6 million cells) were dissolved in 1 mL of 80:20 methanol:water, whereby 400 μL aliquots were used for labeling, whereby labeling was performed with either heavy or light formaldehyde in the presence of pyridine borane (overnight at room temperature), whereby cells were transfected with either PC DNA (control) or a sirt1 overexpressor, and whereby samples were mixed 1:1 prior to HILIC-MS analysis.
Figure 12:
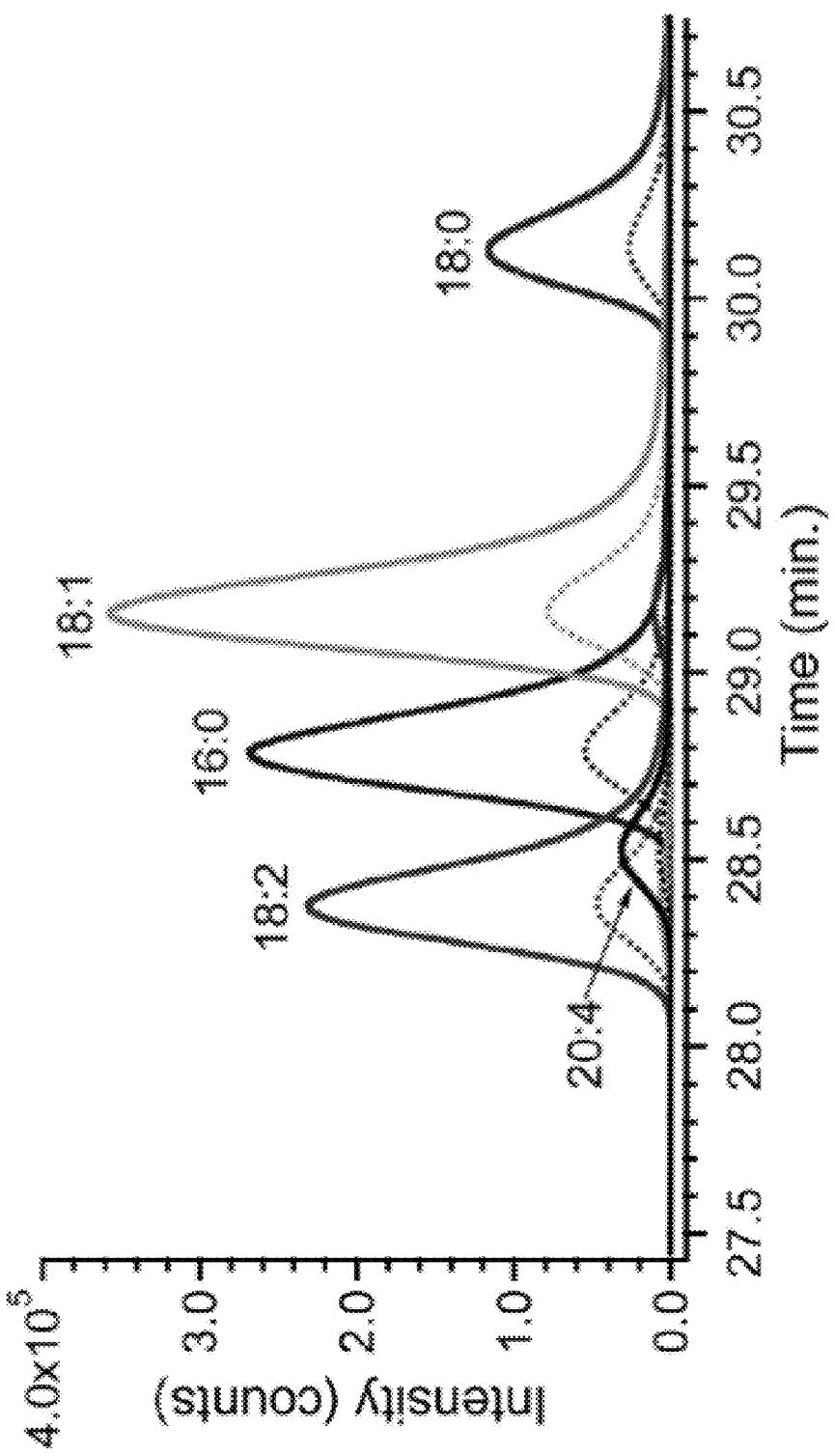
FIGS. 12-15 shows various graphs demonstrating cholamine labeling of fatty acids from egg yolk extract, whereby analysis was performed in acidic buffer with reverse-phase LC and positive-ion mode ESI, whereby the graphs demonstrate that the heavy- and light-labeled products co-eluted due at least in part to the deuteriums being near the quaternary ammonium group, whereby extracted ion chromatograms (FIGS. 12 and 14) and representative mass spectra (FIGS. 13 and 15) of light- and heavy-cholamine labeled fatty acids are shown, whereby the EICs are divided to show the five more abundant fatty acids (FIG. 12) and the five less abundant fatty acids (FIG. 14), whereby co-elution is observed for the isotopic pairs of peaks (dotted and solid lines for light and heavy labels, respectively), whereby the expected 1:4 intensity ratio and the 9 Da shift are also evident, and whereby each compound yields two or three peaks in the mass spectra due to the natural isotopic distribution, but only the tallest (monoisotopic) peak was employed for quantification.
Figure 13:
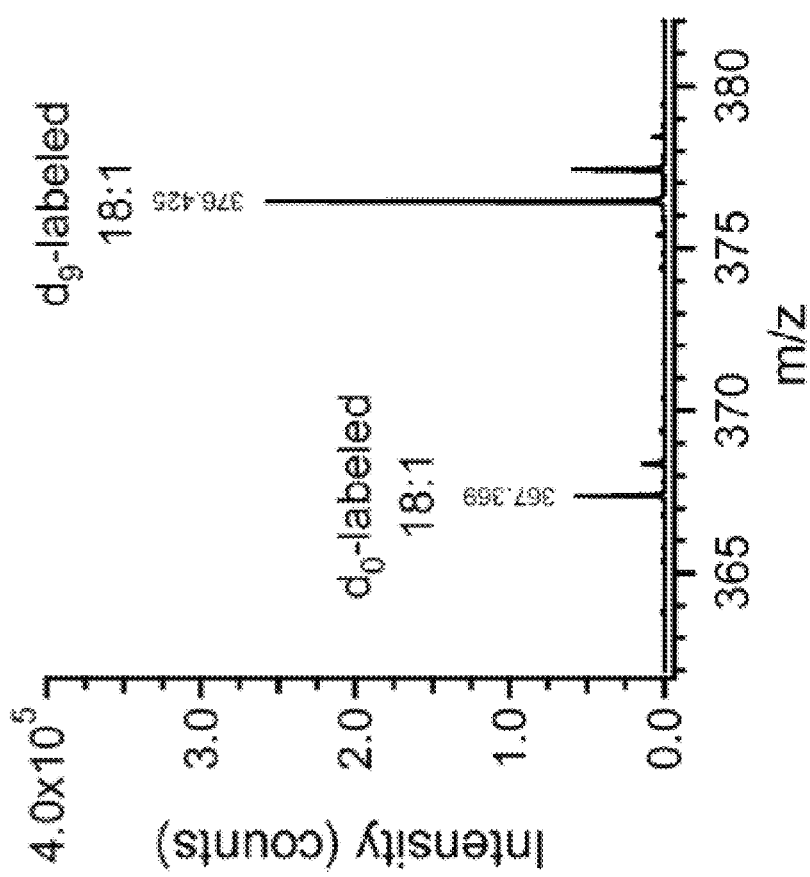
Figure 14:
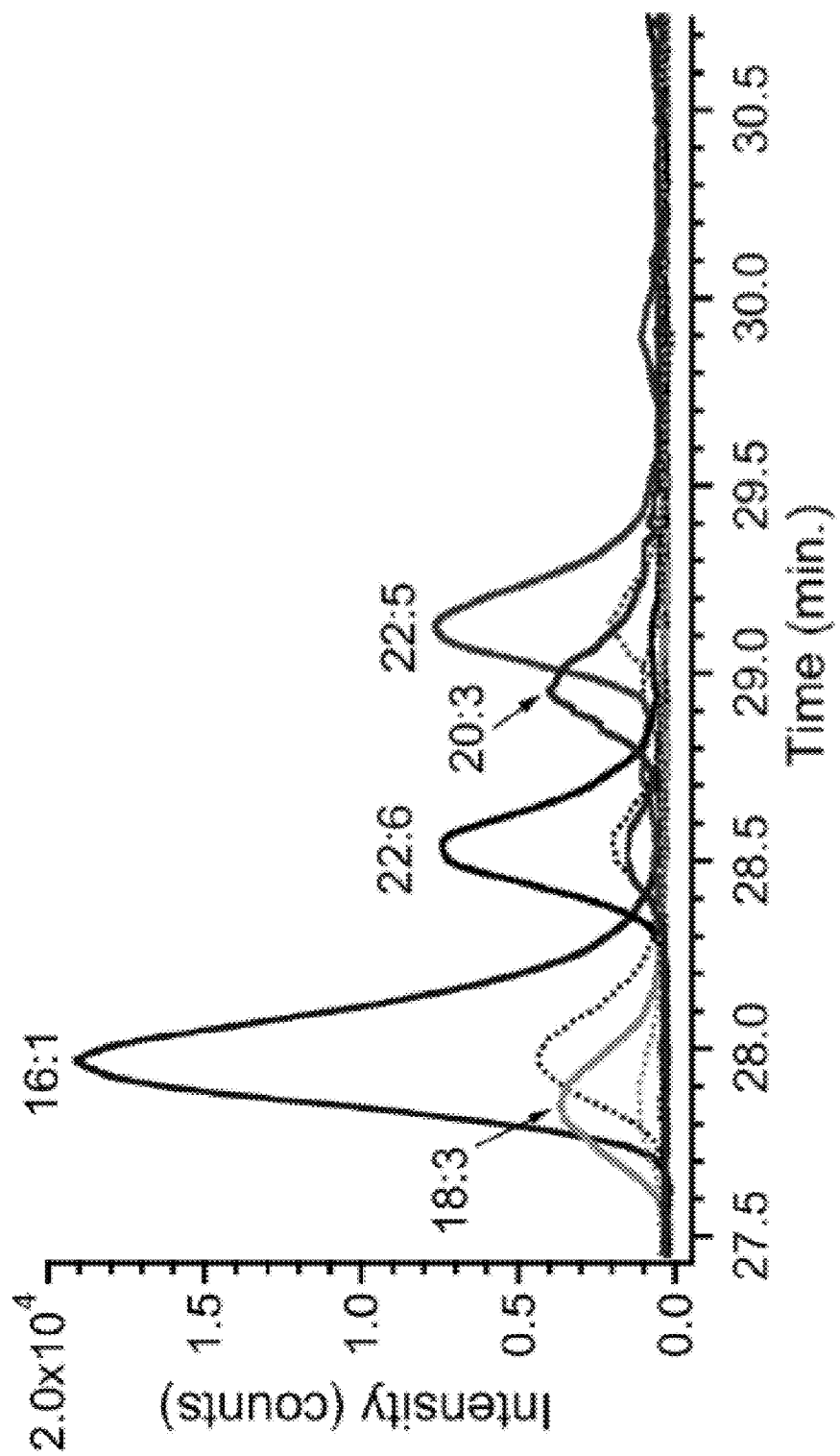
Figure 15:
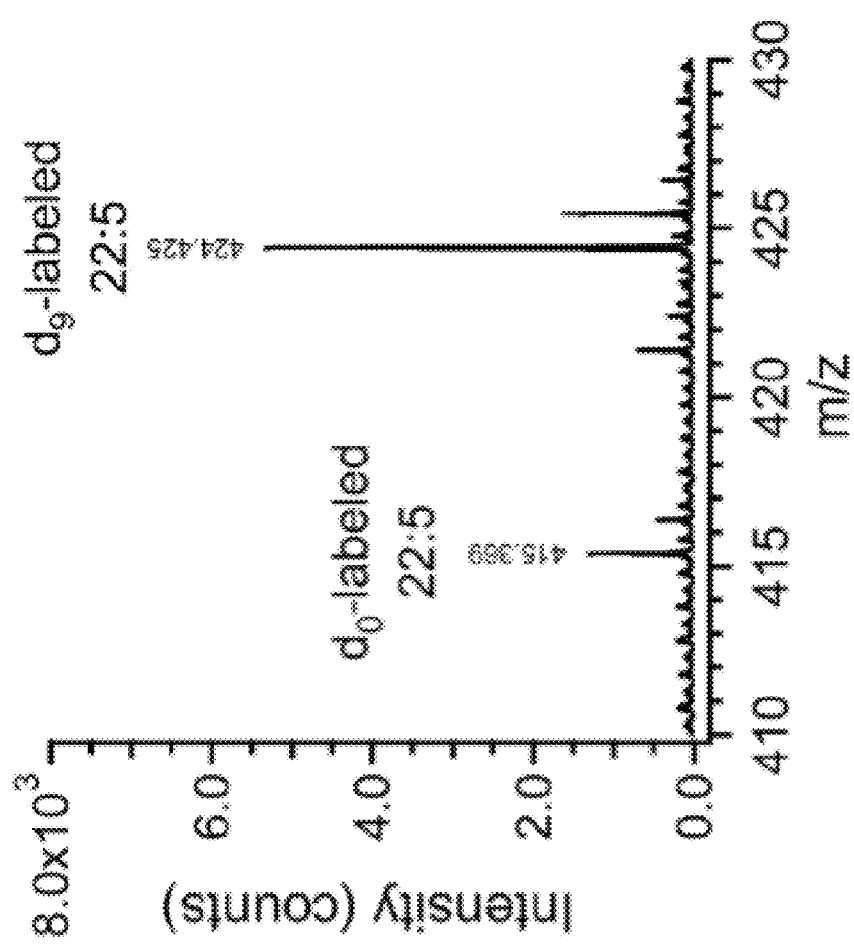
Figure 16:
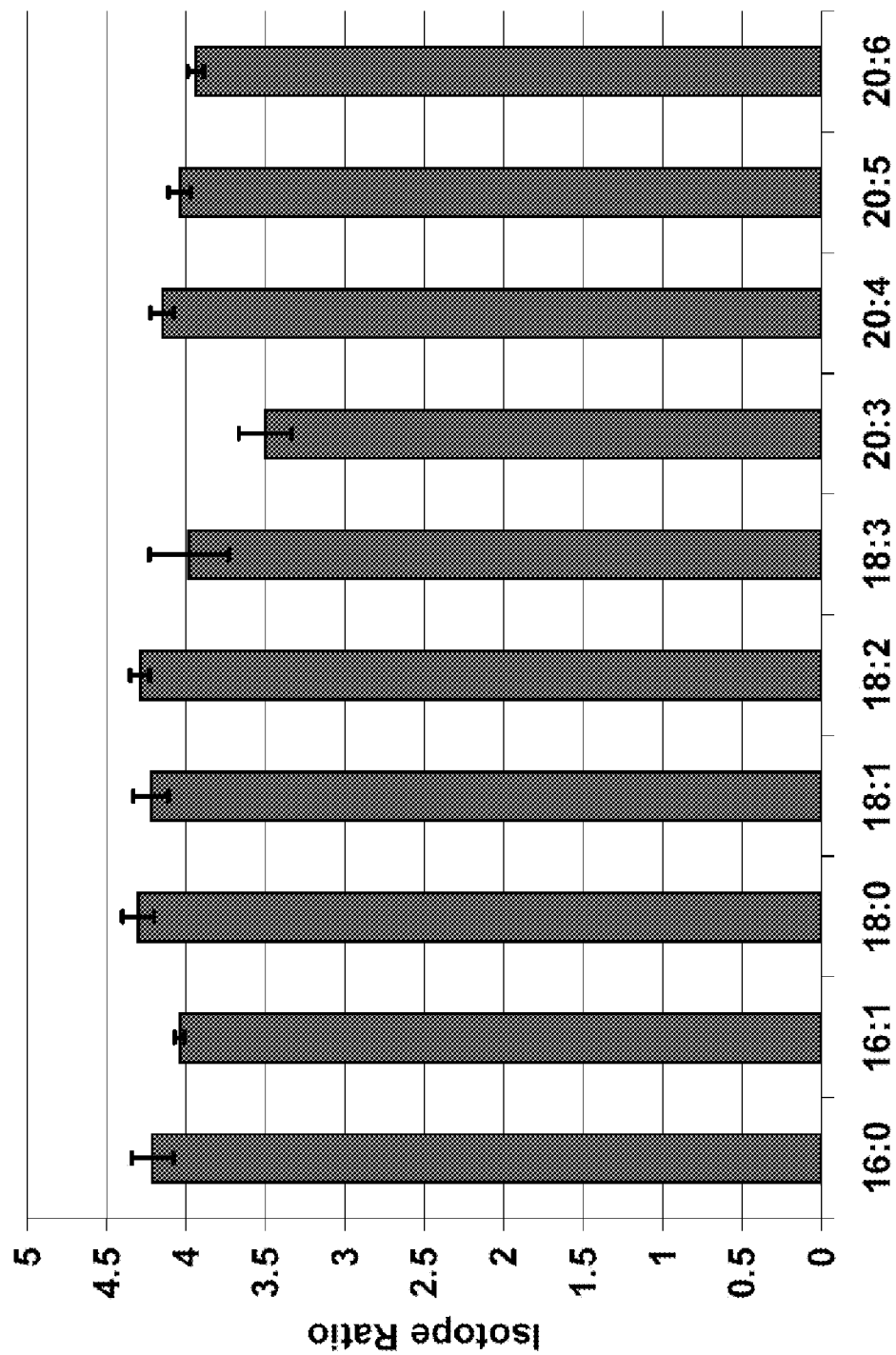
FIG. 16 is a bar graph illustration showing the isotope ratios for fatty acids mixed 4:1, whereby one sample of saponified lipid extract was divided into two equivalent aliquots, whereby one aliquot was labeled with the natural abundance cholamine reagent and the other was labeled with the D9 (heavy isotope) variant of cholamine, whereby the two product solutions were subsequently mixed at a ratio of 4:1, whereby intensity ratios for detected fatty acids (following RPLC-MS) were calculated, and whereby the average=4.07±−0.24, precision (average (CV)=2.6%) and accuracy (% error, average accuracy=4.6%) are demonstrated.

Formaldehyde labeling of HEK cells. HEK293 Transfection and Extraction. Four 10 cm plates of 95% confluent HEK293 cells grown in Dulbecco's Modified Eagle's Minimal Essential Medium (DMEM) supplemented with 10% Fetal Bovine Serum (FBS) were transfected with 10 µg of either pcDNA 3.1 or SIRT1 construct and lipofectamine 2000 (Invitrogen) as described by the manufacturer. Cells were scraped from the plates in 1× Phosphate Buffered Saline (PBS) and pelleted by centrifugation at 600×g for 5 min. and washed with 1×PBS twice. Cells were resuspended in 10 mL of PBS and counted. An equal number of cells from each plate were pelleted. One plate from each transfection was lysed by addition of methanol. The cells were incubated for 10 min. in each solution. The extracts were then centrifuged at 16 kXg to pellet the solids. The supernatant was removed from the pellet and dried by speedvac. The relative quantification data and test results from LC-MS analysis of formaldehyde labeled metabolites are shown in FIG. 11.

Example 10

Synthesis of Cholamine. Sources: Tert-Butyl N-(2-aminoethyl)carbamate was purchased from AK Scientific, Inc. (Palo Alto, Calif.). Methyl iodide-$d_3$ was purchased from Cambridge Isotope Laboratories, Inc. (Andover, Mass.). All Other reagents were obtained from Aldrich Chemical (Milwaukee, Wis.) and used without further purification.

Reaction Methods. All moisture-sensitive reactions were performed in oven-dried glassware under a stream of nitrogen. Bath temperatures were used to record reaction temperatures in all cases. All reactions were stirred magnetically.

Purification and Analysis. Analytical thin-layer chromatography (TLC) was carried out on EM Science TLC plates pre-coated with silica gel 60 $F_{254}$ (250 µm layer thickness). TLC visualization was accomplished using either a UV lamp or charring solutions of ninhydrin or phosphomolybdic acid (PMA). Proton nuclear magnetic resonance ($^1H$ NMR) spectra were recorded at 300 MHz using a Bruker AC+300 spectrometer. Chemical shifts are expressed in ppm relative to residual solvent signal (MeOD-$d_4$, 3.31 ppm). Carbon-13 nuclear magnetic resonance ($^{13}$C NMR) spectra were recorded at 75 MHz using a Bruker AC+300. Chemical shifts are expressed in ppm relative to residual solvent signal (MeOD 49.0 ppm). High-resolution electrospray ionization mass spectra (HRESI-MS) were obtained on either a Micromass LCT or Bruker Daltronics Microtof.

Synthesis of Isotopic Forms of (2-Aminoethyl)trimethylammonium chloride hydrochloride (cholamine-$d_0$ and -$d_9$). Both cholamine isotopic derivatives were prepared in a similar fashion

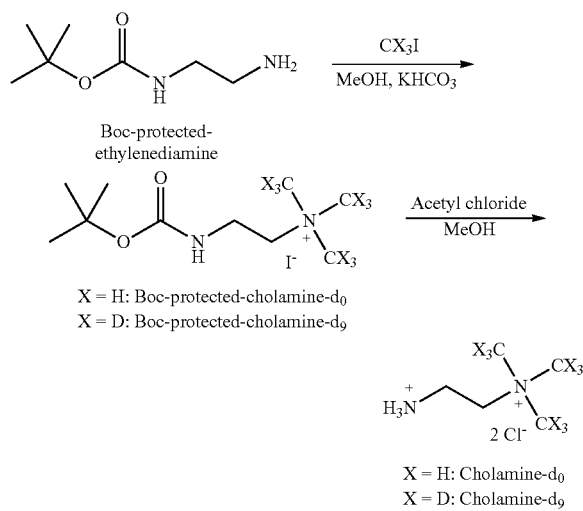

X = H: Boc-protected-cholamine-$d_0$
X = D: Boc-protected-cholamine-$d_9$

X = H: Cholamine-$d_0$
X = D: Cholamine-$d_9$ starting from commercially available Boc-protected ethylenediamine (AK Scientific, Inc.) and reacting with either methyl iodide-$d_0$ or -$d_3$. (The notation $d_x$ is used to indicate that the compound contains x deuterium atoms.). The Boc-protected ethylenediamine (164.9 mg, 1.029 mmol) was added to a stirring solution of methanol (Fisher, 20 mL) and KHCO$_3$ (1.0463 g, 12.454 mmol) at room temperature. After moving the reaction to the dark, methyl iodide-$d_3$ (Cambridge Isotope Labs, 2.275 g, 15.69 mmol) was added. After 18 h, the reaction solution was concentrated, resuspended in CHCl$_3$ (Aldrich, 50 mL), and stirred for 1 h before filtering and concentrating to a viscous oil (~10 mL). The Boc-protected-cholamine-$d_9$ was precipitated by the addition of Et$_2$O(CCl, 70 mL).

The supernatant was decanted and the resulting salts washed again with Et$_2$O (40 mL) before drying in vacuo yielding 194.6 mg (56%) of Boc-protected-cholamine-$d_9$ intermediate as the iodide salt. $R_f$=0.28 (10:2:0.5, DCM:MeOH:NH$_4$OH); $^1$H NMR (MeOD-$d_4$, 300 MHz) δ 3.63 (m, 2H), 3.56 (m, 2H), 3.40 (s, broad, 1H), 1.54 (s, 9H); $^{13}$C NMR (MeOD-$d_4$, 75 MHz) δ 158.11, 80.95, 66.03, 35.85, 28.64 (3C); MS (HRESI-MS) calculated for [C$_{10}$H$_{14}$D$_9$N$_2$O$_2$]$^+$212.2316. found 212.2319. The Boc-protected-cholamine-$d_0$ intermediate was prepared in a similar manner using methyl iodide-$d_0$. Yield 74%. $R_f$=0.28 (10:2:0.5, DCM:MeOH:NH$_4$OH); $^1$H NMR (MeOD-$d_4$, 300 MHz) δ 3.61 (m, 2H), 3.58 (m, 2H), 3.40 (s, broad, 1H), 3.22 (s, 9H) 1.54 (s, 9H); $^{13}$C NMR (MeOD-$d_4$, 75 MHz) δ 158.17, 80.93, 66.30, 54.15 (3C), 35.89, 28.64 (3C); MS (HRESI-MS) calculated for [C$_{10}$H$_{23}$N$_2$O$_2$]$^+$203.1760. found 203.1765.

The Boc-protected-cholamine-$d_9$ intermediate (146.2 mg, 0.4309 mmol) was dissolved in 2 mL of methanol, cooled to 0° C., and acetyl chloride (Aldrich, 173 μL, 2.43 mmol) was added dropwise. After stirring for 3 h, the reaction was diluted with 50 mL of Et$_2$O causing precipitation of an off-white solid. The Et$_2$O was decanted and the salts were washed iteratively with Et$_2$O (3×30 mL) before concentrating in vacuo. Minimal anhydrous acetone was added to dissolve the salts before the addition of 40 mL of Et$_2$O, which again caused the salts to precipitate. The colored mother liquor was decanted and the resulting salts dried in vacuo to give 66.5 mg (84%) of cholamine methyl iodide-$d_9$ as a white chloride salt. $R_f$=0.21 (10:4:1, DCM:MeOH:NH$_4$OH); $^1$H NMR (MeOD-$d_4$, 300 MHz) δ 3.73 (m, 2H), 3.50 (m, 2H), 3.30 (s, broad, 1H); $^{13}$C NMR (MeOD-$d_4$, 75 MHz) δ 62.44, 34.21; MS (HRESI-MS) calculated for [C$_5$H$_6$D$_9$N$_2$]$^+$ 112.1800. found 112.1817. Cholamine-$d_0$ was prepared in a similar manner. Yield 91%. $R_f$=0.21 (10:4:1, DCM:MeOH:NH$_4$OH); $^1$H NMR (MeOD-$d_4$, 300 MHz) δ 3.76 (m, 2H), 3.51 (m, 2H), 3.29 (s, broad, 9H); $^{13}$C NMR (MeOD-$d_4$, 75 MHz) δ 62.71, 54.30 (3C), 34.27; MS (HRESI-MS) calculated for [C$_5$H$_{15}$N$_2$]$^+$ 103.1235. found 103.1244.

Example 11

Animal Protocol and Lipid Extraction from Egg Yolk. Single-comb white Leghorn individually-housed hens each were assigned to one of five dietary regimens: a supplement of 3.5% olive oil (OO), or a supplement of 3.5% safflower oil (SO), or each of these with 0.5% conjugated linoleic acid (OO-CLA and SO-CLA, respectively), or a standard table diet as a control. Following established protocols, egg lipids were extracted and hydrolyzed to free fatty acids. Twelve milliliters of 2:1 chloroform:methanol was used to extract lipids from 3 g of egg lipid. A 1 mL aliquot of egg lipid was placed into a 20 mL vial followed by addition of 5 mL of 9:1 acetonitrile:5M HCl. The solution was refluxed until hydrolysis was complete, as visualized by the complete dissolution of the oil layer. Samples were taken to near dryness on a rotary evaporator, followed by complete drying with a vacuum pump.

Labeling of Chicken Egg Fatty Acid Metabolites with Cholamine. Chicken egg fatty acid extracts were dissolved in 5 mL of dimethyl sulfoxide (DMSO, Sigma). Aliquots (50 μL each) were treated sequentially with 125 μL of 20 mM 1-hydroxybenzotriazole (HOBt, Aldrich) in DMSO; 50 μL of 100 mM cholamine-$d_0$ or -$d_9$ in DMSO containing 200 mM triethylamine (TEA, Aldrich); and 125 μL of 20 mM 2-(1H-benzotriazole-1-yl)-1,1,3,3-tetramethylaminium hexafluorophosphate (HBTU, Novabiochem) in DMSO. The samples were left to react overnight before being dissolved (1:100) in 75:25 water:acetonitrile with 0.1% formic acid. Heavy and light labeled samples were mixed 1:1 unless otherwise stated. Injection volumes of 2 μL from each mixture were analyzed by LC-MS as described below.

LC-MS Analysis. The HPLC system consisted of an LC Packings Famos auto-sampler and UltiMate solvent pump (Dionex Corporation, Sunnyvale, Calif.). A 150×0.300 mm, C18 PepMap 100 capillary column (Dionex Corporation, Sunnyvale, Calif.) with 3 μm particle size and 100 Å pore-size was used for separation of the analytes. The 38 minute binary gradient elution profile was as follows: t=0, 25% B; t=5, 25% B; t=17, 100% B; t=27, 100% B; t=28, 25% B; and t=38, 25% B. Mobile phase A was 0.1% formic acid (EM, Gibbstown, N.J.) in HPLC grade water (Burdick & Jackson, Morristown, N.J.) and mobile phase B was 0.1% formic acid in HPLC grade acetonitrile (Burdick & Jackson, Morristown, N.J.). The flow rate was 4 μL/min and sample injection volumes were 1 μL. The LC effluent was directed to the capillary electrospray ionization source of a MicrOTOF time-of-flight mass spectrometer (Bruker Daltonics, Billerica, Mass.). Positive-ion mode electrospray was performed at a potential of 4500 V using 0.4 bar of $N_2$ as a nebulizer gas and 4.0 L/min of $N_2$ drying gas at 150° C.

Simulated Relative Quantification of Fatty Acids. Two identical samples of fatty acids from hydrolyzed egg lipid extract were reacted with either the heavy or the light form of cholamine as described herein. The two product solutions were subsequently mixed in ratios of 1:4 and 4:1 to simulate relative quantification. These mixtures were separated by reverse-phase HPLC followed by ESI-MS. Data from the 1:4 mixture is shown in FIGS. 12-15. Extracted ion chromatograms (EICs) were obtained for the masses corresponding to the heavy- and light-labeled versions of ten fatty acids. Chromatographic co-elution of the heavy- and light-labeled fatty acids is clearly demonstrated by the EICs. Example mass spectra are shown for two fatty acids, one with high abundance and the other with low abundance, whereby these spectra illustrate the 9 Da mass-shift between the heavy and light forms. The ratios of peak intensities were calculated for each pair of heavy- and light-labeled fatty acids from four runs (i.e., 2 runs each of the 1:4 and 4:1 mixtures) and the average ratios are shown in Table 1.

TABLE 1

| Fatty Acid[a] | Experimental Ratio[b] | Precision CV (%) | Accuracy \|% error\| |
|---|---|---|---|
| 16:0 | 4.21 | 3.1 | 5.4 |
| 16:1 | 4.04 | 0.8 | 1.1 |
| 18:0 | 4.30 | 2.3 | 7.5 |
| 18:1 | 4.22 | 2.6 | 5.5 |
| 18.2 | 4.29 | 1.4 | 7.4 |
| 18:3 | 3.98 | 6.3 | 0.6 |
| 20:3 | 3.50 | 4.8 | 12.5 |
| 20:4 | 4.15 | 1.8 | 3.7 |
| 22:5 | 4.04 | 1.7 | 1.0 |
| 22:6 | 3.94 | 1.3 | 1.4 |
| Average | 4.07 | 2.6 | 4.6 |

[a]Fatty acids are referred to by their number of carbons and degree of unsaturation.
[b]A 1:1 mixture was used to normalize ratios for minor variations in reactivity between heavy and light cholamine.

The average experimental ratio for the ten fatty acids was 4.07 compared with an expected ratio of 4.00. The accuracy and precision were very good for this simulated relative quantification experiment: average absolute error was 4.6% and the average CV was 2.6%.

Attributes of Cholamine as an Isotopic Labeling Reagent. Cholamine has a number of advantages as a labeling reagent. The product of the reaction between cholamine and a carboxylic acid contains a permanently ionized quaternary ammonium group. Not only is the ionizability of the acid not destroyed during the coupling reaction, but the mode of ionization switches from negative to positive mode, which facilitates the use of acidic buffers during the LC separation. The reaction conditions are such that no sample clean-up is required. The product-containing solution is simply diluted with LC loading buffer, separated into its components by chromatography, and then mass analyzed. The size and mass of the label is smaller than the targeted analytes, and the added mass for the light and heavy labels are 85 Da and 94 Da, respectively. Thus, the chemical structures of the original analytes contribute significantly to the chromatographic separation. (See FIGS. 12-15).

In other words, the label does not dominate the separation and cause all labeled compounds to elute at the same time. That could increase detection limits because of ion suppression effects thereby impairing observation of some minor constituents. The placement of the deuterium on the methyl groups of the quaternary ammonium group, rather than at some more hydrophobic position, ensures co-elution of light- and heavy-isotope derivatives of equivalent metabolites from two different samples. (See FIGS. 12-15). In contrast, some deuterium isotope derivatives that are used in relative quantification of peptides produce an undesirable chromatographic shift, which introduces a source of error in calculation of relative abundances. The relatively large 9 Da shift between the light- and heavy-labeled compounds also prevents the natural isotope peaks of the light-labeled compound from overlapping with the monoisotopic peak of the heavy-labeled compound.

Relative Quantification of Fatty Acids from Hydrolyzed Egg Lipid. Dietary lipid kit can have significant effects on the growth and kit of chickens and their eggs. For example, animals fed conjugated linoleic acid (CLA) exhibit improved growth, efficiency of food use, and resistance to certain diseases. But, the CLA diet also leads to dramatic decreases in egg hatchability. It has been reported that combining other fatty acids with CLA eliminates the hatchability problem. (Aydin R et al., *Journal of Nutrition* 2001, 131, 800-806). These fatty acids in the diet impact the fatty acid kit of the eggs, which affects hatchability. The example herein used cholamine labeling for relative quantification of fatty acids in egg lipids in order to examine the incorporation of dietary fat into egg yolks.

Figure 17:
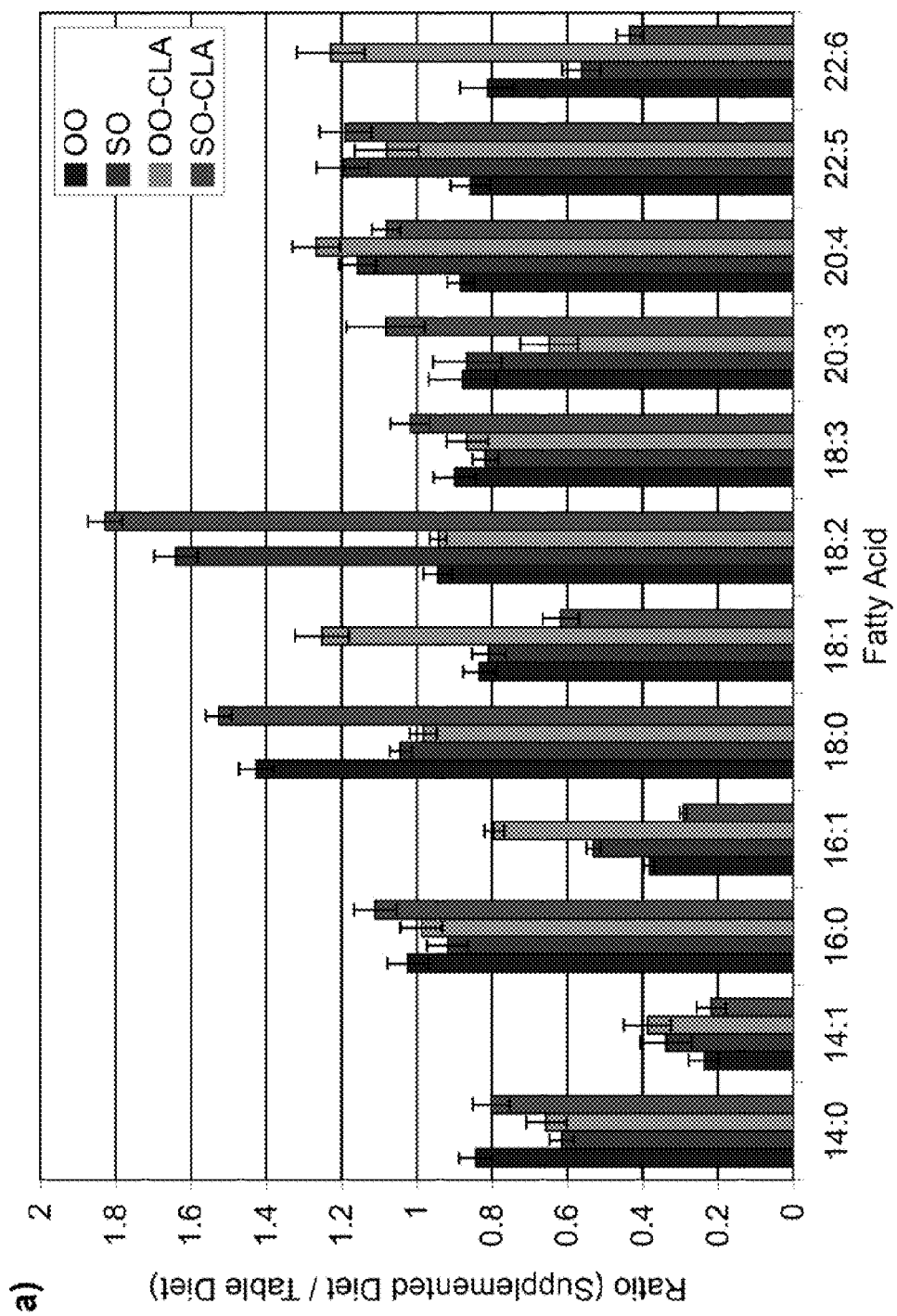
FIG. 17 is a bar graph illustration showing relative quantification (isotope labeling ratio) of fatty acids in hydrolyzed egg lipid extracts from chickens on various diets, whereby the relative quantification results from heavy- and light-isotopic labeling with cholamine are displayed as ratios.
Figure 18:
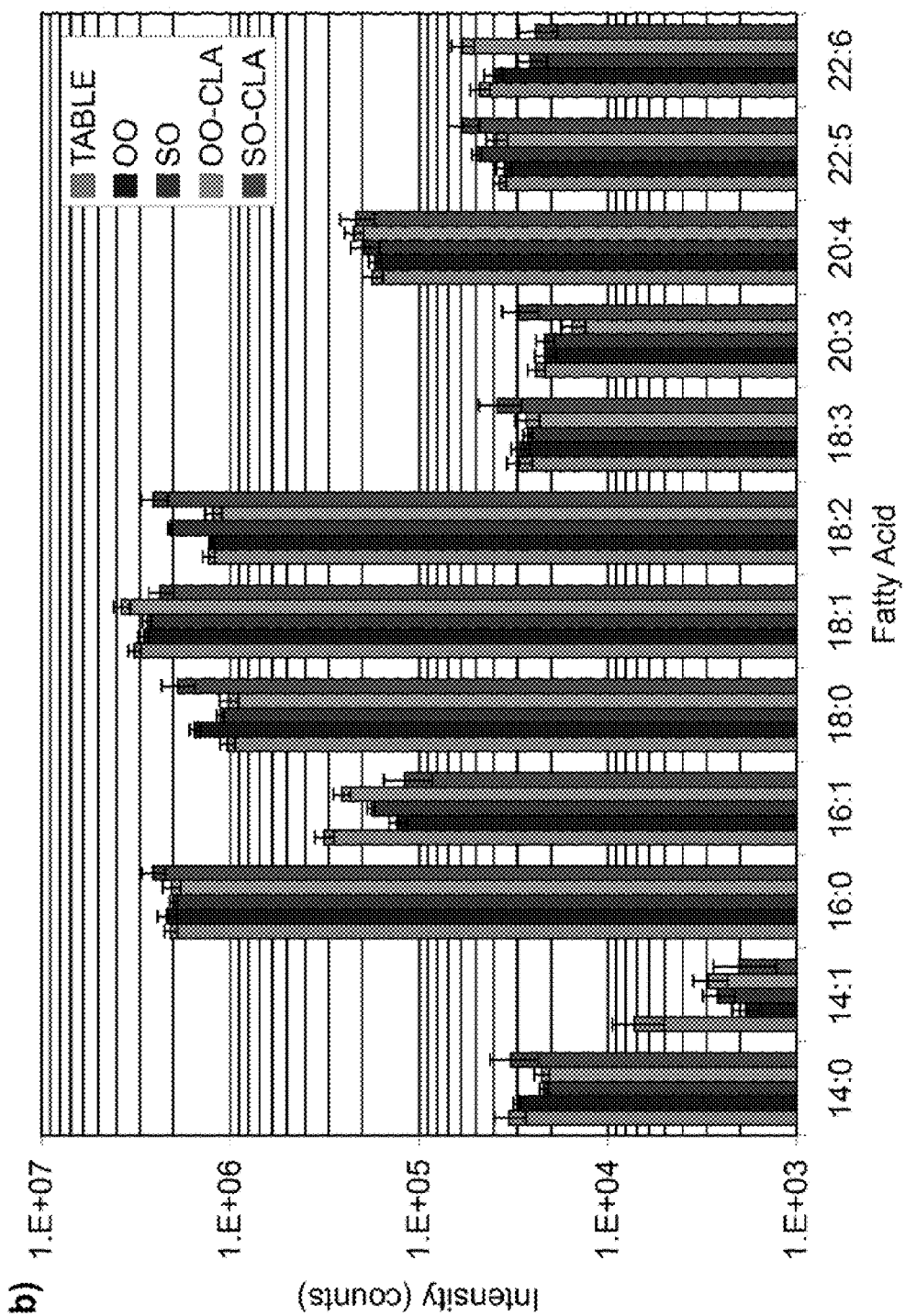
FIG. 18 is a bar graph illustration showing signal intensities for cholamine-labeled fatty acids in hydrolyzed egg lipid extracts from chickens on various diets, whereby the log plot of absolute intensities of labeled fatty acids shows a dynamic range of 3 orders of magnitude.

The data shown in FIGS. 17 and 18 illustrate the fatty acid analysis of egg lipids after supplementing the standard table diet with olive oil (OO) and safflower oil (SO), with and without CLA. The various supplemented diets are all compared to the standard table diet. A ratio of 1.0 in FIG. 17 indicates that the supplement had no effect on the amount of that particular fatty acid. Many substantial changes in the fatty acid kit are observed. The error bars in FIGS. 17 and 18 represent the standard deviations obtained from two LC-MS runs for each of two cholamine labeling experiments (i.e. four technical replicates). The median CV across the 12 different fatty acids was 6% (range of 2-20%) for this relative quantification experiment using isotope labels.

Quantification by LC-MS without labels or isotopic standards typically involves a simple comparison of peak intensity/area between runs. However, this method is generally less precise due to variations in run-to-run retention times and ionization efficiency. This effect is demonstrated by an alternate analysis of the intensity data. (See FIG. 18). Ratios of peak intensities for each compound between different LC-MS runs were calculated, and the median CV in that case was 12% (range of 2-36%). In contrast, ratioing isotopic peak intensities within a single run using the isotopic labeling approach described herein significantly improves the precision of relative quantification median CV of only 6% (range of 2 to 20%).

Chemical derivatization with cholamine facilitates LC-MS analysis of fatty acids by greatly enhancing positive mode electrospray ionization after reverse-phase separation under acidic conditions. Metabolite identification was not problematic for the dozen or so fatty acids of interest in these egg lipid samples, but metabolite database searching for other types of samples could be improved by pairing the knowledge of a carboxylic acid functional group with a metabolite mass. The strategy of isotopic labeling with cholamine assures precise relative quantification without the possibility that matrix effects or run-to-run variations might adversely and unknowingly affect the results. Cholamine labeling is suitable for other carboxylic acid-containing metabolites (such as small polar metabolites) as well as other types of samples such as lysates from cultured cells.

Example 12

Figure 19:
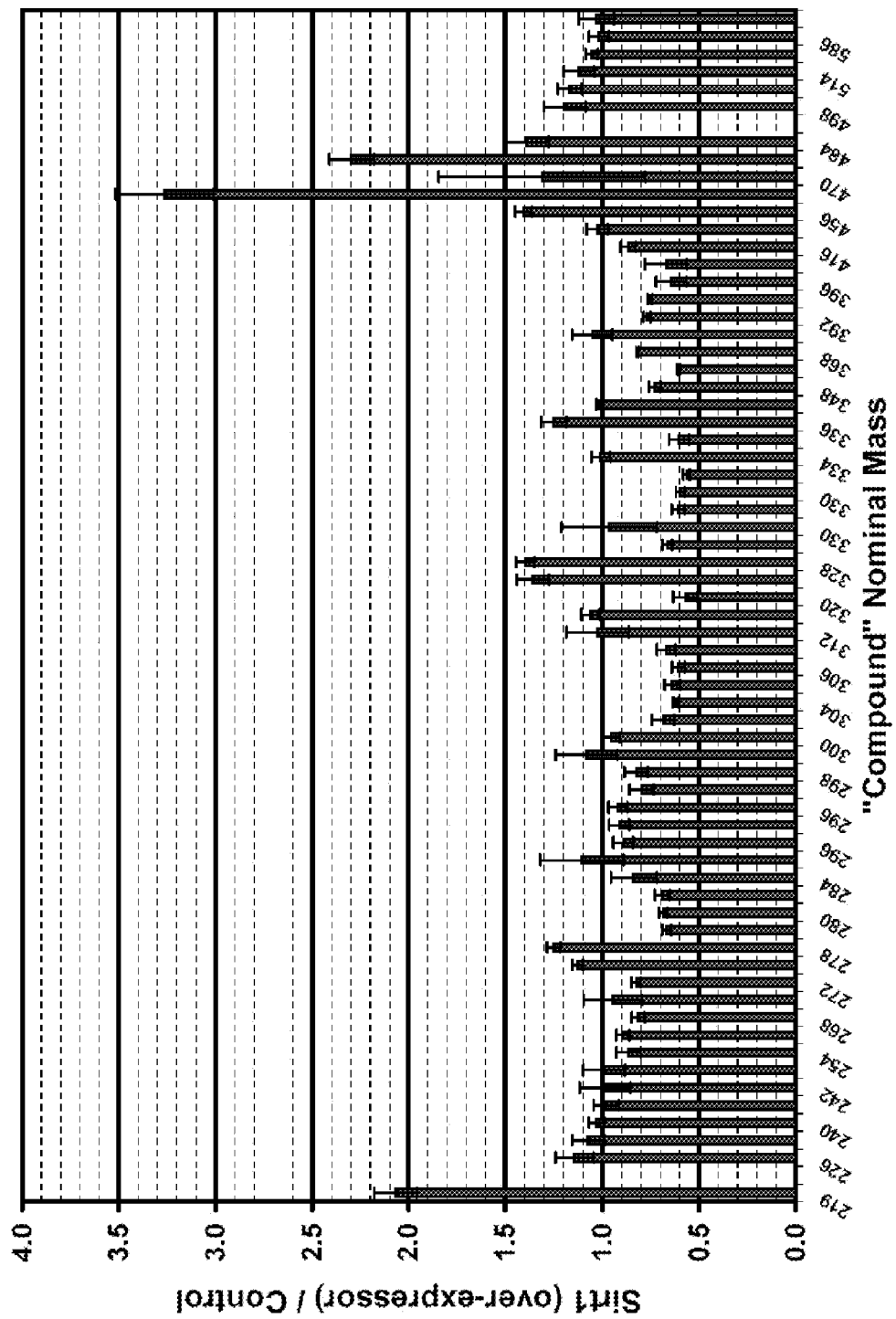
FIG. 19 is a bar graph illustration showing relative quantification of 69 carboxylic acids in cell extract, whereby chloroform extracts from one plate of cells (6 million cells) were employed, whereby labeling was performed with either heavy or light cholamine in the presence of TEA, HOBt, and HBTU (overnight at room temperature), whereby cells were transfected with either PC DNA (control) or a sirt1 overexpressor, and whereby samples were mixed 1:1 prior to RPLC-MS analysis.
Figure 20:
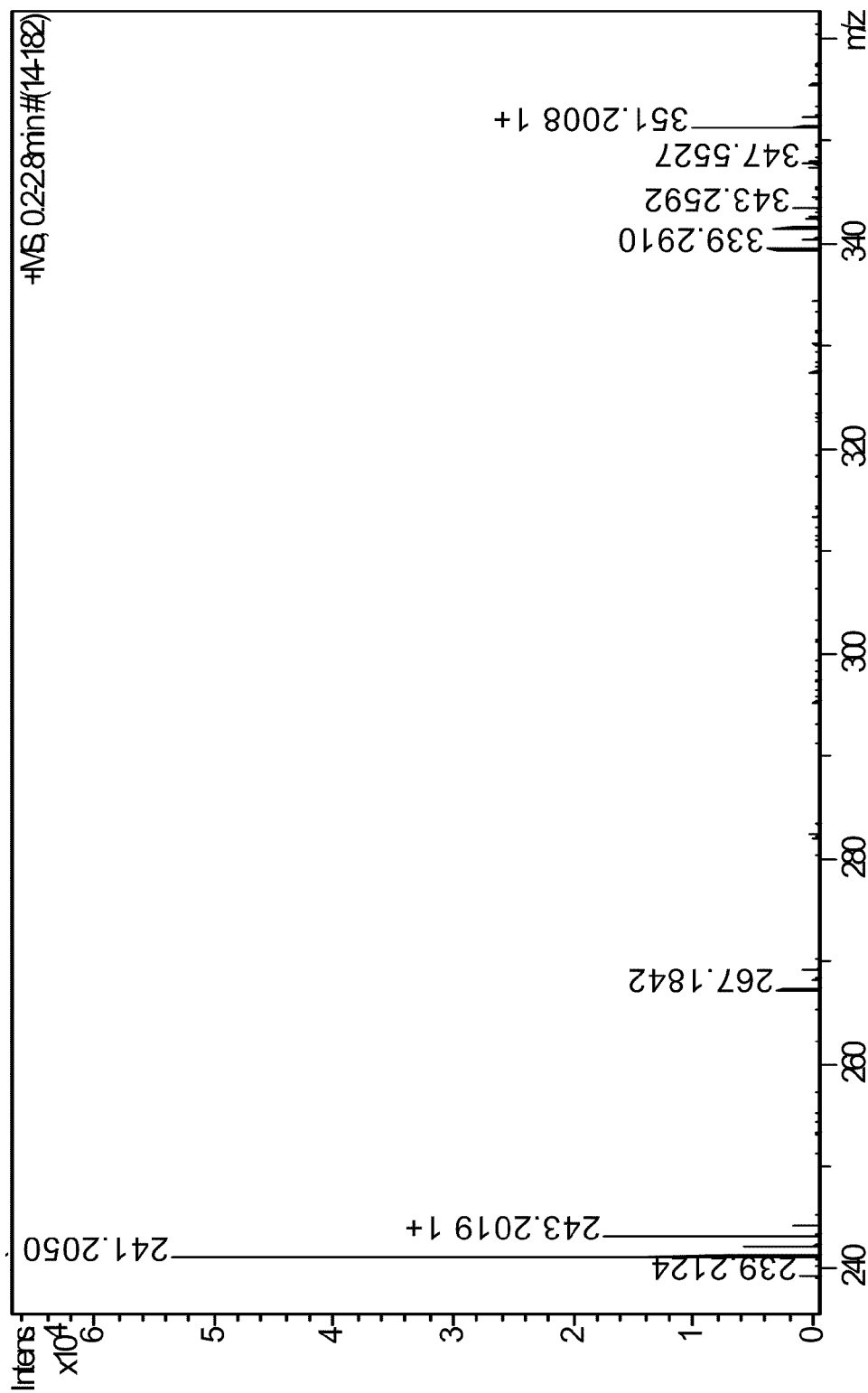
FIGS. 20, 21, 22, 23 and 24 show mass spectra for a sample of the peptide neurotensin after labeling with cholamine, whereby each spectrum shows a different m/z region.
Figure 21:
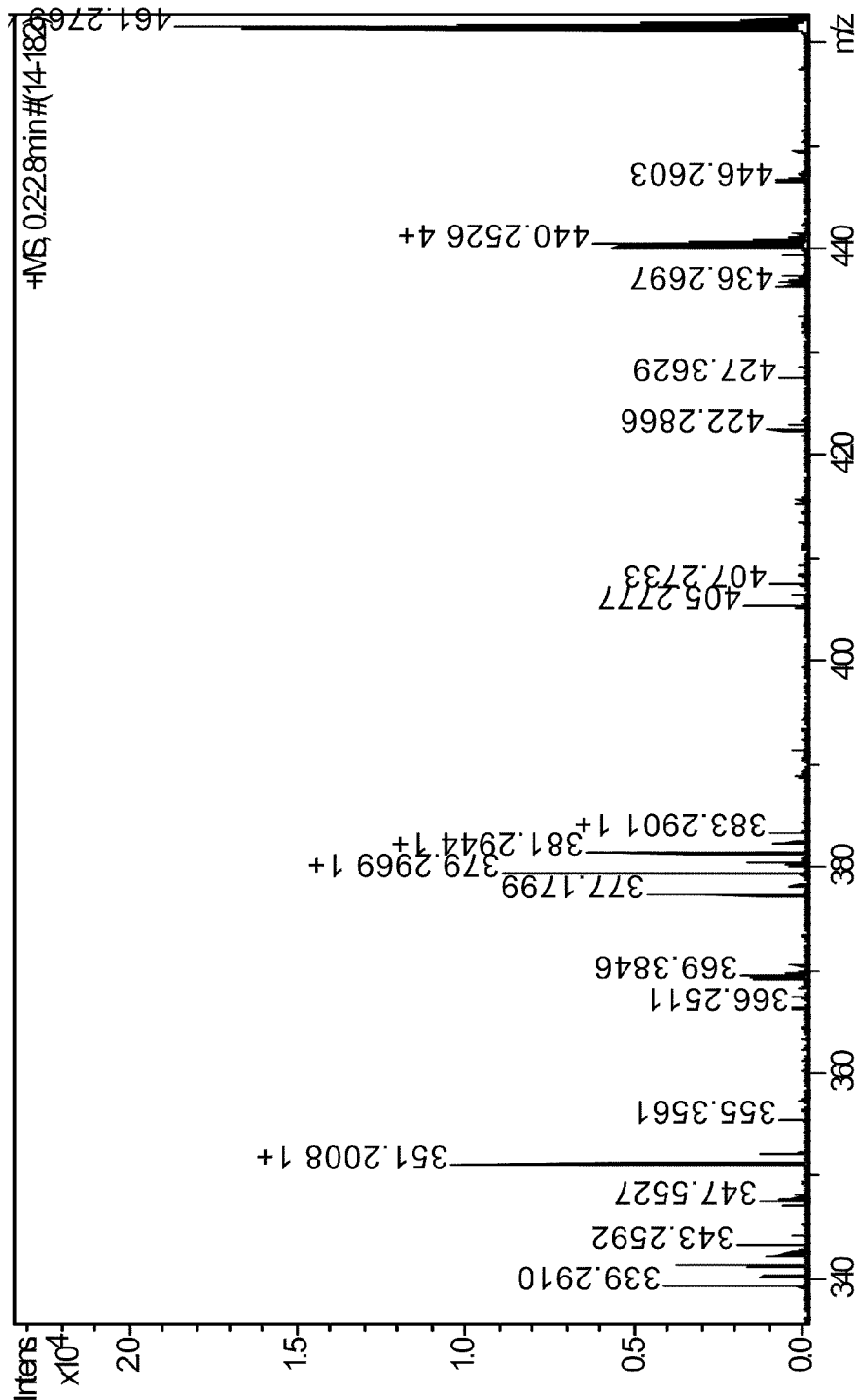
Figure 22:
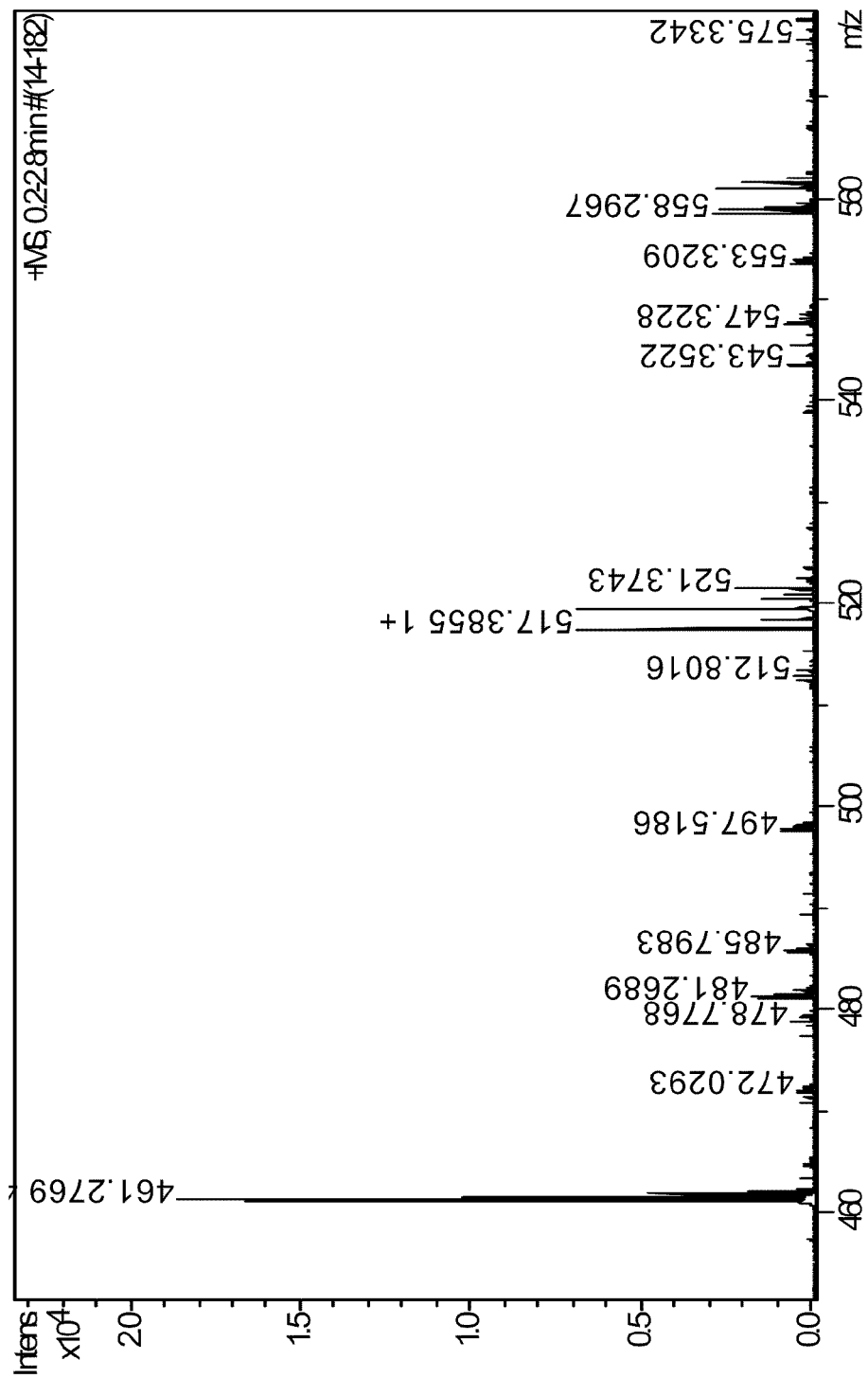
Figure 23:
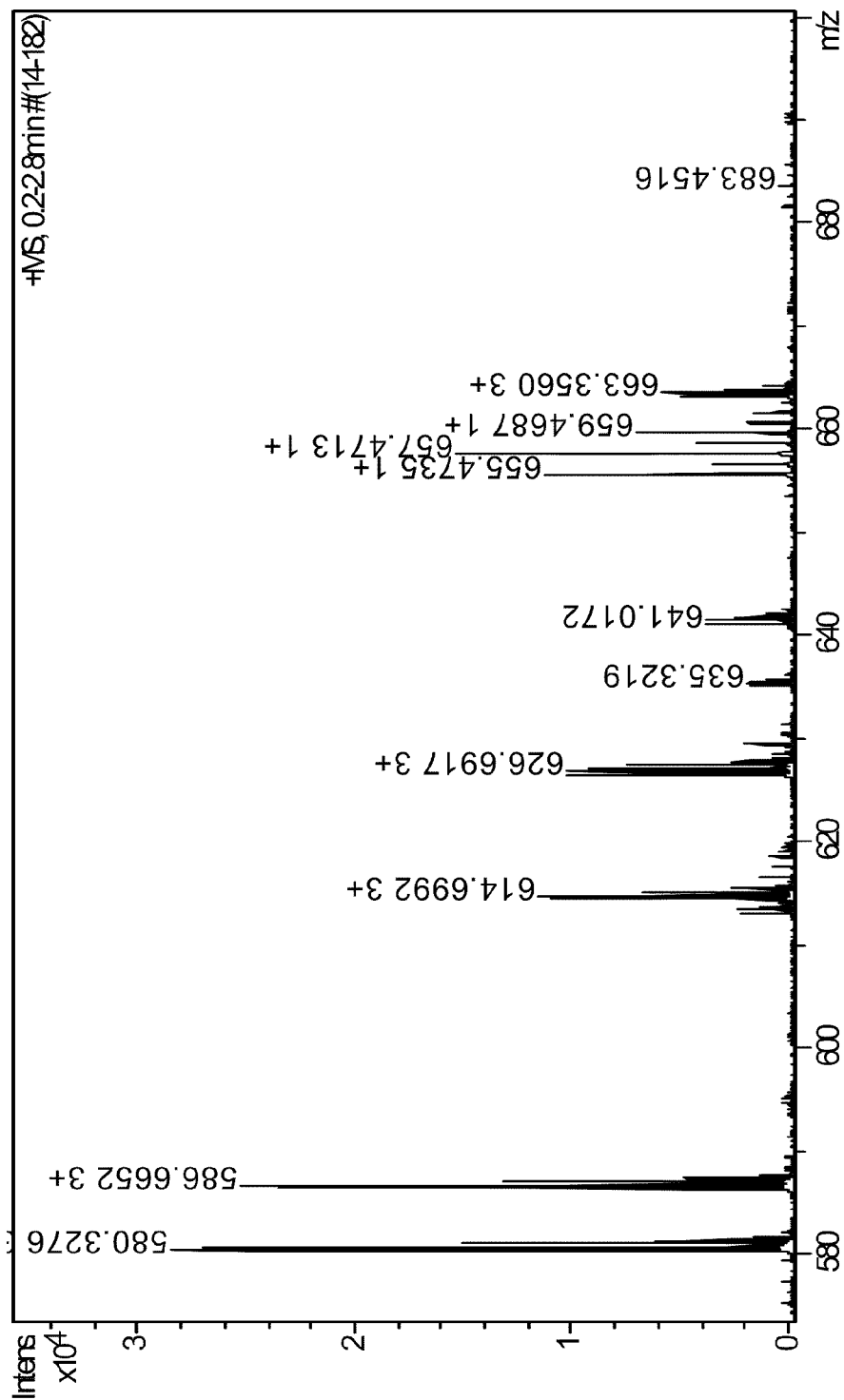
Figure 24:
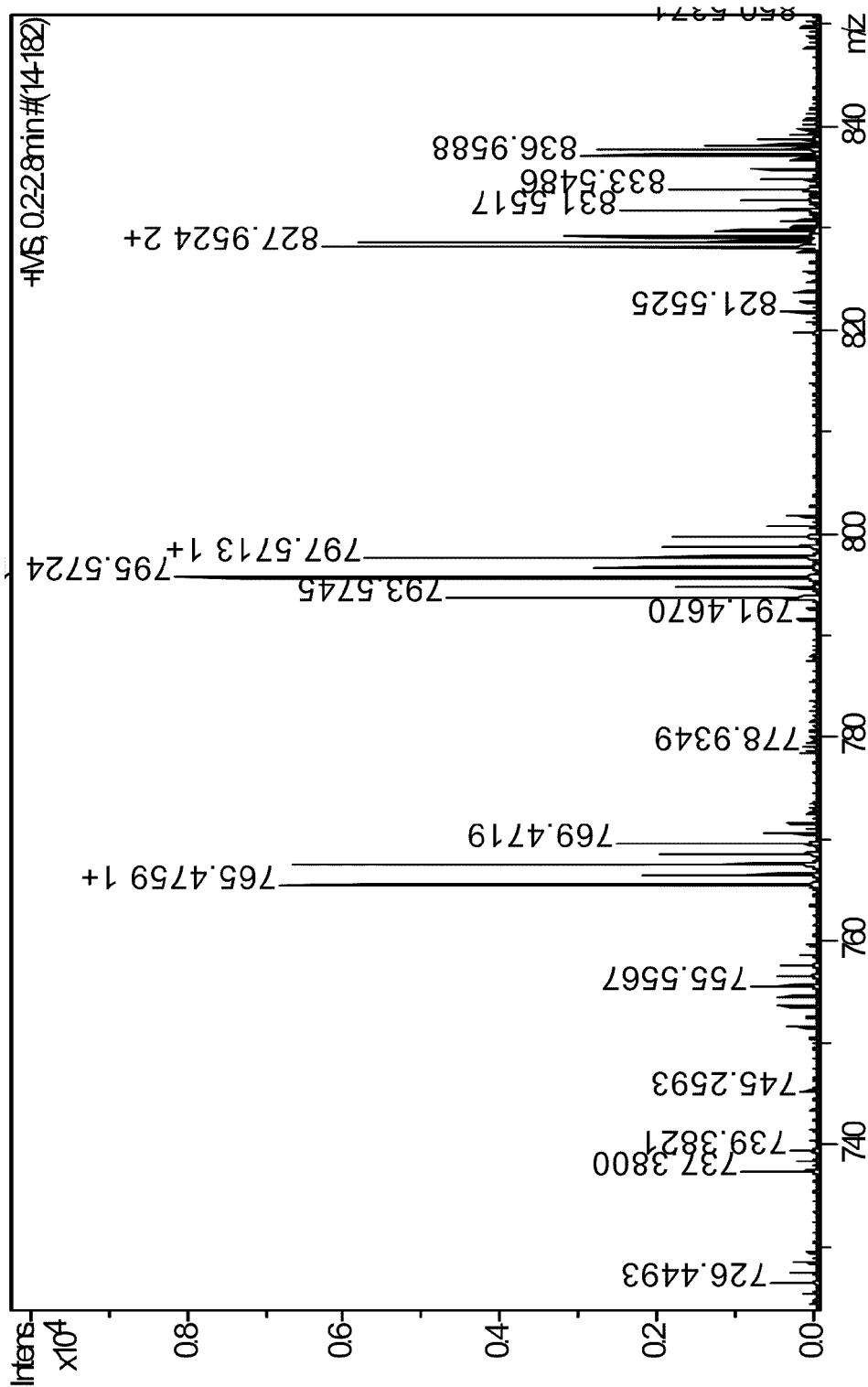

Cholamine labeling of HEK cells. Four 10 cm plates of 95% confluent HEK293 cells grown in Dulbecco's Modified Eagle's Minimal Essential Medium (DMEM) supplemented with 10% Fetal Bovine Serum (FBS) were transfected with 10 µg of either pcDNA 3.1 or SIRT1 construct and lipofectamine 2000 (Invitrogen) as described by manufacturer. Cells were scraped from the plates in 1× Phosphate Buffered Saline (PBS) and pelleted by centrifugation at 600×g for 5 min and washed with 1×PBS twice. Cells were resuspended in 10 mL of PBS and counted. An equal number of cells from each plate were pelleted and then one plate from each transfection was lysed by addition of 2:1 chloroform:methanol. The cells were incubated for 10 min in each solution. The extracts were then centrifuged at 16 kXg to pellet the solids. The supernatant was removed from the pellet and was dried by speedvac. A solution of 9:1 acetonitrile:5M HCl was prepared. 500 µL of which was added to each of dried-down lipid extract samples (extract was from ~5.5 million cells), which was refluxed for ~2 h to saponify lipids, reduced to dryness in a speed vac, and re-dissolved in 200 µL of the labeling mixture (in DMSO). Fatty acid amount was roughly calculated to be 16 nmol from 5.5 million cells. 100 equivalents of cholamine, 200 equivalents of triethylamine, 10 equivalents of HOBt and 10 equivalents of Hbtu were included in the labeling mixture. The heavy and light products were mixed 1:1 prior to RP LC-MS analysis. The data and results is shown in FIG. 19.

Example 13

Modifying proteins or peptides with fixed-charge functional groups leads to higher charge state ions from electrospray ionization mass spectrometry (ESI-MS), which is often advantageous in mass spectrometric analysis. The fixed charge in this particular example is due to a quaternary ammonium group in the labeling reagent, which is attached to the carboxylic acid functional groups of the peptide/protein via an amidation reaction. This permanent positive charge thereby replaces a potential negative charge (deprotonated carboxylic acid), which leads to significantly more charges from positive-ion mode ESI, the preferred mode for peptide and protein ESI-MS.

Labeling of Neurotensin with Cholamine. The amino acid sequence of Neurotensin is pGlu-Leu-Tyr-Glu-Asn-Lys-Pro-Arg-Arg-Pro-Tyr-Ile-Leu (SEQ ID NO: 5). This peptide has two potential sites for labeling, namely the glutamic acid (Glu) residue and the C-terminus. Note that the pGlu residue contains an amide group rather than a free carboxylic acid. Table 2 contains a list of expected m/z values for various charge states of unlabeled neurotensin along with neurotensin that has one or two cholamine labels. The mass spectra in FIGS. 20-24 are expanded views of the spectrum obtained from the cholamine-labeled neurotensin sample. Generic labeling reaction conditions were employed for this sample, and as such it contains all three possible peptides (0, 1, and 2 cholamine labels); however, the labeled product peaks were more intense than those from the unlabeled peptides. The spectra show: (i) the unlabeled neurotensin was observed in the +2 and +3 charge states only, (ii) neurotensin with 1 cholamine label was observed in the +2, +3, and +4 charge states, and (iii) neurotensin with 2 cholamine labels was observed in the +3, +4, and +5 charge states. Clearly, cholamine labeling has significantly increased the charge state of the peptide ions obtained by electrospray ionization mass spectrometry.

TABLE 2

|  | Neutral | +1 | +2 | +3 | +4 | +5 | +6 | +7 |
|---|---|---|---|---|---|---|---|---|
| Unlabeled | 1671.909 | 1672.917 | 836.9624 | 558.3109 | 418.9851 |  |  |  |
| 1 Label |  | 1757.022 | 879.0147 | 586.3457 | 440.0113 | 352.2106 |  |  |
| 2 Labels |  |  | 921.067 | 614.3806 | 461.0374 | 369.0315 | 307.6942 |  |

Example 14

Peptide/protein labeling for improved ETD. Labeling peptides or proteins at their carboxylic acid groups using reagents that incorporate quaternary ammonium groups has a dramatic effect on the mass spectrometric results for that peptide or protein. The increase in the charge state of such a peptide was demonstrated in the previous example. In this example, a protein is modified with quaternary ammonium groups, followed by digestion of that protein with trypsin to create many modified peptides, which show significantly improved electron transfer dissociation (ETD) mass spectra.

In order to attach quaternary amine groups to the carboxylic acids of a protein, a simple three-step methodology was employed. An important aspect of this work is that the labeling reactions have been optimized to yield a pure protein or peptide product after the three-step methodology. The three steps include blocking sulfhydryls (cysteine residues), blocking amines (lysine residues and N-terminus), and then amidating the carboxylic acids (aspartic and glutamic acid residues as well as the C-terminus). Note that blocking sulfhydryls by reduction and alkylation is already conventionally performed for mass spectrometric analysis of proteins and peptides.

The experimental details of the three-step methodology are provided herein. The protein thiols (sulfhydryl groups) were reduced and alkylated with dithiothreitol (DTT) and iodoacetamide (IAA). Then, the amino groups were methylated by reductive methylation using 20 mM formaldehyde and 30 mM pyridine-borane in 6 M guanidine-HCl, 20% methanol, and 300 mM triethanolamine buffer at pH 7.5. The carboxylic acid groups were amidated with an amine compound that also contained a quaternary ammonium group $[H_2N(CH_2)_4N^+(CH_3)_3]Cl^-$, whereby that molecule is similar to cholamine but with a longer carbon chain. The amidation step on whole proteins employed the coupling reagent (7-azabenzotriazol-1-yloxy)-tripyrrolidinophosphonium hexafluorophosphate (PyAOP) at 50 mM in wet DMSO (~5% $H_2O$) buffered with 500 mM of the $[H_2N(CH_2)_4N^+(CH_3)_3]Cl^-$ and 250 mM of the base N-methylmorpholine. The weakly basic, buffered conditions and PyAOP as a coupling reagent were critical for clean reaction conversions. After these three modifications, the protein was purified by a microcon filter and then digested with trypsin. The protein employed for this example was lysozyme from hen egg white. The heavy version of the labeling reagent would preferably be [$H_2N(CH_2)_4N^+(CD_3)_3$] $Cl^-$, whereby any halide is suitable.

As a control, an "unmodified" lysozyme protein was digested with trypsin after reducing and alkylating its sulfhydryls with DTT and IAA.

Figure 26:
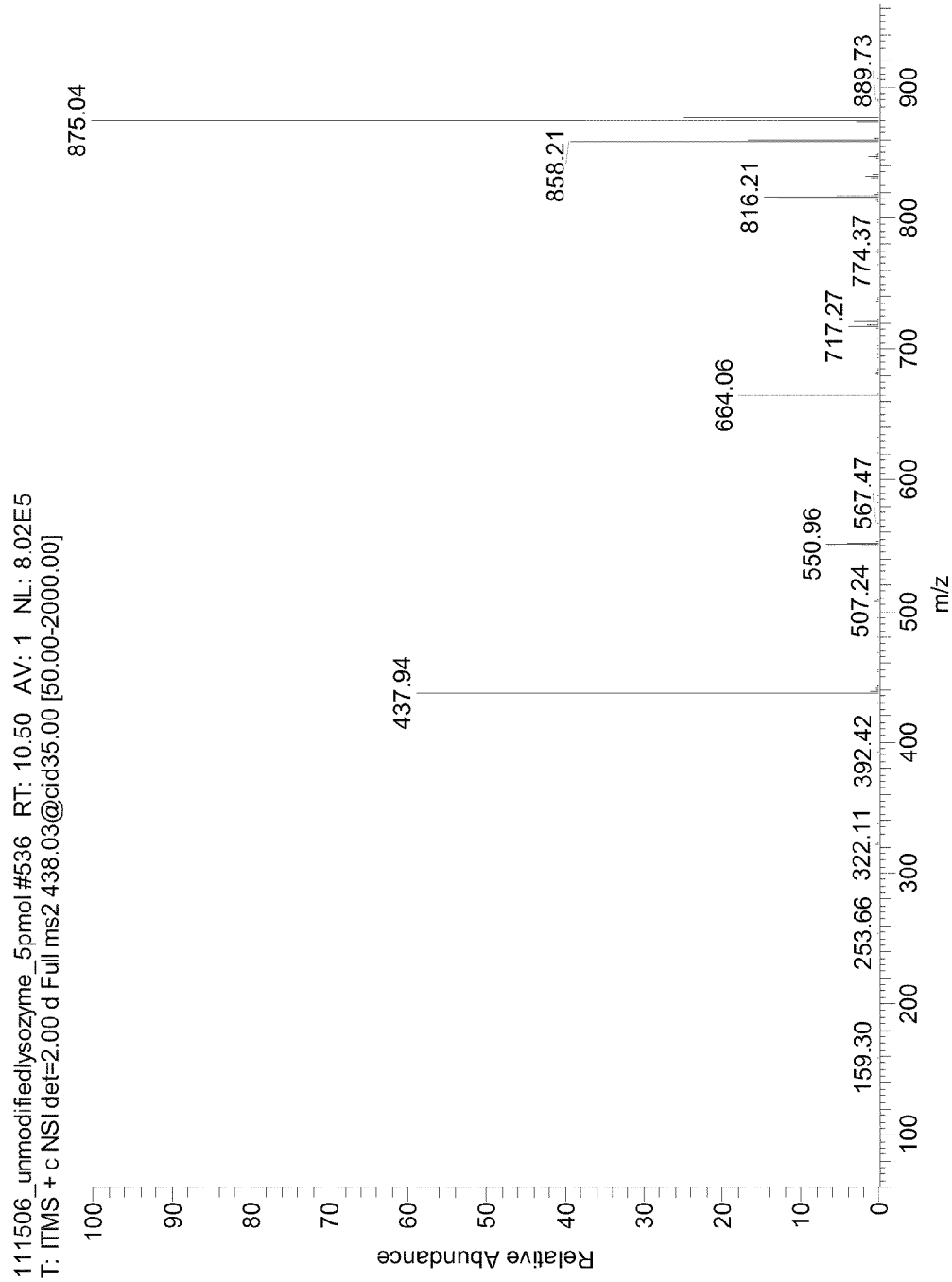
FIG. 26 is a mass spectrum obtained after electron transfer dissociation (ETD) of the +2 charge state of the HGLDNYR tryptic peptide of the "unmodified" lysozyme protein, whereby only 5 of the 12 possible c- and z-type fragment ions were observed in this spectrum.
Figure 27:
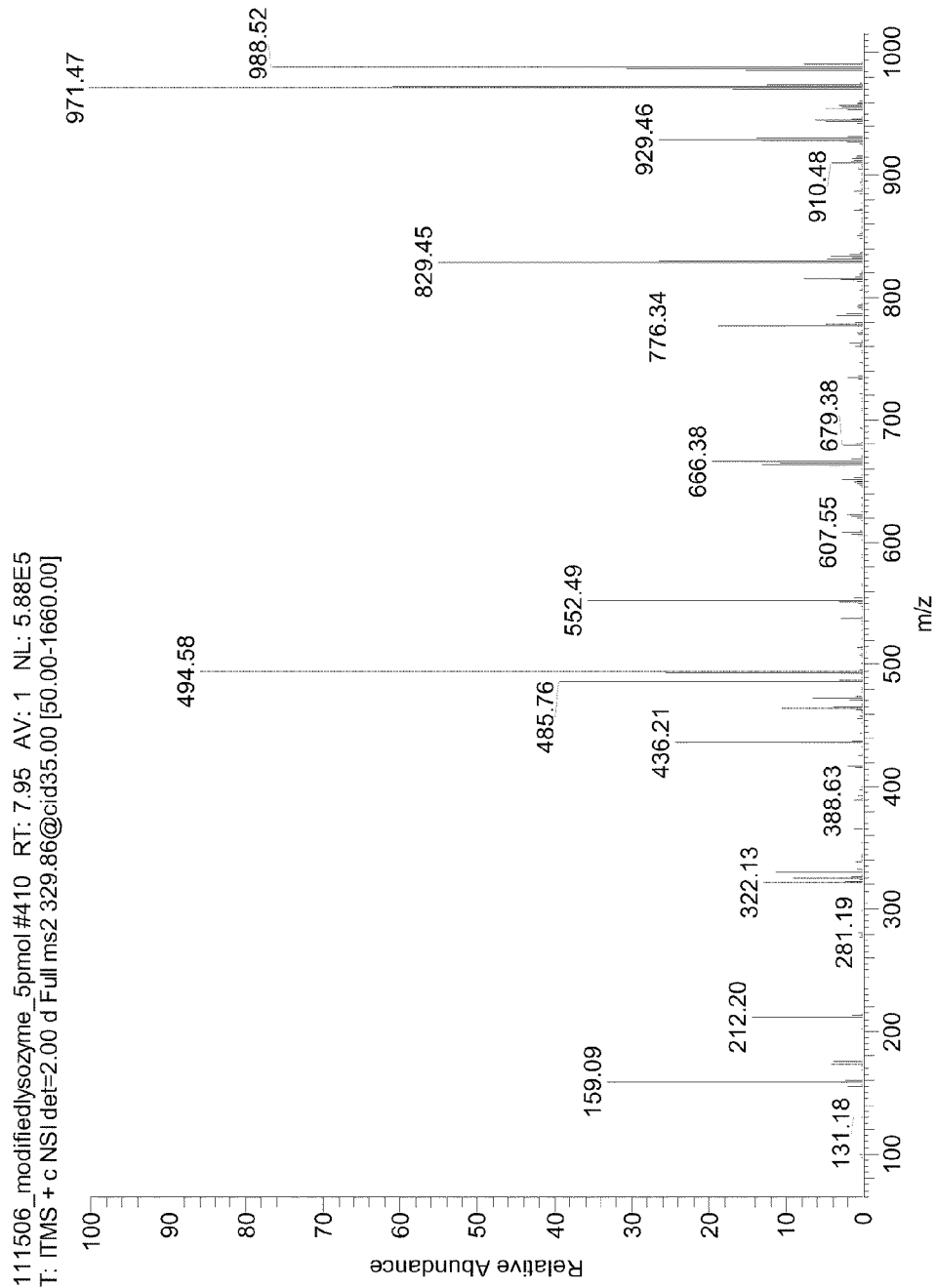
FIG. 27 is a mass spectrum obtained after ETD of the +3 charge state of the HGLD*NYR tryptic peptide of the quaternary-amine-labeled lysozyme sample. This peptide has a quaternary-amine fixed-charge label on the aspartic acid residue, which enabled the formation of the +3 ion during ESI, whereby this ETD fragmentation spectrum shows all 12 possible c- and z-type fragment ions for this modified peptide.

The tryptic digests (5 picomoles of each sample) were separated in a 50 μm i.d. reverse-phase C18 LC column coupled to online ESI-MS using a ThermoFinnegan LTQ linear ion trap mass spectrometer equipped with electron transfer dissociation (ETD) capabilities. FIG. 26 shows the ETD spectrum of the +2 charge state of the HGLDNYR (SEQ ID NO: 6) tryptic peptide of the "unmodified" lysozyme protein (note that the +3 charge state was not observed). Relatively little structural information is obtained from this spectrum due to the poor ETD fragmentation as expected from low m/z peptide ions. In contrast, the spectrum in FIG. 27 shows many ETD fragment peaks for the +3 ion of the analogous peptide (HGLD*NYR) from the quaternary-amine-labeled lysozyme sample. Due to the quaternary-amine fixed-charge label on the aspartic acid residue, this modified peptide acquired an extra charge during electrospray ionization and was dissociated by ETD as the +3 charge state ion. The dramatic increase in the number of fragments for the modified peptide occurs because ETD fragmentation is more effective on more highly charged peptides. All 12 possible c- and z-type fragment ions were observed for the modified peptide yielding 100% sequence coverage, whereas only 5 of 12 fragment ions were observed for the unmodified peptide (40% sequence coverage). The result of this improved fragmentation is a much higher probability of identifying a protein (either through database searching or by de novo sequencing).

The spectra in FIGS. 26 and 27 serve as one example of the improvement in ETD when quaternary ammonium groups are attached to the acid groups of peptides or proteins. Other data includes: All of the resulting spectra from the lysozyme LC-MS runs were searched against a database retrieval algorithm. This algorithm was able to identify 106 of the 129 amino acids in the lysozyme sequence (82% sequence coverage) from the ETD tandem mass spectra for the quaternary ammonium modified lysozyme. With data resulting from the "unmodified" protein (using an identical workflow), the algorithm was able to identify only 51 of the 129 amino acids from the ETD tandem mass spectra (40% sequence coverage).

Another specific peptide example from this data set involves the peptide having the sequence CELAAAMKR (SEQ ID NO: 7). In the unmodified sample, the peptide was not identified, but by manual inspection was present in the chromatogram as the +2 precursor ion (residue-to-charge ratio of 4.5). ETD fragmentation generated one out of 16 possible product ions. However, the quaternary ammonium modified version of this peptide, CE*LAAAMKR, was observed in the +3 charge state (residue-to-charge ratio was reduced to 3.0), which then generated 15 of 16 possible ETD product ions upon dissociation. These results demonstrate that attaching fixed-charge modifications to amino acids reduces the residue-to-charge ratio of electrosprayed peptides so that the overall sequence coverage for a protein is increased upon ETD fragmentation.

Thus, pairing these quaternary ammonium group labeled peptides and proteins with ETD is an exemplary embodiment. Other fragmentation methods such as electron capture dissociation (ECD) and collision-induced dissociation (CID) may also benefit from the higher charge states afforded by the labels. However, we have shown that ETD does not cause the deleterious trimethylamine loss, as sometimes occurs with quaternary ammonium groups during CAD.

Another benefit of this labeling methodology is that the carboxylic acid groups are blocked by the amidation reaction. This feature is especially advantageous for analyzing proteins having phosphate groups as post-translational modifications. These phosphoproteins are very important biologically and are the focus of many proteomics studies. Selective enrichment of phosphopeptides (from tryptic digests of phosphoproteins) often is performed with IMAC (immobilized-metal affinity chromatography). Carboxylic acid groups interfere with this procedure and therefore are usually blocked by conversion to the methyl esters. The labeling proposed herein accomplishes this blocking function. Furthermore, ETD is an exemplary fragmentation mechanism for analyzing phosphopeptides because the phosphate group does not fall off, as often occurs during CAD. Thus, a single labeling reaction performs two beneficial functions for phosphopeptide analysis: It blocks the carboxylic acid groups to aid IMAC purification, and it improves the ETD analysis due to the production of higher charge state ions.

These quaternary ammonium labeled peptides/proteins will enable both ETD analysis, as described in this example, as well as relative quantification studies, as discussed herein. In other words, a single mass spectrometric analysis of labeled peptides or proteins will provide both precise relative quantification (via the use of isotopic variants) as well as improved protein identification (via ETD fragmentation of the more highly charged ions).

While this invention has been described in conjunction with various exemplary embodiments set forth herein, the invention includes alternatives, modifications, variations, improvements and/or equivalents that are apparent or foreseeable to the ordinary artisan. Accordingly, the exemplary embodiments set forth herein are non-limiting and illustrative. Changes may be made to the exemplary embodiments within the scope of the invention without departing from the spirit of the invention. The invention, therefore, embraces suitable relevant earlier known alternatives, modifications, variations, improvements and substantial equivalents, conventional or otherwise.

We claim:

1. A composition comprising an isotopically enriched heavy quaternary amine compound for use as a labeling reagent in mass spectrometry according to the formula:

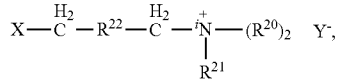

wherein Y⁻ is a suitable anion;
wherein X is $NH_2$ or $NH_3$;
wherein any number of carbons in the compound are $^{12}C$ or $^{13}C$;
wherein any number of nitrogens in the compound are $^{14}N$ or $^{15}N$;
wherein $R^{22}$ is selected from the group consisting of a bond; $C_1$-$C_{30}$ linear or branched, saturated or unsaturated alkylene; aryl, aliphatic ring, oxygen-containing aliphatic ring, halogenated aryl, O, $C_1$-$C_{12}$ linear or branched ether, $C_1$ to $C_{12}$ linear or branched polyether, $C_1$-$C_{28}$ branched or linear ester, and, $C_1$-$C_{28}$ branched or linear amide;
wherein $R^{20}$ and $R^{21}$ are each independently selected from a group consisting of $C_1$-$C_4$ branched or linear, saturated or unsaturated alkyl groups, wherein at least one of $R^{20}$ or $R^{21}$ contains at least one carbon that is $^{13}C$ or at least one hydrogen that is deuterium; and
wherein the isotopically enriched heavy quaternary amine compound is present in an amount in excess of the natural isotopic abundance.

2. The compound of claim 1 wherein one or more carbons in $R^{20}$ is $^{13}C$.

3. The compound of claim 1 wherein one or more carbons in $R^{21}$ is $^{13}C$.

4. The compound of claim 1 wherein each carbon in $R^{20}$ and $R^{21}$ is $^{13}C$.

5. The compound of claim 1 wherein each carbon in $R^{20}$ is $^{12}C$, and wherein each carbon in $R^{21}$ is $^{13}C$.

6. The compound of claim 1 wherein each carbon in $R^{20}$ is $^{13}C$, and wherein each carbon in $R^{21}$ is $^{12}C$.

7. The compound of claim 1 wherein $R^{20}$ and $R^{21}$ are each independently $C_1$-$C_2$ linear, saturated alkyl groups, wherein each carbon in $R^{20}$ is $^{12}C$, and wherein each carbon in $R^{21}$ is $^{13}C$.

8. The compound of claim 1 wherein $R^{20}$ and $R^{21}$ are each independently $C_1$-$C_2$ linear, saturated alkyl groups, wherein each carbon in $R^{21}$ is $^{12}C$, and wherein each carbon in $R^{20}$ is $^{13}C$.

9. The compound of claim 1 wherein $R^{20}$ and $R^{21}$ are each a member selected from the group consisting of $^{13}CH_3$ and $^{13}CD_3$.

10. The compound of claim 1 wherein $R^{20}$ and $R^{21}$ are selected from the group consisting of $^{12}CD_3$ and $^{12}CH_3$, wherein at least one of $R^{20}$ and $R^{21}$ is $^{12}CD_3$.

11. The compound of claim 1 wherein $R^{20}$ and $R^{21}$ contain at least one hydrogen that is deuterium.

12. The compound of claim 1 wherein $R^{22}$ is selected from the group consisting of a bond, $CH_2$ and $(CH_2)_2$.

13. The compound of claim 1 wherein at least one carbon in $R^{22}$ is $^{13}C$.

14. The compound of claim 1 wherein the heavy quaternary amine has the formula:

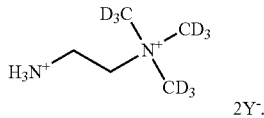

15. A quaternary amine kit suitable for reacting with carboxylic acid groups in target molecules for use in mass spectrometry comprising:
a) a first composition comprising an isotopically enriched heavy quaternary amine compound according to the formula:

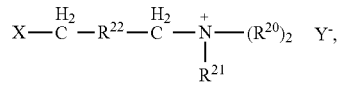

wherein Y⁻ is a suitable anion;
wherein X is $NH_2$ or $NH_3$;
wherein any number of carbons in the compound are $^{12}C$ or $^{13}C$;
wherein any number of nitrogens in the compound are $^{14}N$ or $^{15}N$;
wherein $R^{22}$ is selected from the group consisting of a bond; $C_1$-$C_{30}$ linear or branched, saturated or unsaturated alkylene; aryl, aliphatic ring, oxygen-containing aliphatic ring, halogenated aryl, O, $C_1$-$C_{12}$ linear or branched ether, $C_1$ to $C_{12}$ linear or branched polyether, $C_1$-$C_{28}$ branched or linear ester, and, $C_1$-$C_{28}$ branched or linear amide;
wherein $R^{20}$ and $R^{21}$ are each independently selected from a group consisting of $C_1$-$C_4$ branched or linear, saturated or unsaturated alkyl groups, wherein at least one of $R^{20}$ or $R^{21}$ contains at least one carbon that is $^{13}C$ or at least one hydrogen that is deuterium, and
wherein the isotopically enriched heavy quaternary amine compound is present in an amount in excess of the natural isotopic abundance; and
b) a second composition comprising a light quaternary amine compound structurally identical to the heavy quaternary amine compound with the proviso that the light quaternary amine compound is at least around 1 Dalton less in weight than the heavy quaternary amine compound.

16. The quaternary amine kit of claim 15, with the proviso that the light quaternary amine compound is at least around 2 Daltons less in weight than the heavy quaternary amine compound.

17. The quaternary amine kit of claim 15 wherein $R^{20}$ and $R^{21}$ are each independently $C_1$-$C_2$ linear, saturated alkyl groups, wherein each carbon in $R^{20}$ is $^{12}C$, and wherein each carbon in $R^{21}$ is $^{13}C$.

18. The quaternary amine kit of claim 15 wherein $R^{20}$ and $R^{21}$ are each independently $C_1$-$C_2$ linear, saturated alkyl groups, wherein each carbon in $R^{21}$ is $^{12}C$, and wherein each carbon in $R^{20}$ is $^{13}C$.

19. The quaternary amine kit of claim 15 wherein $R^{20}$ and $R^{21}$ are each a member selected from the group consisting of $^{13}CH_3$ and $^{13}CD_3$.

20. The quaternary amine kit of claim 15 wherein $R^{20}$ and $R^{21}$ are selected from the group consisting of $^{12}CD_3$ and $^{12}CH_3$, wherein at least one of $R^{20}$ and $R^{21}$ is $^{12}CD_3$.

21. The quaternary amine kit of claim 15 wherein $R^{20}$ and $R^{21}$ contain at least one hydrogen that is deuterium.

22. The quaternary amine kit of claim 15 wherein $R^{22}$ is selected from the group consisting of a bond, $CH_2$ and $(CH_2)_2$.

23. The quaternary amine kit of claim 15 wherein at least one carbon in $R^{22}$ is $^{13}C$.

24. The quaternary amine kit of claim 15 wherein the heavy quaternary amine has the formula:

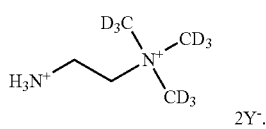

2Y⁻.

25. A method of labeling target molecules containing carboxylic acid groups for use in mass spectrometry comprising:
   a) providing one or more target molecules; and
   b) reacting the target molecules with a composition comprising:
      i) an isotopically enriched heavy quaternary amine compound according to the formula:

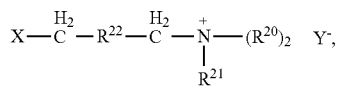

wherein Y⁻ is a suitable anion;
   wherein X is $NH_2$ or $NH_3$;
   wherein any number of carbons in the compound are $^{12}C$ or $^{13}C$;
   wherein any number of nitrogens in the compound are $^{14}N$ or $^{15}N$;
   wherein $R^{22}$ is selected from the group consisting of a bond; $C_1$-$C_{30}$ linear or branched, saturated or unsaturated alkylene; aryl, aliphatic ring, oxygen-containing aliphatic ring, halogenated aryl, O, $C_1$-$C_{12}$ linear or branched ether, $C_1$ to $C_{12}$ linear or branched polyether, $C_1$-$C_{28}$ branched or linear ester, and, $C_1$-$C_{28}$ branched or linear amide; and
   wherein $R^{20}$ and $R^{21}$ are each independently selected from a group consisting of $C_1$-$C_4$ branched or linear, saturated or unsaturated alkyl groups, wherein at least one of $R^{20}$ or $R^{21}$ contains at least one carbon that is $^{13}C$ or at least one hydrogen that is deuterium;
   wherein the isotopically enriched heavy quaternary amine compound is present in an amount in excess of the natural isotopic abundance; and ii) a light quaternary amine compound structurally identical to the heavy quaternary amine compound with the proviso that the light quaternary amine compound is at least around 1 Dalton less in weight than the heavy quaternary amine compound.

26. The method of claim 25, with the proviso that the light quaternary amine compound is at least around 2 Daltons less in weight than the heavy quaternary amine compound.

27. The method of claim 25 wherein $R^{20}$ and $R^{21}$ are each independently $C_1$-$C_2$ linear, saturated alkyl, wherein each carbon in $R^{20}$ is $^{12}C$, and wherein each carbon in $R^{21}$ is $^{13}C$.

28. The method of claim 25 wherein $R^{20}$ and $R^{21}$ are each independently $C_1$-$C_2$ linear, saturated alkyl, wherein each carbon in $R^{21}$ is $^{12}C$, and wherein each carbon in $R^{20}$ is $^{13}C$.

29. The method of claim 25 wherein $R^{20}$ and $R^{21}$ are each a member selected from the group consisting of $^{13}CH_3$ and $^{13}CD_3$.

30. The method of claim 25 wherein $R^{20}$ and $R^{21}$ are selected from the group consisting of $^{12}CD_3$ and $^{12}CH_3$, wherein at least one of $R^{20}$ and $R^{21}$ is $^{12}CD_3$.

31. The method of claim 25 wherein $R^{20}$ and $R^{21}$ contain at least one hydrogen that is deuterium.

32. The method of claim 25 wherein $R^{22}$ is selected from the group consisting of a bond, $CH_2$ and $(CH_2)_2$.

33. The method of claim 25 wherein at least one carbon in $R^{22}$ is $^{13}C$.

34. The method of claim 25 wherein the heavy quaternary amine has the formula:

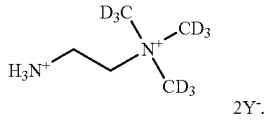

2Y⁻.

35. The method of claim 25 further comprising:
   a) introducing the target molecules into an RF ion trap;
   b) introducing gas-phase anions into the RF ion trap;
   c) mixing gas-phase anions and multiply-charged target molecule cations so as to facilitate electron transfer from the anions to the multiply-charged target molecule cations inducing the production of electron transfer dissociation product ions;
   d) terminating the reactions by physically separating the remaining gas-phase anions from the electron transfer product cations; and
   e) conducting m/z analysis of cations remaining in the trap, wherein the charge state of the labeled target molecules is increased due to the labeling, and wherein the target molecules are peptides or proteins.

36. The method of claim 35 further comprising purifying the labeled target molecules with immobilized metal affinity chromatography, wherein the target molecules are phosphopeptides or phosphoproteins.

* * * * *

SEQUENCE LISTING

<160> NUMBER OF SEQ ID NOS: 7

<210> SEQ ID NO 1
<211> LENGTH: 29
<212> TYPE: DNA
<213> ORGANISM: Artificial Sequence
<220> FEATURE:
<223> OTHER INFORMATION: synthetic primer

```
<400> SEQUENCE: 1
aggaaggtgt tcgataaaat gactgaatg                                      29

<210> SEQ ID NO 2
<211> LENGTH: 28
<212> TYPE: DNA
<213> ORGANISM: Artificial Sequence
<220> FEATURE:
<223> OTHER INFORMATION: synthetic primer

<400> SEQUENCE: 2
cacatccagt atcatcaacc tcaaacca                                       28

<210> SEQ ID NO 3
<211> LENGTH: 29
<212> TYPE: DNA
<213> ORGANISM: Artificial Sequence
<220> FEATURE:
<223> OTHER INFORMATION: synthetic primer

<400> SEQUENCE: 3
cattttataa taacgctgcg gacatctac                                      29

<210> SEQ ID NO 4
<211> LENGTH: 29
<212> TYPE: DNA
<213> ORGANISM: Artificial Sequence
<220> FEATURE:
<223> OTHER INFORMATION: synthetic primer

<400> SEQUENCE: 4
tttctccata ttgaccatca tactcattg                                      29

<210> SEQ ID NO 5
<211> LENGTH: 13
<212> TYPE: PRT
<213> ORGANISM: Homo Sapien

<400> SEQUENCE: 5

Glu Leu Tyr Glu Asn Lys Pro Arg Arg Pro Tyr Ile Leu
1               5                   10

<210> SEQ ID NO 6
<211> LENGTH: 7
<212> TYPE: PRT
<213> ORGANISM: Artificial Sequence
<220> FEATURE:
<223> OTHER INFORMATION: synthetic peptide

<400> SEQUENCE: 6

His Gly Leu Asp Asn Tyr Arg
1               5

<210> SEQ ID NO 7
<211> LENGTH: 9
<212> TYPE: PRT
<213> ORGANISM: Artificial Sequence
<220> FEATURE:
<223> OTHER INFORMATION: synthetic peptide

<400> SEQUENCE: 7

Cys Glu Leu Ala Ala Ala Met Lys Arg
1               5
```